United States Patent [19]

Kahn et al.

[11] Patent Number: 5,251,126

[45] Date of Patent: Oct. 5, 1993

[54] DIABETES DATA ANALYSIS AND INTERPRETATION METHOD

[75] Inventors: Michael G. Kahn, St. Louis, Mo.; Dijia Huang; Stephen A. Bussmann, both of Granger, Ind.; Steve B. Cousins; Charlene A. Abrams, both of St. Louis, Mo.; James C. Beard, University City, Mo.

[73] Assignee: Miles Inc., Elkhart, Ind.

[21] Appl. No.: 605,400

[22] Filed: Oct. 29, 1990

[51] Int. Cl.⁵ .................. G06F 15/42; G06F 15/74
[52] U.S. Cl. ................................................ 364/413.11
[58] Field of Search ................... 364/413.01, 413.02, 364/413.11, 413.09; 128/DIG. 13, 632, 633, 665, 630, 695; 604/49, 50, 65, 66, 891.1

[56] References Cited

U.S. PATENT DOCUMENTS

| 4,315,309 | 2/1982 | Coli ........................ 364/413.02 |
| 4,712,562 | 12/1987 | Ohayon et al. ................ 128/695 |
| 4,731,726 | 3/1988 | Allen, III ................ 364/413.09 |
| 4,822,337 | 4/1989 | Newhouse et al. ................ 604/50 |

FOREIGN PATENT DOCUMENTS 0290683 11/1988 European Pat. Off. .

OTHER PUBLICATIONS

"A Simplified Approach to Blood Glucose Management", Brochure No. 0441051, Miles Inc., Diagnostics Division, Elkhart, Ind. (1988), 38 pages.

Dorland's Illustrated Medical Dictionary, 27th Ed., Harcourt Brace Johanovich, Inc., Philadelphia, Pa. (1988) pp. 345, 1578.

Bulmer, Principles of Statistics, Dover Publications, Inc., New York, 1979, pp. 139-164.

Berger et al., "Combining Statistical Rule-Based, and Physiologic Model-Based Method to Assist in the Management of Diabetes Mellitus," Computers and Biomedical Research, vol. 23 (1990), pp. 346-357.

Pernick et al., "Personal Computer Programs to Assist with Self-Monitoring of Blood Glucose and Self-Adjustment of Insulin Dosage," Diabetes Care, vol. 9, No. 1, (Jan.-Feb. 1986).

Barr et al., Eds., The Handbook of Artificial Intelligence, vol. 2, William Kaufmann, Inc., Los Altos, Calif. (1982), pp. 175-222.

(List continued on next page.)

Primary Examiner—Roy N. Envall, Jr.
Assistant Examiner—Jennifer L. Hazard
Attorney, Agent, or Firm—Jerome L. Jeffers

[57] ABSTRACT

An automated diabetes data interpretation method is provided which combines symbolic and numeric computing approaches in order to identify and highlight key clinical findings in the patient's self-recorded diabetes data. The patient data, including blood glucose levels and insulin dosage levels, recorded by a diabetic patient over a period of time by means of a glucose meter or the like, is initially downloaded into a central processing system such as a personal computer. The accepted diabetes data is subsequently processed to (a) identify insulin dosage regimens corresponding to pre-defined significant changes in insulin dosage which are found to be sustained for at least a predefined segment of the overall data collection period, (b) identify statistically significant changes in blood glucose levels resulting across adjacent ones of the identified insulin regimen periods, and (c) identify clinically significant changes in blood glucose levels from within the identified statistically significant glucose level changes. The results of the diabetes data processing are generated in the form of a comprehensive yet easily understandable data interpretation report highlighting the processing results, including details pertaining to the identified insulin regimens and the associated clinically significant changes in glucose levels.

58 Claims, 36 Drawing Sheets

OTHER PUBLICATIONS

"New Glucometer ® M Diabetes Management System helps you achieve tighter control," Brochure No. 441021, Miles Inc., Diagnostic Division, Elkhart, Ind. 44102 (1987), 8 pages.
"Glucometer ® M Blood Glucose Meter," Brochure No. 0441023, Miles Inc., Diagnostic Division, Elkhart, Ind. 46515 (1987), 2 pages.
"Glucofacts ™ Data Management System," Brochure No. 0441024, Miles Inc., Diagnostic Division, Elkhart, Ind. 46515 (1987), 2 pages.
"Glucofacts ™ Data Printer," Brochure No. 0441025, Miles Inc., Diagnostics Division, Elkhart, Ind. 46515 (1987), 2 pages.
"Glucofacts ™ Data-Links," Brochure No. 0441059, Miles Inc., Diagnostics Division, Elkhart, Ind. (1989), 2 pages.
"New Glucometer ® M Blood Glucose Meter," Brochure No. 0441041, Miles Laboratories, Inc., Elkhart, Ind. (1987), 2 pages.
"Glucometer ® M Diabetes Management System," Symposium Abstracts, Jun. 26–28, 1987, Omni Ambassador East, Chicago, Ill., 8 pages.
"Glucometer ® M Diabetes Management System," Symposium Abstracts, Jan. 28, 1987, Hyatt Regency Grand Cypress, Orlando, Fla., 12 pages.

FIG. 2

Global Summary:

- There were 4 insulin regimens of which 3 statistically had different effects on blood glucose values overall and at lunch, supper and bedtime.
- The average blood glucose of 138 mg/dl was higher than the upper limit of the patient's prescribed target range of 120 mg/dl.
- No blood glucose values above 375 mg/dl were recorded.
- Extremely low (below 40 mg/dl) blood glucose values occurred at lunch and bedtime.

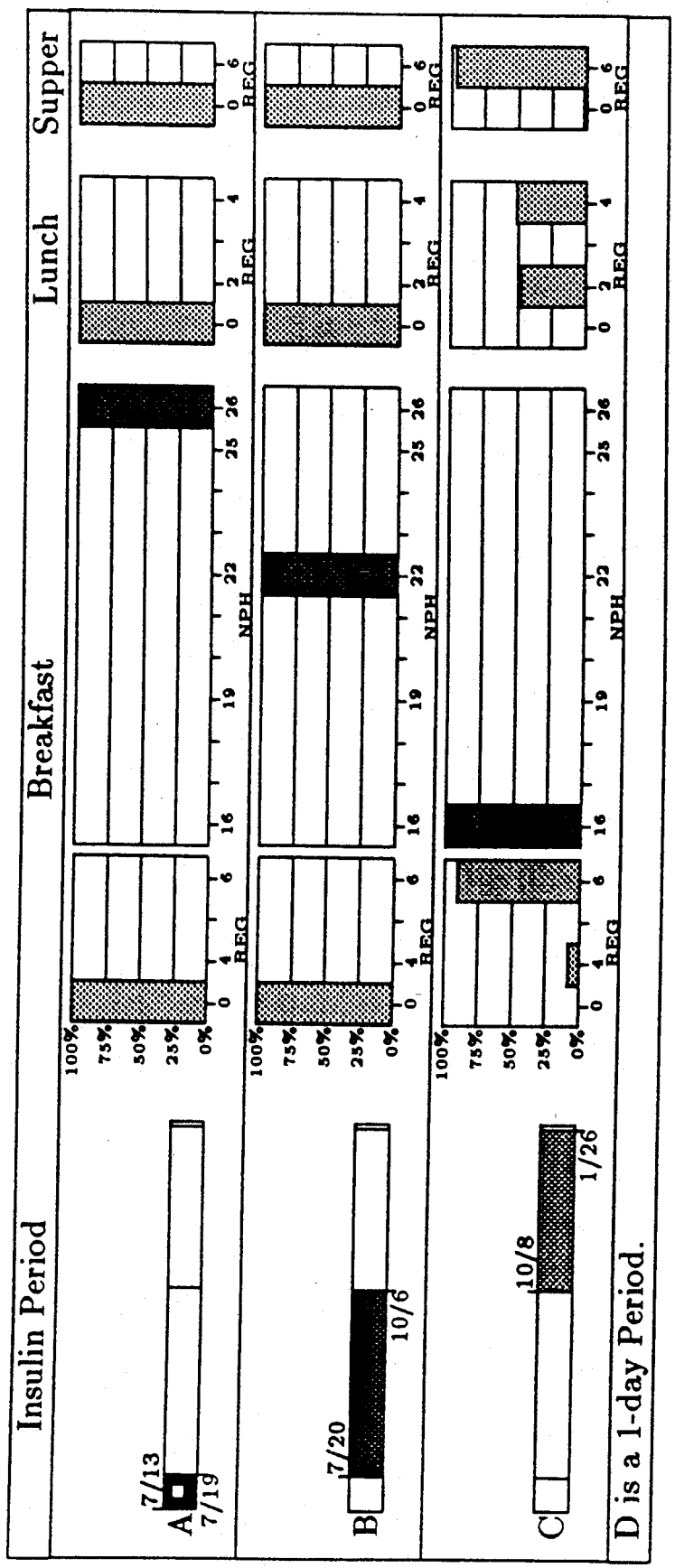

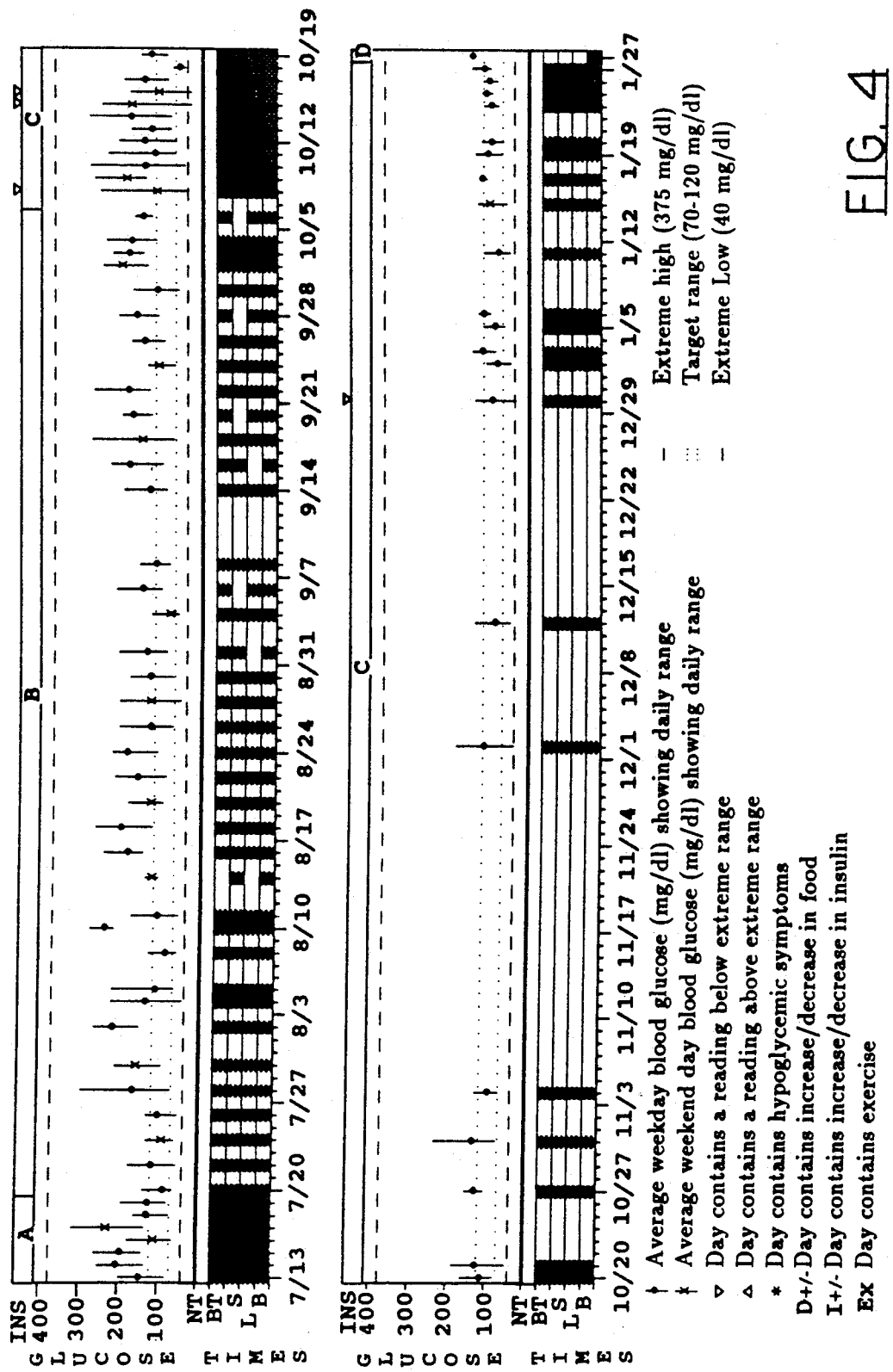

FIG. 5

BG Summary:

Qualitative Summary

|  | Overall | Breakfast | Lunch | Supper | Bedtime |
|---|---|---|---|---|---|
| Mean |  |  | ——— too high ———→ |  |  |
| Spread |  |  | ——— too wide ———→ |  |  |

Therapeutic Issues

|  | Overall | Breakfast | Lunch | Supper | Bedtime |
|---|---|---|---|---|---|
| Distance from goal* | +18 mg/dl | +7 mg/dl | +9 mg/dl | +30 mg/dl | +26 mg/dl |
| Complicating Factors | — | — | 8/75 actual hypos★ | 16/74 potential hypos‡ | 13/77 potential hypos‡ |

*Distance between mean glucose in period and nearest end of patient's target range
★Observed in this data set
‡Expected if current values all shifted down by 'Distance from Goal'

BG by Mealtime:

FIG. 7  BG by Weekday vs. Weekend:

FIG. 8 Overall:

FIG. 9
Lunch:
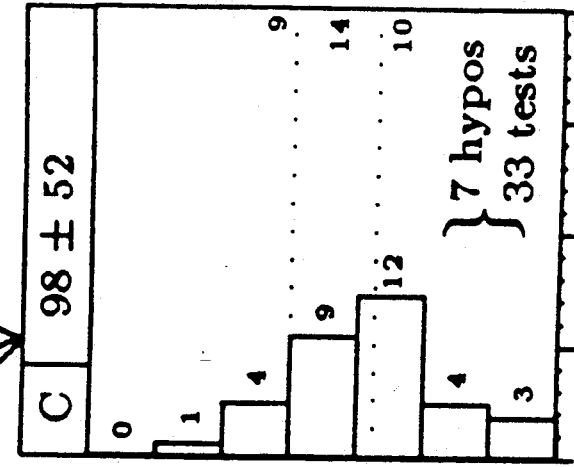
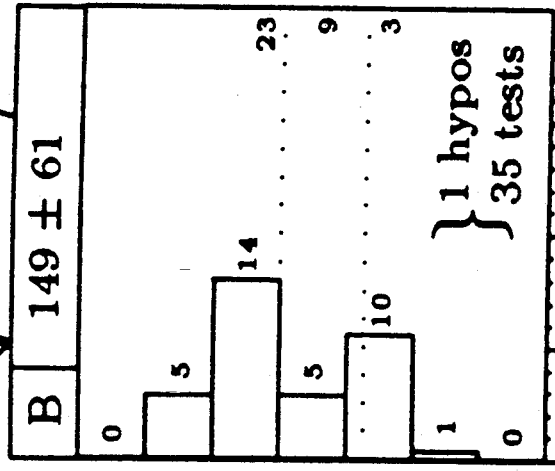
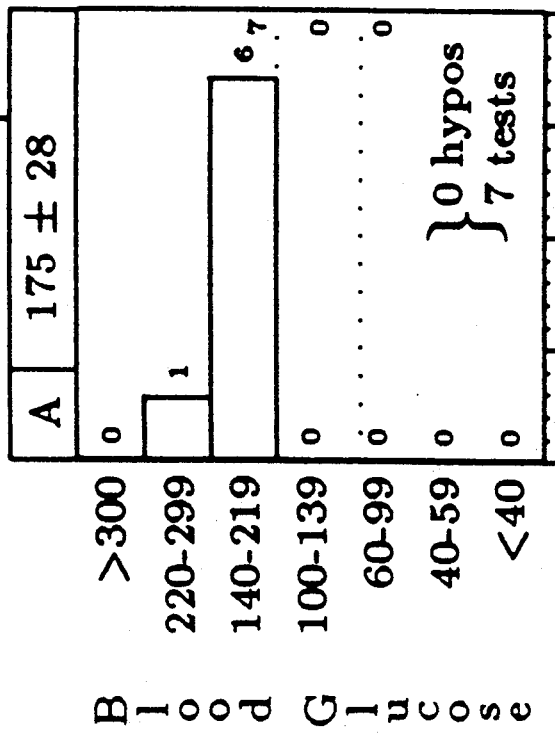

FIG. 11
Bedtime:
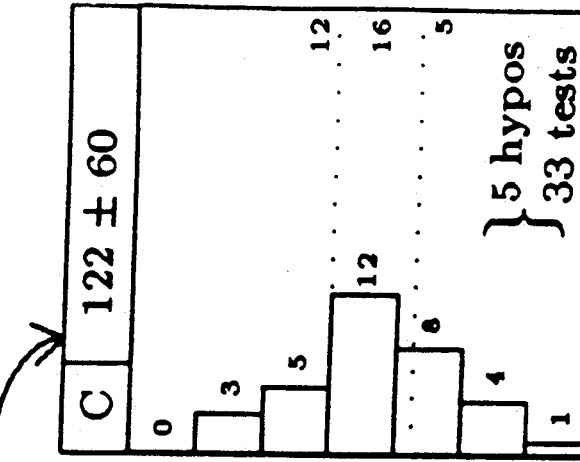
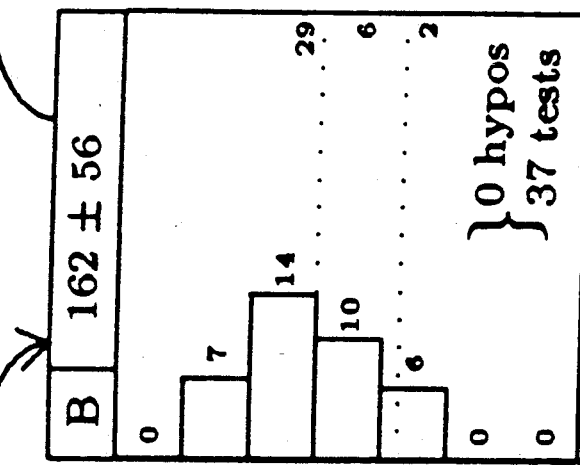
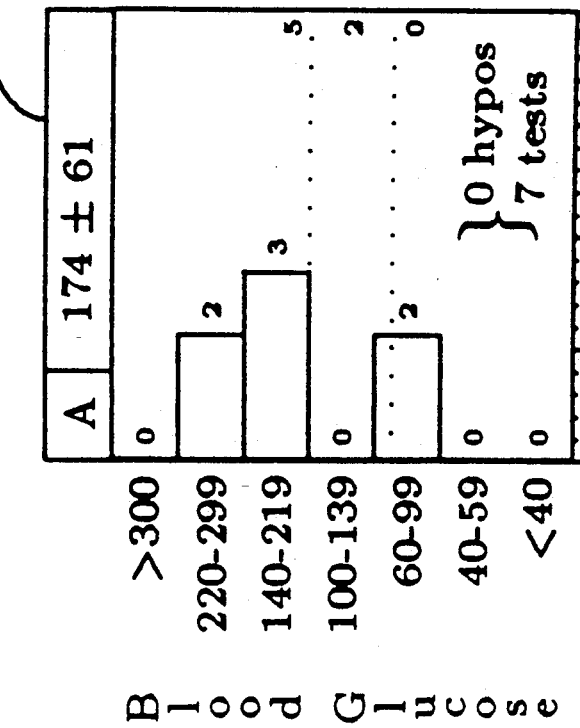
D eliminated from analysis FIG. 20A
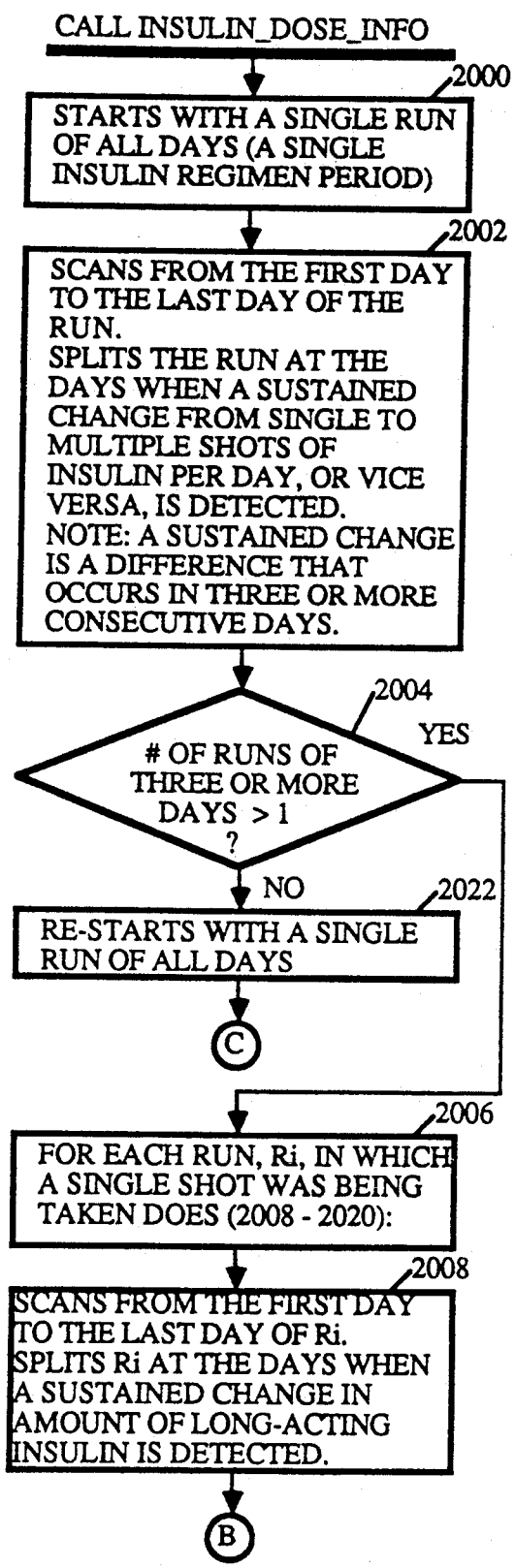
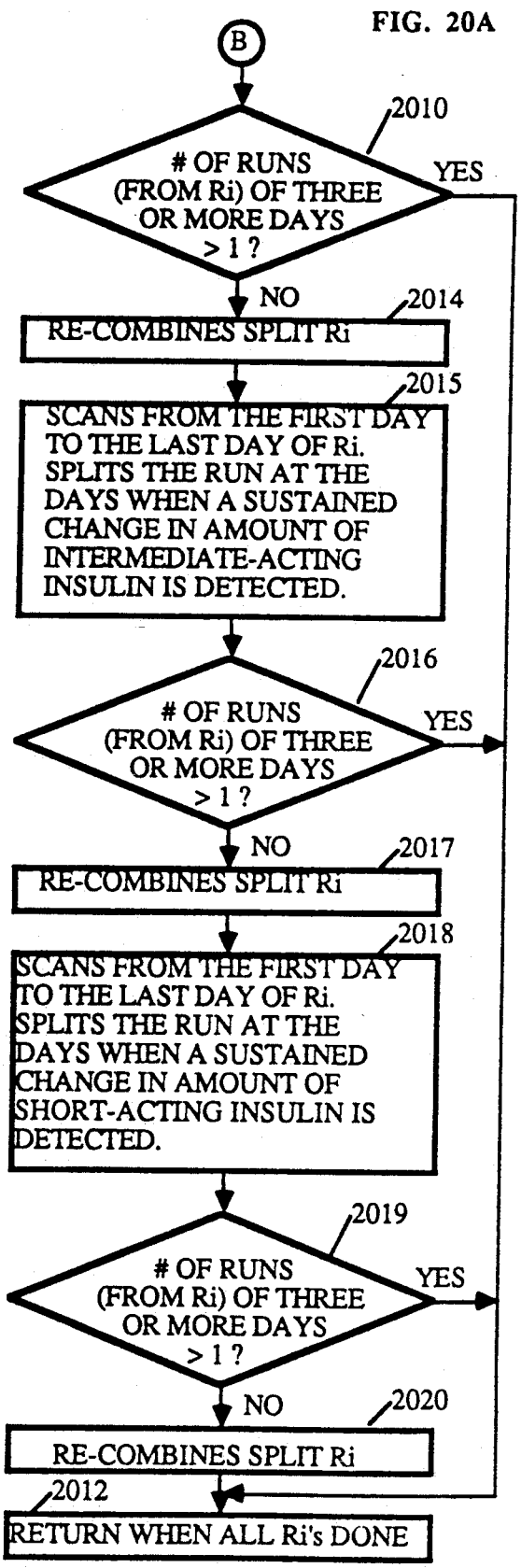

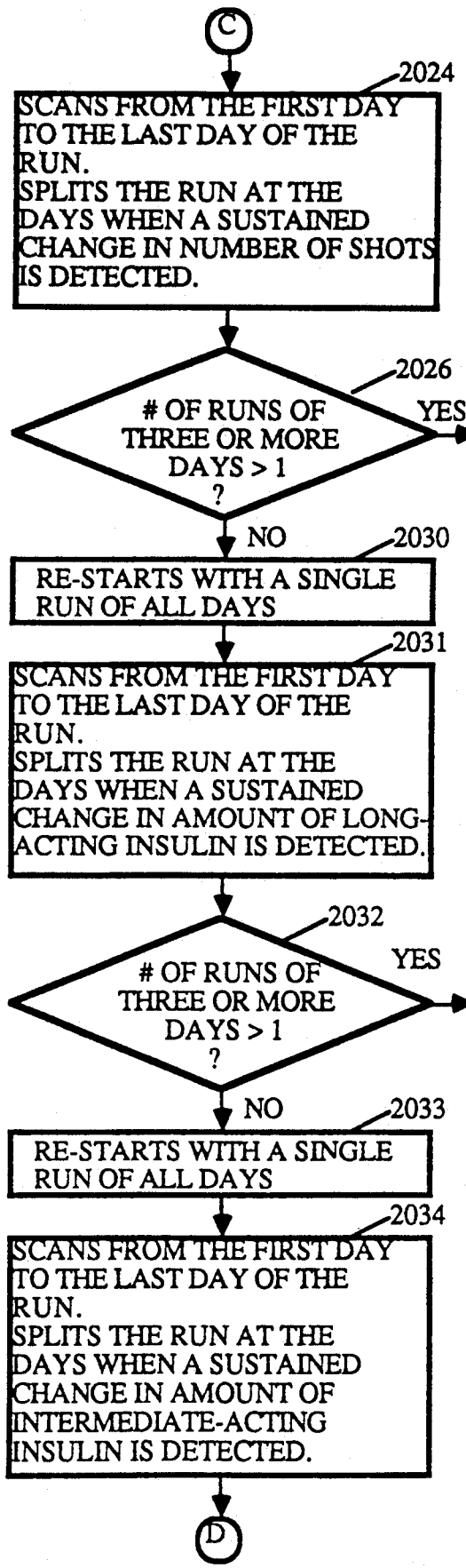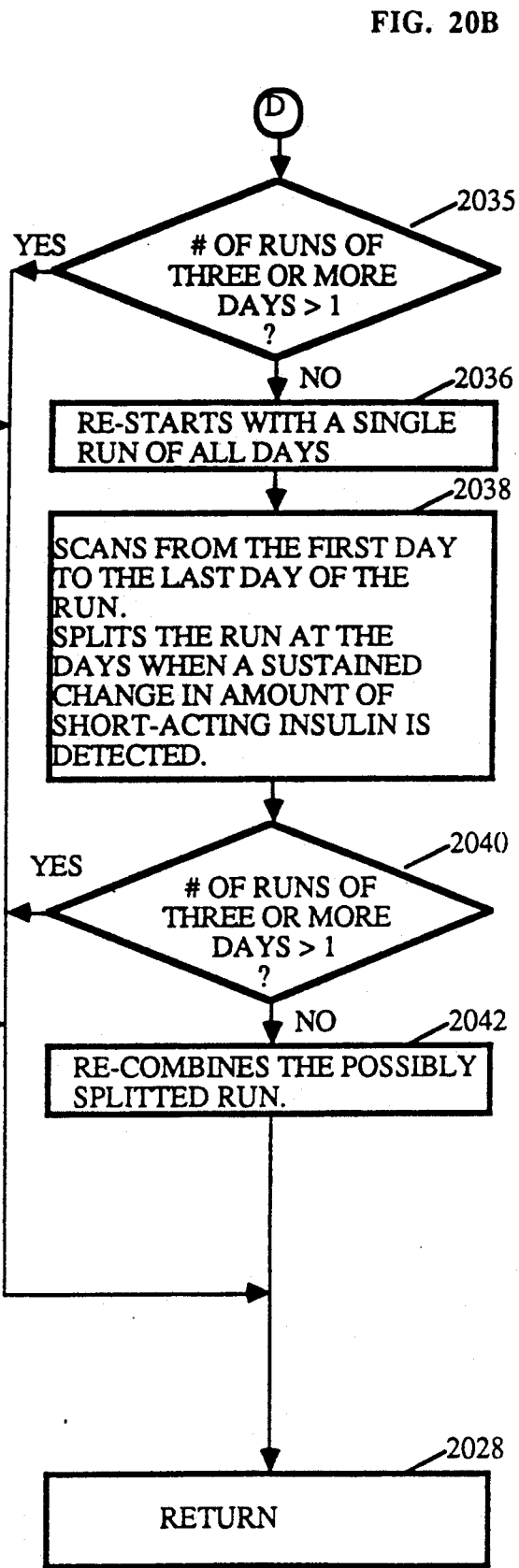
FIG. 20B

DIABETES DATA ANALYSIS AND INTERPRETATION METHOD

BACKGROUND OF THE INVENTION

1. Field of the Invention

This invention generally relates to the field of diabetes management tools. More specifically, this invention relates to a system for automated analysis and interpretation of glucose data collected from diabetic patients.

2. Description of the Prior Art

Home glucose monitoring by diabetics is becoming increasingly routine in modern-day diabetes management. Patients are typically required to maintain hand-written paper log books for manually recording glucose readings and other relevant information. More specifically, patients now measure their blood glucose at scheduled times, possibly to determine the amount of insulin based on the current blood glucose result, and record this information in a personal log book.

Physicians are subsequently faced with the task of carefully reviewing the hand-recorded data for use in optimizing the patient's diabetes therapy. In order to make intelligent and meaningful decisions regarding therapeutic modifications, it becomes necessary for the examining physician to not only summarize the available information but, more importantly, to analyze hundreds of time-dependant observations collected over an extended period of time in order to spot unusual and clinically significant features requiring any modifications of the patient's current diabetes management schedule. The recorded data typically extends over a period of time spanning several weeks or months and constitutes a vast amount of time-dependant data. As an example, a patient on a regimen of three injections of mixed insulin per day who records only the most basic diabetes management data, i.e., only insulin and glucose levels, will generate a personal log comprising 810 data items over a three month period. It is extremely difficult, if not impossible, for a physician to be able to review and assimilate all the clinical and therapeutic implications of this vast amount of data in any reasonable amount of time.

While the introduction of glucose meters with various memory functions has greatly simplified the data recording process and increased the reliability of stored data, the large amounts of recorded data have made the interpretation task complicated. Such glucose meters now make it possible for patients to maintain a scrupulous record of glucose readings and insulin dosage taken over a lengthy period of time. More importantly, it is also possible with present-day devices for patients to record other clinically relevant data such as diet and exercise factors, and life-style information. All such stored data can conveniently be transferred to a physician's office, preferably via a communications link such as an acoustic modem line, where it can be reviewed in printed or video display format for making appropriate treatment recommendations.

The vast amount of stored glucose monitoring-related data has tremendously complicated the physician's ability to effectively study data corresponding to hundreds of time-dependant observations and measurements in order to focus on key clinical implications buried therein and generate meaningful and intelligent diabetes treatment decisions. Accordingly, computer-based methods must be adopted for efficiently tackling the high volume of monitored data and the complexity of the data interpretation task.

Attempts have been made at computerized automation of the data interpretation task and personal computer programs have been developed for interactive display of diabetes patient data and creation of paper reports therefrom. Such programs are typically menu-driven microcomputer programs which are adapted to process pre-recorded diabetes patient data in order to generate a statistical and graphical analysis of the data. Although the processing of voluminous diabetes patient data and the generation of associated graphs and statistical analyses does assist the physician in his review, it still becomes incumbent on the physician to spend a significant amount of time interactively guiding the analysis, studying the generated program results and performing additional synthesis of the data in order to detect clinical implications contained therein.

In essence, traditional approaches to automated analysis of diabetes data provide a relatively superficial analysis and an assortment of graphical displays based upon certain predefined statistical calculations. However, the time-consuming and complicated synthesis and interpretation of clinical implications associated with the processed data still need to be performed by the reviewing physician, and significant interaction is still required on behalf of the physician.

SUMMARY OF THE INVENTION

In view of the foregoing, it is a primary object of this invention to provide a system for automated analysis and interpretation of diabetes patient recorded data which is capable of identifying and highlighting key clinical findings from a patient's self-recorded data.

A particular object of the present invention is to provide such a diabetes data interpretation system which is particularly adapted for rapid, in-depth analysis of data from glucose meters.

A related object of this invention is to provide a data interpretation system of the above type which is capable of detecting clinical implications contained within the self-recorded data and presenting pertinent identified data in a manner that effectively supports the findings.

A more specific object of this invention is to provide such a diabetes data interpretation system which is capable of detecting significant changes in insulin therapy and determining any corresponding statistically significant and clinically significant changes in glucose control resulting from the changes in insulin therapy.

Briefly, in accordance with the present invention, the above and other objects are realized by means of an automated diabetes data interpretation system, referred to herein as the "IDDI" system, which combines symbolic and numeric computing approaches in order to identify and highlight key clinical findings in the patient's self-recorded diabetes data. The patient data, including blood glucose levels and insulin dosage levels, and associated lifestyle markers such as exercise, diet, symptoms, etc., recorded by a diabetic patient over a period of time by means of a glucose meter or the like, is initially downloaded into a central processing system such as a personal computer. The accepted diabetes data is subsequently processed to (a) identify insulin dosage regimens corresponding to predefined significant changes in insulin dosage which are found to be sustained for at least a predefined segment of the overall data collection period, (b) identify statistically significant changes in blood glucose levels resulting across adjacent ones of the identified insulin regimen periods, and (c) identify clinically significant changes in blood glucose levels from within the identified statistically significant glucose level changes.

The term "clinical" is defined as "pertaining to or founded on actual observation and treatment of patients, as distinguished from theoretical or basic sciences." "Statistical" is defined as relating to "a distinct scientific method that aims at solving real life problems by the use of a theory of probability; it usually deals with the collection, analysis and interpretation of numerical data, especially with methods for drawing inferences about characteristics of a population from examination of a random sample." See *Dorland's Illustrated Medical Dictionary*, 27th Ed., Harcourt Brace Johanovich, Inc., Phildelphia, Pa. (1988), pages 345 and 1578.

There is a clear dichotomy between a "clinically significant change" and a "statistically significant change", because a "clinically significant change" relates to whether the change is significant to the symptoms and treatment of a patient, whereas a "statistically significant change" is an inference about a change in the characteristics of a population drawn from examination of a random sample. A change an be "usually" or "statistically significant", yet need not be "clinically significant", so as to require any modifications of the patient's current diabetes management schedule.

The data processing of the present invention identifies changes that are "statistically significant" across adjacent ones of the identified insulin regimen periods. Therefore, samples are taken from the respective identified insulin regimen periods, and a "statistic" (such as the mean or standard variation) is computed for the respective samples as estimates of population parameters to be compared to determine whether changes in insulin dosage are statistically significant. Changes identified by a comparison of the statistical samples need not be clinically significant because a test for clinical significance requires domain dependent knowledge related to the symptoms and treatment of human patients.

The results of the diabetes data processing are generated in the form of a comprehensive yet easily understandable data interpretation report highlighting the processing results, including details pertaining to the identified insulin regimens and the associated clinically significant changes in glucose levels.

The IDDI system of the present invention is capable of rapid, yet in-depth analysis of patient data from glucose meters with memory functions so as to examine intermediate analytic results, study the clinical implications of the analysis, perform predefined data-driven analyses, and generate a cogent, self-contained output of key clinical findings. The system is capable of detecting clinical implications contained within the self-recorded diabetes data and presenting the pertinent data in a manner that effectively supports the findings.

In accordance with the system of this invention, the interpretation of diabetes patient data is accomplished by combining symbolic and numeric computing methods in order to derive clinically significant or meaningful findings from the self-recorded diabetes data. In essence, the system processes the patient's self-recorded data in accordance with specific symbolic and numeric analytic techniques to perform two important related tasks: (1) the detection of significant changes in a patient's insulin therapy, and (2) a determination of corresponding statistically significant as well as clinically significant changes in the patient's blood glucose levels resulting from the earlier-detected insulin therapy changes.

Changes in insulin therapy are inferred by examining the daily insulin dosages included in the patient's self-recorded data. Since patients frequently make small temporary adjustments in their insulin doses using a sliding scale based on a variety of factors (including the value of simultaneous blood glucose measurements, recent trends in glucose levels, and anticipated insulin needs), a change in the recorded insulin dose from a previous dose may represent changes resulting due to adherence to the sliding scale or, in fact, due to a true change in the patient's base line insulin therapy. The IDDI system is capable of recognizing when a systematic or significant change in insulin therapy (such as insulin type, dosage and number of shots) has occurred despite a background of constantly changing insulin information. Additionally, once a significant change in insulin therapy has been detected, the system further identifies if the modification resulted in any significant change in glucose control.

A plurality of algorithms are disclosed herein toward identification of insulin regimens, which are periods of similar insulin therapy from within the overall glucose data recording period. In accordance with a "robust-change-detection" ("RCD") algorithm, domain-independent changes are detected by identifying when a run of a predefined number or more of consecutive insulin readings are found to be different from the readings that immediately preceded the run. In accordance with a "local-relevance-aggregation" ("LRA") algorithm, adjacent daily insulin injection records are examined and an attempt is made to combine them into a set of related records, called a period. The combination is performed according to a sequence of diabetologist-derived combining criteria is used to determine if a daily insulin record can be included into a period.

Finally, according to a preferred embodiment, a "hierarchical-relevance" ("HR") algorithm is used which combines the advantages associated with both the RCD and LRA algorithms. The HR algorithm uses a hierarchy of "clinical significance" for determining which changes are of sufficient interest to cause a break in a run. The hierarchy encodes domain-dependent clinical knowledge similar to that used in the LRA algorithm and superimposes this knowledge on the domain-independent runs-detection method used in the RCD algorithm. A hierarchy of insulin changes is constructed for determining if a clinically significant alteration in insulin has occurred. This hierarchy is subsequently used to organize the criteria used to generate breaks in runs in applying the runs-detection method, and to create an appropriate insulin table.

When a significant change in insulin therapy has been detected, i.e., the overall data recording period has in fact been defined into several insulin regimens, the IDDI system initially determines whether the change in insulin therapy resulted in any statistically significant change in blood glucose control.

This is accomplished by performing a series of analysis of variance (ANOVA) tests on blood glucose readings separated by insulin regimens and mealtimes. (The use of "mealtimes" herein refers to the various time intervals of a day which, in the preferred embodiment, are breakfasttime, lunchtime, suppertime, bedtime, nighttime and overall.) The ANOVA test procedure is applied across adjacent regimens and pairs of corresponding groups of blood glucose readings in order to determine if the probability distribution of readings varies between compared groups, thereby indicating the presence of a statistically significant blood glucose change.

The ANOVA test is an example of a test for statistical significance. A test for statistical significance is a "test of significance" of the hypothesis of whether there has been a change in the probability distribution of the readings between the compared groups. In general, all possible results of the test are considered, and the possible results are divided into two classes: (1) the acceptance class, and (2) the rejection class, in such a way that the probability of obtaining a result in the rejection class when the hypothesis is true is equal to some small, pre-assigned value, alpha ($\alpha$), called the significance level. The test is then performed upon the specific readings. If the observed result lies in the acceptance class, the hypothesis is accepted as a satisfactory explanation of what has occurred (i.e., there has been a statistically significant change); if the observed result lies in the rejection class, the hypothesis is rejected an unsatisfactory (i.e., there has not been a statistically significant change). The level of significance denoted by alpha ($\alpha$) is often taken as 5% or 1%. See, for example, chapter 9, entitled "Tests of Significance" from Bulmer, *Principles of Statistics*, Dover Publications, Inc., New York, 1979, pp. 139-164.

The results of the statistical analysis are returned to the symbolic system which examines the statistical output for clinical relevance and generates an appropriate output if the statistical results are deemed to be of clinical import. In particular, the statistically significant changes are filtered in accordance with a set of screen rules based on clinical knowledge in order to identify clinically relevant blood glucose changes.

The system next determines the most relevant changes in insulin therapy associated with such clinically relevant changes in blood glucose. The system also identifies extremely high or extremely low readings based on predefined thresholds and generates explanations and characterizations for the same including details on the insulin intake most likely to have affected these extreme readings. Relevant details pertaining to blood glucose and insulin readings are indicated in the form of three-day plots including information for the day on which the extreme values occurred, as well as the immediately preceding and following days.

BRIEF DESCRIPTION OF THE DRAWINGS

Other objects and advantages of the present invention will become apparent upon reading the following detailed description and upon reference to the drawings in which:

FIG. 2 is an illustration of the introductory segment of the output report generated by the diabetes data interpretation system of the present invention;

FIG. 3 is a segment of the data interpretation report providing a summary of the insulin dosage (the insulin table) during the overall monitoring period when the patient's self-recording occurred;

FIG. 4 is a segment of the data interpretation report providing an overview of the self-monitored glucose measurements;

FIG. 5 is a segment of the data interpretation report providing an overall summary of blood glucose results during the self-monitoring period;

FIG. 9 is a segment of the data interpretation report providing a summary of blood glucose results in the identified insulin regimens for lunchtime readings;

FIG. 11 is a segment of the data interpretation report providing a summary of blood glucose results for the identified insulin regimens for supper readings;

FIGS. 15-19, 20A, 20B, 21, 21A, 21B, 22-28, 28A, 29, 29A, 29B, and 30 are flowcharts illustrating the sequence of operations involved in executing the IDDI system and generating the associated data interpretation reports.

Figure 1:
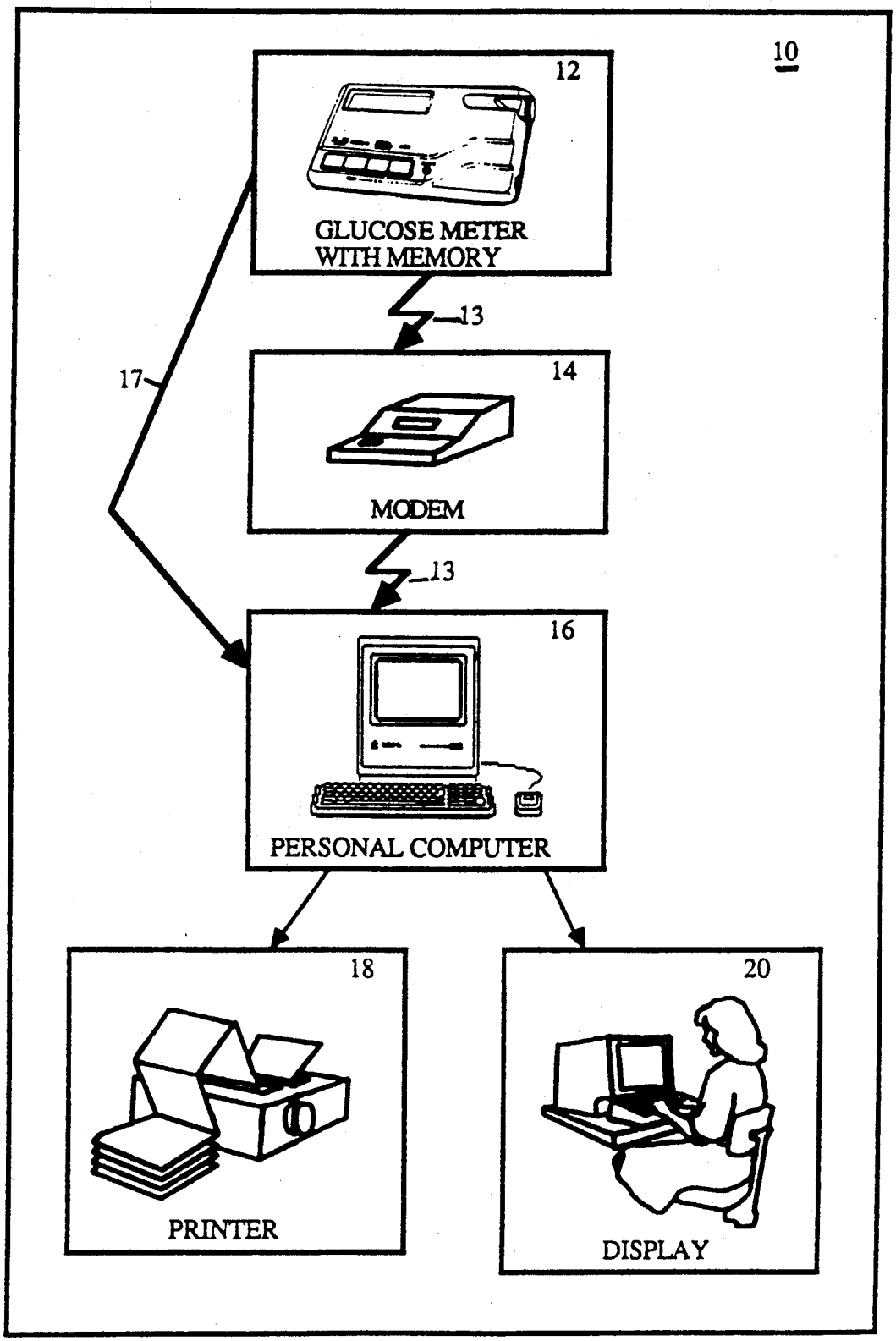
FIG. 1 is a block diagrammatic representation of the system hardware with which the IDDI system of the present invention may be used.

While the invention is susceptible to various modifications and alternative forms, a specific embodiment thereof has been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DESCRIPTION OF THE PREFERRED EMBODIMENTS

1. Overview of the IDDI System

Referring now to FIG. 1, there is shown a block diagrammatic representation of the system hardware with which the IDDI system of the present invention is adapted to be used. As shown therein, the system 10 essentially comprises the glucose meter 12 used by a patient for recording, inter alia, insulin dosage readings and measured blood glucose ("BG") levels, and possible lifestyle markers such as for diet, exercise, symptoms, etc., during a given monitoring period. Data stored within the glucose meter 12 is preferably transferred through appropriate communication links 13 and an associated data modem 14 to a processing station, such as a personal computer 16. Alternatively, data stored within the glucose meter 12 may be directly downloaded into the personal computer 16 through an appropriate interface cable 17.

The computer 16 includes the software necessary to process, analyze and interpret the self-recorded diabetes patient data in accordance with predefined flow sequences (to be described below in detail) and generate an appropriate data interpretation output. Preferably, the results of the data analysis and interpretation performed upon the stored patient data by the computer 16 are displayed in the form of a paper report generated through a printer 18 associated with the personal computer 16. Alternatively, the results of the data interpretation procedure may be directly displayed on a video display unit 20 associated with the computer 16.

A given patient data file, which comprises the data downloaded from the glucose meter 12 into the personal computer 16 and corresponding to a single monitoring period, is processed by the computer 16 in accordance with the IDDI system in such a manner as to extract clinically meaningful information therefrom and present it in the form of a comprehensive and informative report. The report is particularly adapted for convenient use by a physician toward arriving at meaningful or intelligent clinical and/or therapeutic decisions. The data interpretation report is comprehensive and replaces the laborious paging through and manual review by a physician of the inordinately large and difficult to comprehend amount of raw data contained in the patient log. It should be noted that the IDDI system requires no user intervention once the set of data to be interpreted is made available in the form of a patient file in system memory.

The system uses a combination of symbolic and numerical methods to analyze the data, detect clinical implications contained in the data and present the pertinent information in the form of a graphics-based data interpretation report. The symbolic methods used by the IDDI system encode the logical methodology used by expert diabetologists as they examine patient logs for clinically-significant findings, while the numeric or statistical methods test the patient data for evidence to support a hypothesis posited by the symbolic methods which may be of assistance to a reviewing physician.

The combined use of symbolic and numeric computing techniques in interpreting the patient's self-recorded data is essentially directed to the realization of two basic objectives:

(1) the detection of significant changes in insulin therapy so as to divide the overall monitoring period into a plurality of insulin regimens of similar insulin therapy, such as type of insulin (regular or short-acting insulin, NPH/lente or intermediate-acting insulin, and ultralente or long-acting insulin), dosage, number of shots, etc., and (2) detecting statistically significant as well as clinically significant changes in blood glucose levels following a detected significant change in insulin therapy.

Since the IDDI system does not have access to a patient's actual insulin regimen, it is important for the system to infer the patient's regimen, i.e., actual changes in insulin therapy, by examining the daily insulin dosages recorded in the patient's data and subsequently transferred to the corresponding patient data file in the system memory. Patients frequently make small temporary adjustments in their insulin doses using a sliding scale table based on a variety of factors, including the value of simultaneous blood glucose measurements, recent trends in glucose levels, and anticipated insulin needs. It is thus, important to distinguish between changes in the recorded insulin dose from a previous dose resulting (1) from adherence to the sliding scale or (2) resulting from a true change in the patient's base line insulin therapy. The IDDI system of the present invention is capable of recognizing the occurrence of a systematic change in insulin despite the background of constantly changing insulin dosages.

The identification of insulin regimens or periods of similar insulin therapy is important and allows data obtained during periods of different insulin therapy to be examined separately. If this separate examination does not occur, treatment-related changes in glucose control or clinical complications may be missed or attributed to other possible causes.

Three different algorithms were developed and are disclosed herein for identification of regions of similar insulin therapy. In accordance with a first algorithm referred to as the "robust-change-detection" ("RCD") algorithm, domain-independent change is focused upon. This algorithm is based on the concept of a "generic-change" which is found to exist when a run of a predetermined number (preferably three) or more consecutive insulin readings are found to have a sustained difference from the readings that immediately preceded the run.

With this algorithm, for instance, the sequence of regular insulin injections, 6 6 6 7 6 6 6 7 8 6, is identified as a sustained run of 6 units of regular insulin. It should be noted that no break in the run occurs at either of the two 7 unit or the single 8 unit injections because these changes are not sustained over the predefined threshold of three successive readings. These three irregular readings (the two 7s and the single 8) are said to be unsustained deviations or anomalous values.

On the other hand, the sequence of regular insulin injections, 6 6 6 7 7 8 7 7 7, is broken up into two sequences, 6 6 6 and 7 7 8 7 7 7 because there is a sustained change to 7 units from the initial run of 6 units. In this case, the single injection of 8 units is considered to be an anomalous value within the run of 7 units.

It should also be noted that the RCD algorithm may be modified for encoding additional clinical knowledge. For instance, the choice of the number of consecutive readings that determine the start of a new run can be increased. The preferred threshold of three consecutive readings was selected after the performance of this algorithm was examined with respect to other run-length values. Also, different run-length criteria may be specified for different insulin types (regular or long-acting) or for various injection times (AM or PM).

In addition, the range of recorded readings that may be considered "identical" can also be adjusted. The algorithm could, for example, be adjusted to account for the fact that, due to sliding scale insulin adjustments, regular insulin tends to vary more than long-acting insulin. By incorporating this clinical knowledge, the RCD algorithm could be modified to consider changes of $\pm 1$ unit of regular insulin to be "identical" dosages. Preferably, however, "identical" values are defined to be numerically equal. Also, different range criteria ($\pm 1$ unit) could be used for different insulin types or for various injection types.

For patients adopting split/mixed regimens, the RCD algorithm is applied to all insulin types (short-acting, intermediate-acting and long-acting) at all injection times.

In accordance with a second algorithm for identifying insulin regimens of similar insulin therapy, the "local-relevance-aggregation" ("LRA") approach, adjacent daily insulin injection records are examined and attempts are made to combine them into a set of related records, called a period. A sequence of combining criteria is used by this algorithm to determine if a daily insulin record can be included into a period. According to criteria No. 1, records that differ by regular insulin only are combined. According to criteria No. 2, records that differ by NPH type of insulin only are combined. According to criteria No. 3, records that differ by lente type of insulin only are combined. According to criteria No. 4, records that differ by ultra-lente type of insulin only are combined. For each such criterion, adjacent days are combined into periods only if they differ by that criterion.

The combining criteria ensure that periods generated by combining adjacent days reflect periods of clinically similar insulin therapy and are derived from reviews of representative patient insulin records by expert diabetologists. In terms of the algorithm sequence, periods are initially created using the first criterion. Records that are not combined into periods at this step are examined by the second criterion and combined into periods if they do satisfy that criterion. Each set of remaining records is examined by subsequent combining criteria and is combined into periods if it satisfies the criterion. It should be noted that periods formed by previous criteria are not combined into periods formed by later criteria.

A specific day is included into a period only if the insulin readings for that day differ only by the current combining criterion. However, this difference may exist at any injection time (AM or PM). Any change in the number of insulin injections (for example, from single-injection therapy to multiple-injection therapy) always results in the start of a new period irrespective of the current combining criteria. For a specific insulin injection record, either a criterion will be satisfied, resulting in that day being included in a period, or the criterion will not be satisfied, leaving that day excluded from the current period. The excluded day is, however, considered for possible inclusion into a different period if it satisfies a later combining criterion. The final insulin table is the set of all periods formed by all the combining criteria.

In accordance with a preferred embodiment of the present invention, a third algorithm referred to as the "hierarchical-relevance" ("HR") algorithm is used for identifying regions of similar insulin therapy. This algorithm combines the advantages and avoids certain disadvantages inherent to the two previously-described algorithms. In particular, the HR algorithm takes advantage of the fact that the RCD algorithm can be improved by application of additional clinical knowledge that can eliminate clinically-irrelevant divisions, while the LRA algorithm can be improved by the use of a less stringent runs-breaking criterion which can eliminate many small groups.

The HR algorithm is based on the use of a hierarchy of "clinical relevance" that determines which changes are of sufficient interest to cause a break in a run. In particular, the hierarchy encodes domain-dependent clinical knowledge similar to that found in the LRA algorithm and superimposes it on the domain-independent runs-detection method used in the RCD algorithm. As an illustration, a change from single to split injection therapy is clinically more significant than a small change in the amount of regular insulin in the morning.

More specifically, the HR algorithm is based on a hierarchy of insulin changes that determines if a clinically significant alteration in insulin has occurred. The hierarchy is used to organize the criteria for generating breaks in runs in the RCD algorithm. Traversal of the hierarchy is arbitrarily stopped when an insulin table of a predetermined depth (preferably 2–6 lines long) is created. The insulin table includes a corresponding line for each identified region of similar insulin therapy. A patient record that fails on all criteria in the hierarchy (for example, a patient who never changes insulin dosages) is summarized in a one-line insulin table. An identified region of similar insulin therapy will be referred to as insulin regimen or period.

Figure 2A:
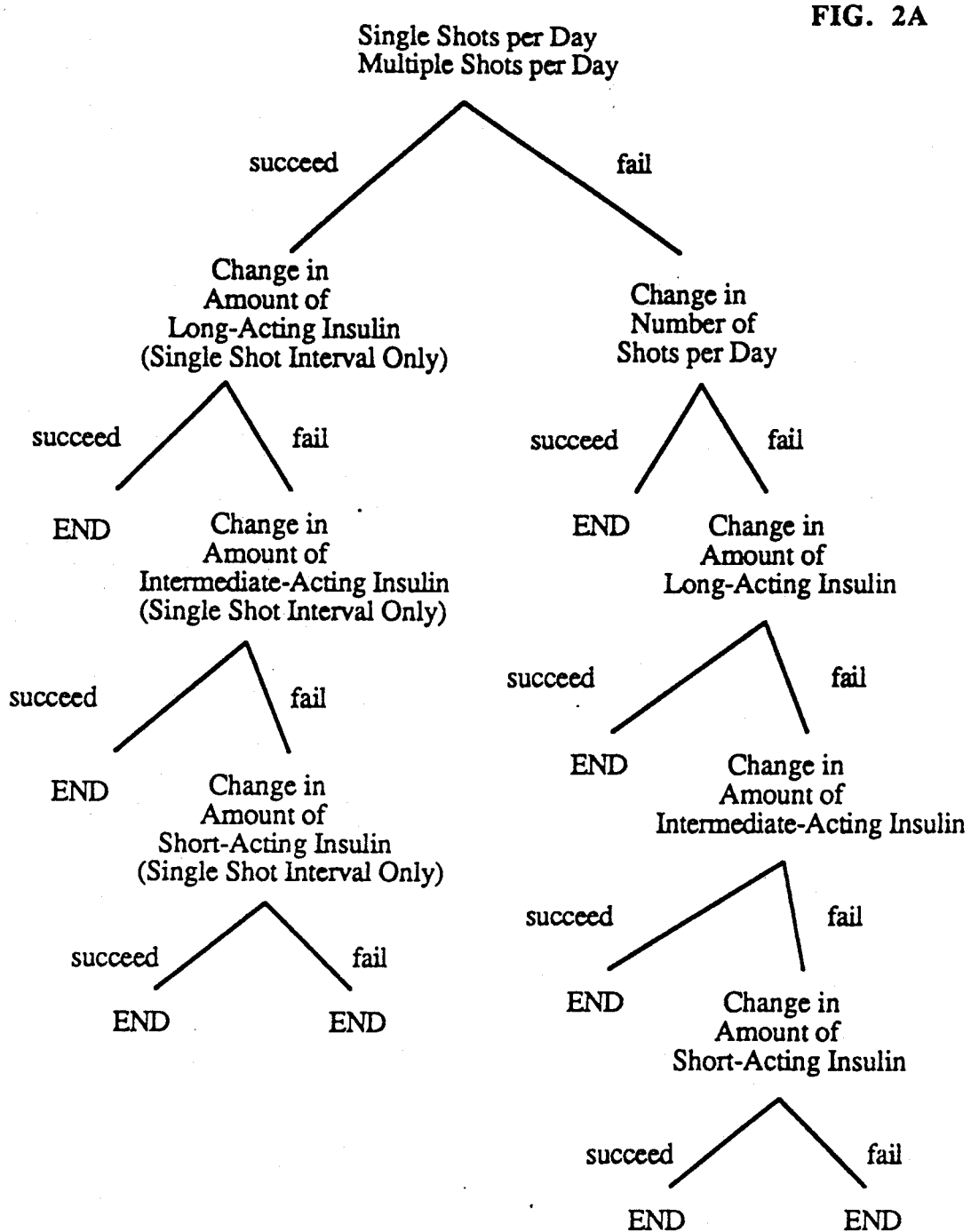
FIG. 2A is a binary tree illustrating the hierarchical structure used by the IDDI system for identifying significant changes in insulin therapy.

While the sequential procedure undergone in implementing the HR algorithm is described in detail below, the criteria encoded according to clinical knowledge, in accordance with a preferred embodiment of this invention, are illustrated at FIG. 2A in the form of nodes in a binary tree. The success branch at each binary node is taken if the result of applying a criterion to the patient record results in two or more runs; otherwise, the fail branch is taken. When an END node is reached, the insulin table is finalized of being printed later. Records which succeed on the first criteria (for instance, a change from single injection to multiple injection therapy) are processed additionally only during the single-injection intervals. If a patient's record fails on all criteria (i.e., reaches the rightmost END node), a one-line insulin table is finalized for being printed later.

In applying the binary tree hierarchy in FIG. 2A, the HR algorithm initially splits the insulin data based on the first criterion in the illustrated clinical heuristics hierarchy (i.e., splits the data if any sustained change from single to multiple injections of insulin per day is detected). For all criteria, a sustained change is defined as a difference that occurs in a predefined number or more of consecutive days. Preferably, the predefined threshold number of days for this purpose is selected to be three.

After the application of the first criterion, the number of runs detected by the criterion is counted. If there are less than two runs, the next criterion in the hierarchy is applied to the current run and the algorithm is repeated. If, however, there are at least two runs or if no other criteria exist, the insulin table generated up to that point is used directly.

Any time a significant change in insulin therapy is detected in accordance with the foregoing procedure, the IDDI system is capable of identifying if a change in insulin therapy resulted in, first, any statistically significant change and, subsequently, any clinically significant change in glucose control. Finally, the most relevant insulin changes associated with such clinically relevant glucose level changes are determined.

The above functions are accomplished by performing a series of analysis of variance (ANOVA) tests after separating the various blood glucose readings into different groups based on specific insulin regimens and time intervals of day (i.e., the mealtimes referred to earlier). ANOVA tests are performed for readings in adjacent regimens and pairs of such groups and determine if the probability distribution of blood glucose values has changed from the first group in a pair to the next, thereby indicating the presence of a statistically significant change in blood glucose readings.

Subsequently, a set of screen rules based on clinical knowledge is applied to identify those statistically significant changes in blood glucose readings which are also clinically significant. The IDDI system then determines, for each identified clinically significant change, the most relevant change in insulin therapy between the two regimens relative to which the significant change in blood glucose occurred. Accordingly, the system is capable of providing a possible explanation for each clinically significant change in glucose readings based on the corresponding change in insulin therapy, and the results of the analysis are presented in the form of an appropriate graphical display. For instance, if two adjacent insulin regimens differ in increases in both breakfast and lunchtime regular insulin dosages and a significant change in lunchtime glucose is found, the system identifies the increase in breakfast insulin dosage as the most relevant change. If, however, no significant changes in glucose readings are detected following the ANOVA tests, or if the subsequent screening identifies no clinically significant changes, no corresponding graphical display is generated in the data interpretation report. Further details about the identification of such statistically and clinically significant changes will be described below in connection with the IDDI system flowcharts.

The IDDI system also identifies the presence of readings which are either extremely high or extremely low, based on predefined thresholds. According to a preferred embodiment, readings exceeding about 375 mg/dl are classified as extremely high while readings below about 40 mg/dl are classified as extremely low. These extreme readings are further analyzed and explanations and characterizations generated on the basis of the particular insulin regimens and time intervals with which the readings are associated, as well as information on the type of insulin intake most likely to have affected the identified extremes. The results of this analysis are presented in the form of three-day plots including blood glucose and insulin details for the days immediately preceding and following the day on which each extreme value is found. Additional details about these procedures will be described below in connection with the corresponding IDDI flowcharts.

It should be noted that the expected change in glucose levels depends on the specific alterations in insulin therapy. Thus, the system focuses on changes in insulin therapy in order to explain potential changes in glucose control. For instance, if regular insulin is added to a patient's morning NPH insulin dose, generally lower lunchtime glucose readings can be expected.

Also, if the self-recorded patient data indicates that significantly more mid-day hypoglycemic episodes occurred while the patient received both morning NPH and regular insulin doses as compared to when the patient received only morning NPH, the IDDI system notes that the increase in complications, i.e., the occurrence of increased hypoglycemic episodes, is consistent with the change in morning regular insulin therapy. Although it cannot be proved that the addition of morning regular insulin resulted in the increase in hypoglycemic episodes, domain-specific knowledge about insulin kinetics and the temporal relationships seen in the patient record make this hypothesis clinically plausible.

The combined use of symbolic and numeric/statistical processing allows the coordination of the type of reasoning required to produce the requisite graphical output when a significant change in glucose control is associated with a change in insulin therapy. In particular, the HR algorithm generates the insulin table defining the various regimens of insulin therapy and uses symbolic methods. When a change in insulin therapy is detected, a statistical analysis is performed using the ANOVA routine. The ANOVA results are subsequently returned to the symbolic system, which examines the statistical output for clinical relevance.

Symbolic reasoning is also used to examine clinically relevant glucose changes and identify the most clinically relevant changes in insulin therapy associated with each such blood glucose change. Thus, symbolic and numeric processes are used in concert as the basis for the data analysis and interpretation task in order to present the results thereof in a clinically meaningful manner.

2. THE DATA INTERPRETATION REPORT

The following section provides a description of the data interpretation reports generated in accordance with the system of the present invention. These reports are particularly adapted for use by a physician as a replacement to sifting through patient log books containing a vast amount of raw data, the clinical and therapeutic implications of which cannot be assimilated in any reasonable amount of time. The report contains a number of graphs both simple and detailed, in order to help provide insight into the patient's level of glucose control and recording behavior. The graphs are also adapted to detail possible trouble spots or complications which can be inferred from analysis of the patient data.

Referring now to FIGS. 2-12, there are shown various segments of an illustrative data interpretation report generated by the IDDI system of the present invention following processing of a particular downloaded patient data set. It will be obvious that certain graphical sections in the illustrative report may not be generated for other patient data. Also, other data sets may generate additional segments similar to those shown here, as described in the system flowcharts.

FIG. 2 represents the "Global Summary" section of the IDDI report which provides a concise set of statements describing the highlights of the data interpretation results. In particular, the summary provides an examining physician with a very general summary of the patient data and gives an indication of areas on which the physician may focus in the subsequent sections of the report. In case of the patient data set for which the summary of FIG. 2 was generated, for instance, the first statement refers to what appear to be different regimens of insulin therapy. In each regimen, the system has identified a change in the pattern of insulin dosage. The changes from one regimen to the next may be relatively inconspicuous, such as the change in the amount of a particular type of insulin (long- or short-acting) taken at a certain time of day, or the changes may be more marked, such as a change in the number of insulin shots per day. The actual details of the different insulin regimens referred to in the summary are provided in subsequent sections of the data interpretation report.

The Global Summary also includes a reference to the relative status of the average blood glucose level for the patient compared to the upper or lower limits of the patient's prescribed target range. In addition, reference is made to the existence of blood glucose values exceeding predefined "extremely high" or "extremely low"

thresholds as well as a statement of the time interval when such extreme values occurred.

FIG. 3 provides an illustration of the "Insulin Dose Summary" section of the data interpretation report showing the differing insulin dosage during each insulin regimen identified in the patient's record. If no change in insulin therapy were to be detected, the insulin table shown in FIG. 3 would constitute a single line. The left-hand graph in FIG. 3, which is disposed under the heading "Insulin Period," identifies the various insulin regimens (labelled as A, B, C, etc.) and indicates what proportion of the entire patient recording period that particular insulin regimen comprises. This section of the graph shows the start and end dates of each regimen.

The gray level of the horizontal bar section for each regimen represents the percentage of days spanning that regimen in which insulin doses were recorded. Accordingly, a regimen in which all days contain insulin information is represented in black, while one in which most days have recordings is dark gray, and so on. While the short insulin regimens (1- and 2-day periods) are not shown in detail in the summary of FIG. 3, this particular graph is useful in showing where such periods appear relative to the rest of the record.

In the graph of FIG. 3, the column graphs on the right hand side (under the headings Breakfast, Lunch and Supper) show the relative frequencies of the actual doses of insulin taken at each mealtime during each insulin regimen. The gray level of each column in these graphs is representative of the particular type of insulin taken by the patient. Regular insulin is represented as light gray, NPH or lente insulin is represented as being relatively darker, and ultra-lente insulin is represented as being the darkest.

The graphs for a particular type of insulin at a particular mealtime have the same horizontal scales to enable a quick vertical visual scan of these graphs for focusing upon the change in a particular type of insulin at a mealtime. In the graph of FIG. 3, for example, NPH dosage at breakfast is shown to have changed dramatically across the three regimens: in the first regimen, i.e., regimen A, the dosage was 26 units, in the second regimen, i.e., regimen B, it was 22 units, and in the third regimen, i.e., regimen C, the dosage was 16 units. Similarly, the graph makes it clear that regimens A and B had no regular insulin at breakfast, while in regimen C, regular insulin was taken at a level of 6 units about 90% of the time and a level of 4 units about 10% of the time.

Referring now to FIG. 4, there is shown a segment of the data interpretation report characterized as "Glucose Measurement Summary" which is aimed at providing the physician with an overall view of the patient's blood glucose control and recording behavior. Referring to the bottom-most section of the graph, the gray "checkerboard" section shows, for each day, the o times (breakfast "B", lunch "L", supper "S", bedtime "BT", and during the night or night-time "NT") when blood glucose values were recorded by the patient. From the record represented in FIG. 4, it can easily be noticed that the patient began recording every day, four times a day (between 7/13 and 7/20), and subsequently switched to recording every other day (see periods 7/20-7/30 and 8/16-8/31). At a subsequent point in time, intermittent data recording was resumed (see period 10/7-10/21), followed by a long hiatus (see periods 11/3-12/1 and 12/13-12/29) when no readings were taken, followed by more regular recording again. It is also clear from this graph that on the days on which the patient was in fact recording, the recording was handled well by taking about four readings a day.

The upper section of the graph in FIG. 4 illustrates the daily blood glucose levels of the patient. The daily average and the highest and lowest recordings of each day are shown, with a bullet (•) indicating a weekday reading and a cross (x) indicating a weekend day reading. While individual readings for the day are not shown and, accordingly, the graph does not provide an indication of the time when the highest or lowest readings occurred, the daily range and average values provide adequate shows the patient's recommended therapeutic target range (indicated by the dotted lines) as well as blood glucose readings which fall outside the extremely high and extremely low thresholds (indicated by the dashed lines). As an aid to recognizing the presence of such extreme values, any time a reading beyond these extreme limits is found, this is indicated along the top of the graph by the presence of straight or inverted triangles, respectively representing extremely high and extremely low values.

The Glucose Measurement Summary also provides, at the thin section of the graph immediately above the glucose level section, the particular insulin regimen in effect at a given time. The advantage of the type of graph shown at FIG. 4 is that any other events recorded by the patient in addition to standard glucose/insulin headings, such as hypoglycemic symptoms (*), increase or decrease in diet (D+, D−) or insulin (I+, I−), or exercise (Ex), may conveniently be recorded along the top of the graph in conjunction with the extremely high and low values.

FIGS. 5-12 are segments of the data interpretation report which provide various summaries of the blood glucose results generated by analyzing and interpreting the patient's data file. In particular, FIG. 5 provides an overall summary of blood glucose (BG) results. The top section of the BG summary table indicates the level of control existing at each mealtime and highlights whether the average blood glucose was too high, too low, or within target range. This section also indicates whether or not the glucose readings varied substantially (i.e., are spread too wide), indicating the presence of poor glycemic control.

The bottom section of the BG summary table is detailed and addresses therapeutic issues related to the BG results. The first row of entries indicates the extent to which the average BG readings were beyond the target range (if at all) and also indicates the particular mealtime which appears to be most problematic. Here, for instance, the Supper "distance from goal" reading is identified as being problematic and is boxed for easy identification.

If the average BG level is found to be higher than the upper limit of the patient's therapeutic target range, it is likely that the examining physician will attempt to adjust the patient's prescription (insulin, diet or exercise) to bring the BG average to within target. This adjustment, however, is not always straightforward and the bottom section of the table on FIG. 5 provides information which can be of assistance to the physician in making appropriate adjustments. For instance, if a significant number of hypoglycemic readings have been recorded at the problematic mealtime, this is pointed out in the graph since lowering the average BG is also likely to increase the number of hypoglycemic readings. In this regard, a significant number of hypoglycemic readings is deemed to exist if more than a threshold percentage, preferably 8%, of the total readings for that mealtime are found to be hypoglycemic.

If, on the other hand, the problematic mealtime does not include any hypoglycemic recordings, but a number of readings exist which are sufficiently low that decreasing them by the amount that the average should be decreased by would bring them into the hypoglycemic range, then these values are potentially hypoglycemic. This fact is important to the reviewing physician and is identified and listed in the bottom section of the table.

Figure 6:
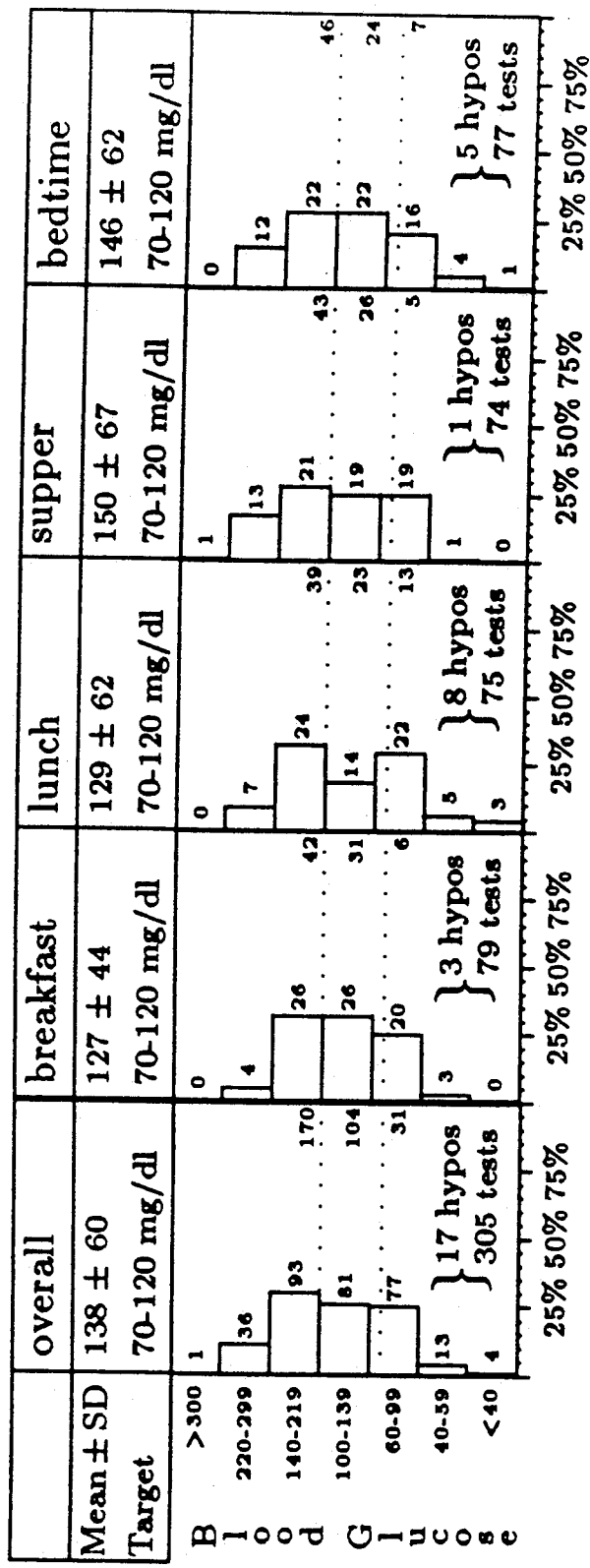
FIG. 6 is a segment of the data interpretation report providing a summary of the blood glucose results by patient mealtimes.

FIG. 6 represents a section of the data interpretation report which is referred to as "BG by Mealtime" and shows the distribution of BG values by mealtime, indicating the Mean and Standard Deviation, the target range, the number of BG readings above, within and below target range, and the number of hypoglycemic readings. The histograms for each mealtime show, for each range of BG values, both the relative frequencies (percentages marked along the horizontal axis) as well as absolute frequencies (numbers marked at the end of each bar). This type of graph is particularly advantageous in that any marked difference in control between mealtimes is made obvious.

Figure 7:
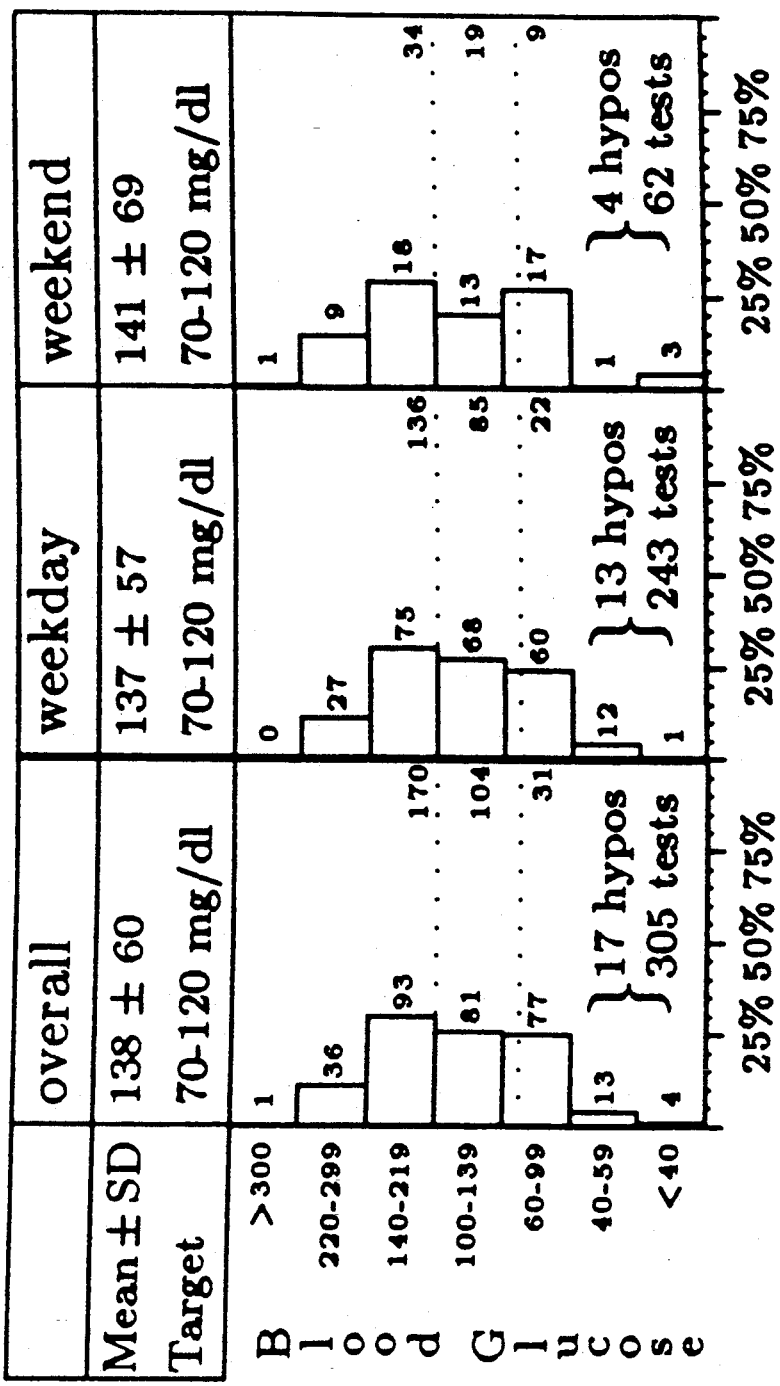
FIG. 7 is a segment of the data interpretation report providing a comparison of blood glucose results in weekdays versus weekends days.

FIG. 7 shows a segment of the data interpretation report identified as "BG by Weekday v. Weekend" and shows the distribution of BG control on weekdays versus, weekend days. The format of the graph in FIG. 7 is identical to that described above in connection with FIG. 6. The graph in FIG. 7 identifies increases in BG levels possibly resulting from the patient over-indulging with respect to food intake over weekends.

Figure 8:
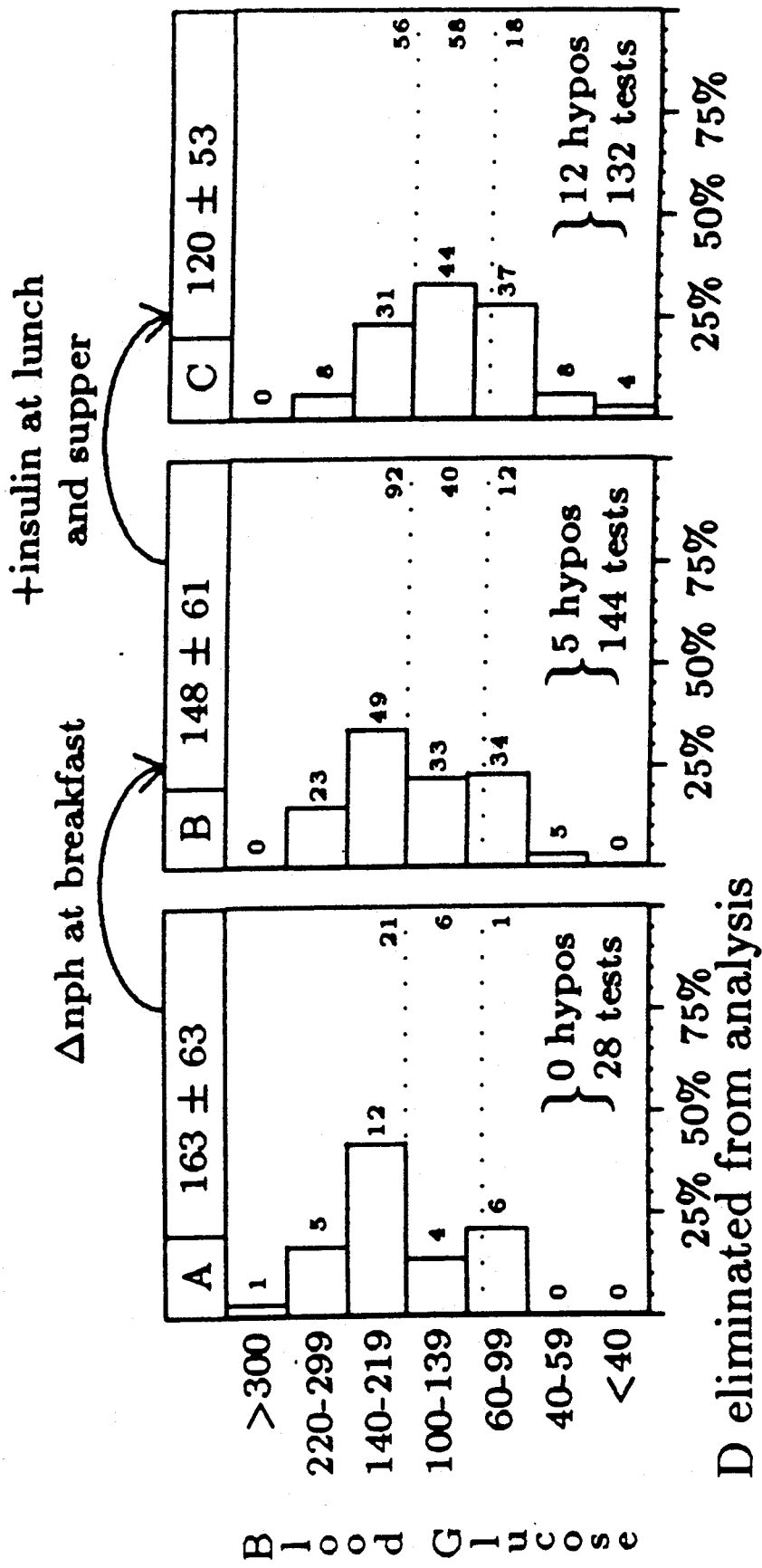
FIG. 8 is a segment of the data interpretation report providing an overall statistical summary of blood glucose results with respect to the identified insulin regimens.

FIG. 8 is a graph of the data interpretation report indicating the presence of any clinically significant effect of an identified change in insulin regimens on the overall level of BG control. Each histogram in the graph of FIG. 8 shows the BG information for corresponding insulin regimens associated with a clinically significant change, with the most relevant change in insulin regimen being marked along the curved lines headed by arrows. For example, the indicator "NPH at breakfast" indicates that the amount of NPH insulin changed at breakfast from one regimen to the next, and the indicator "+insulin at lunch and supper" indicates that an additional shot of insulin was added at lunch and supper. It should be noted that the graph shown in FIG. 8 would be absent from the data interpretation report if only a single insulin regimen were found to exist or if the change in therapy had no clinically significant effect on the level of glucose in the "overall" time interval.

Figure 10:
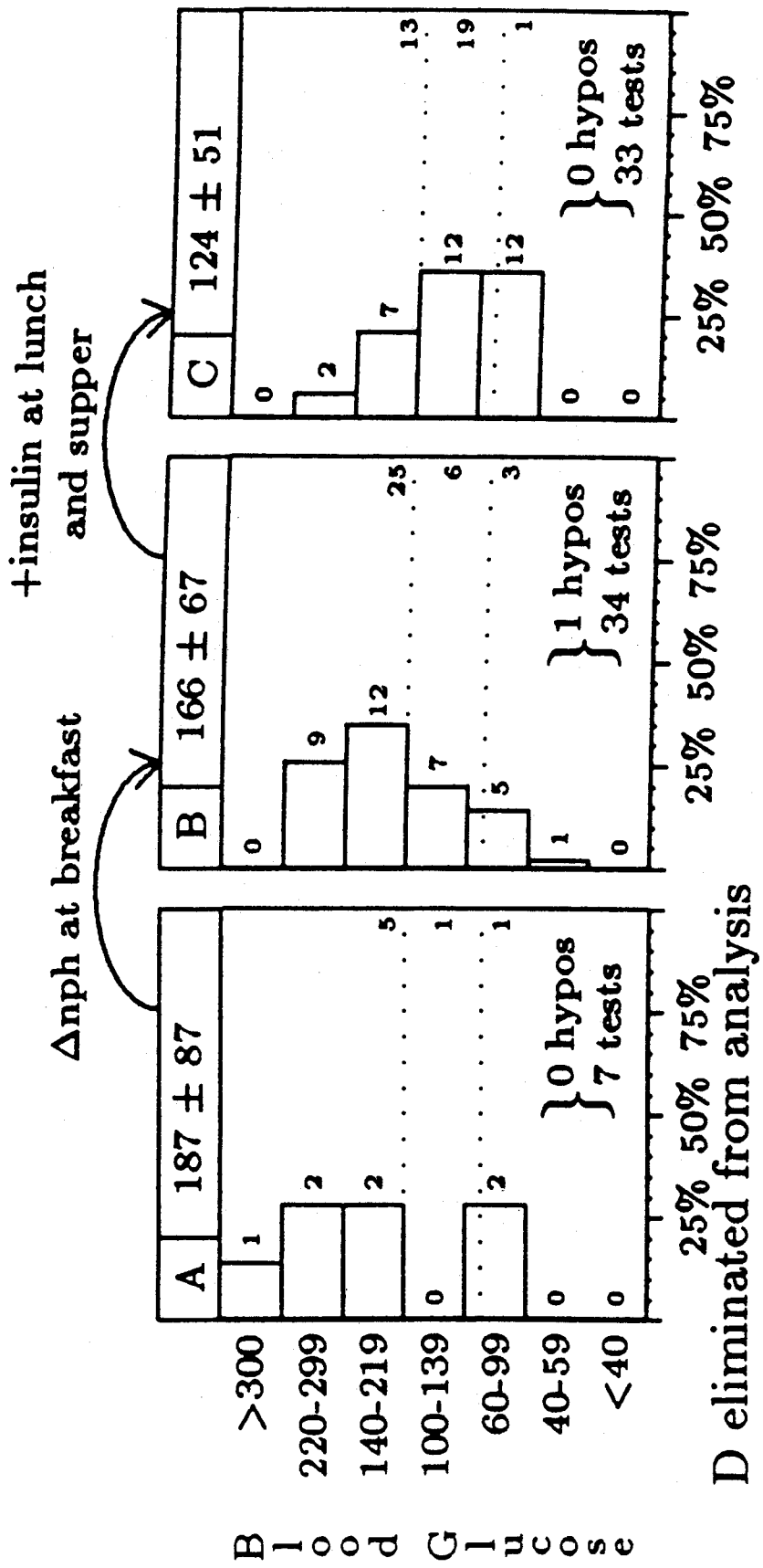
FIG. 10 is a segment of the data interpretation report providing a summary of blood glucose results for the identified insulin regimens for supper readings.

FIGS. 9-11 represent graphs similar to that shown and described in connection with FIG. 8. The graphs focus on clinically significant effects on the level of BG control during lunch, supper, and bedtime, respectively. Again, if no clinically significant changes exist in these time intervals, the graphs of FIGS. 9-11 would be absent from the data interpretation report.

Figure 12:
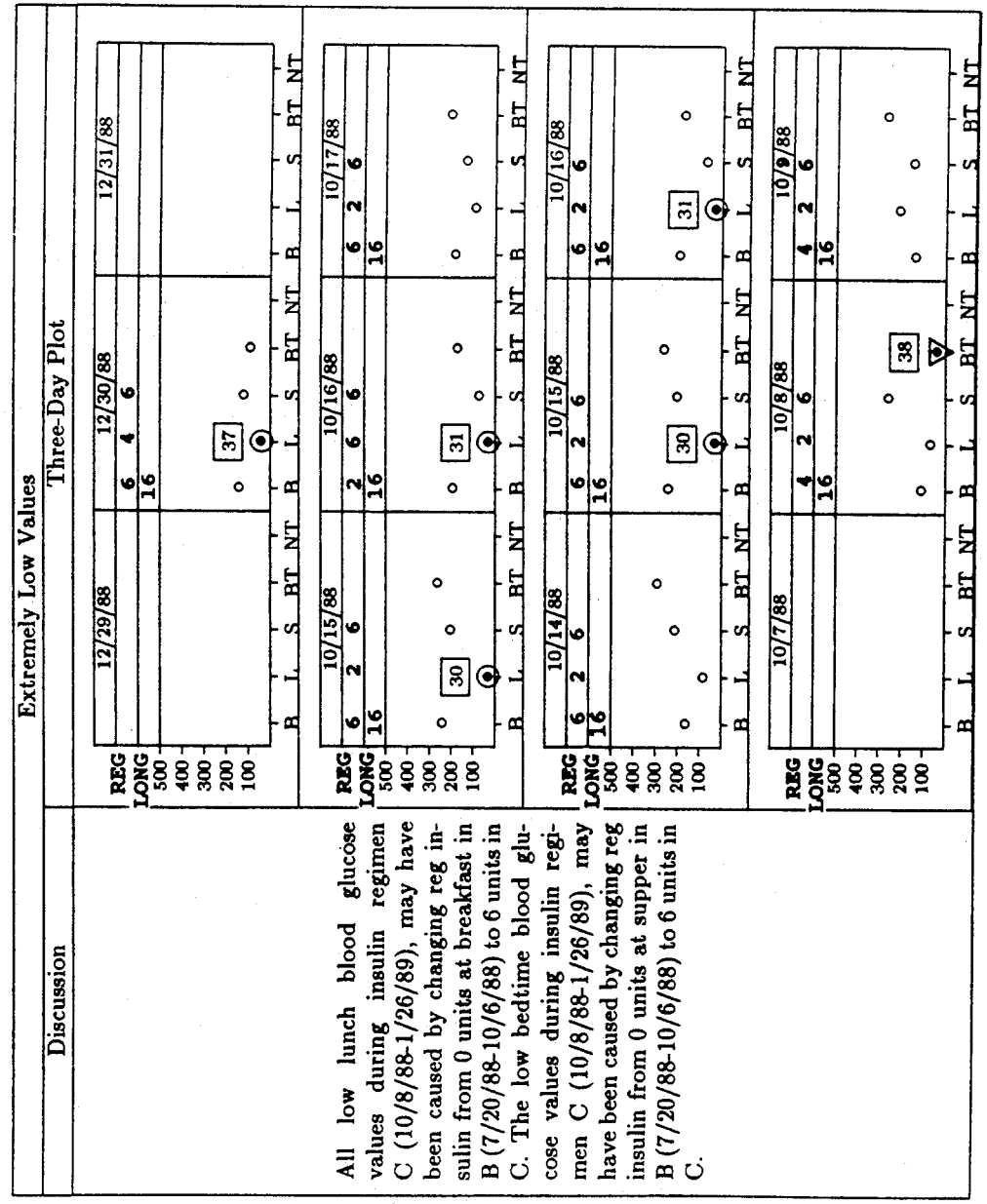
FIG. 12 is a segment of the data interpretation report showing 3-day plots for identified extreme glucose values and associated discussions.

Referring now to FIG. 12, there is shown a segment of the data interpretation report entitled "Extreme Values" which shows all BG readings and insulin injections for days on which an extremely high or extremely low blood glucose value is found to exist. These details are presented in the form of three-day plots which include BG and insulin details for the days immediately preceding and following the day on which the extreme values were found. The extreme values are indicated by bullets (as compared to the use of open circles for representing standard BG value) and are further enclosed by a box, circle, diamond, inverted triangle or upright triangle depending on whether the mealtime at which they occurred was breakfast, lunch, supper, bedtime or nighttime, respectively.

In addition, the left-hand column in the graph of FIG. 12 contains an explanation or characterization of these extreme values, if one is found to exist. As shown, an explanation typically contains information about an unusual insulin dosage that may be responsible for a particular extreme value, whereas a characterization describes some common attribute of a group of extreme values, such as the fact that all occurred during a particular insulin regimen or at a certain time interval of a day, or over weekends. By being adapted to identify and characterize such factors, the IDDI system according to this invention, thus, provides the reviewing physician with key clinical findings which can serve as important bases for therapeutic decision making.

3. Architecture of the IDDI System

The following section provides a description of the architecture of the IDDI system program.

Figure 13:
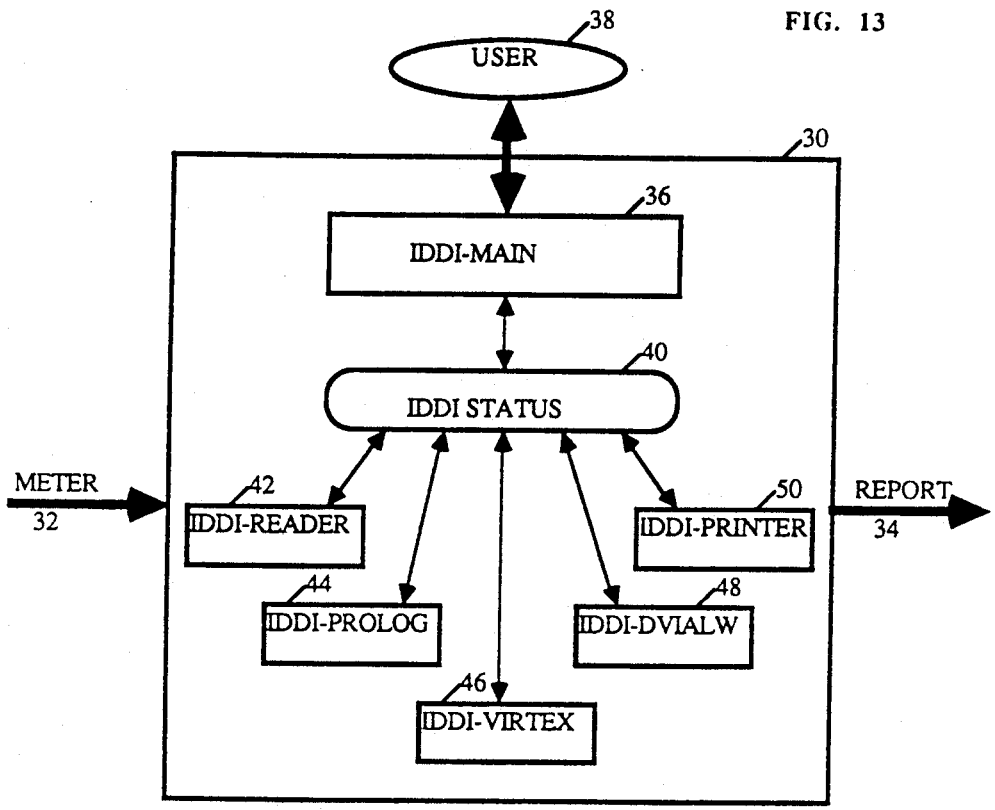
FIG. 13 is a block diagrammatic representation of hierarchical design of the system software for the IDDI system, in accordance with a preferred embodiment of the present invention.

FIG. 13 is a block diagrammatic representation of the hierarchical design of the program used for analysis and interpretation of diabetes patient data in accordance with the IDDI system of the present invention. As shown therein, the IDDI system 30 accepts patient diabetes data 32 from a glucose meter, stores the incoming data as a patient file within a database corresponding to various such patient files, processes the accepted and stored data using a main program and a plurality of associated subprograms in conjunction with a predefined range of user interaction, and generates a data interpretation report 34 highlighting various results of the data analysis and interpretation procedure.

The IDDI system program is designed around a simple program dispatcher or main program 36, referred to as IDDI-Main. The primary task of IDDI-Main is to execute a set of subprograms and to handle interaction with a user 38 as well as inter-program communications through a Status file 40, referred to as IDDI-Status. The Status file 40 has shared access by IDDI-Main and all subprograms associated therewith. As each subprogram is called and finishes its work, the program dispatcher in IDDI-Main checks for any errors that occurred in the subprogram and, if none is detected, calls the next subprogram. The names of the subprograms called by IDDI-Main are preferably declared in an ASCII configuration file in order to provide flexibility in program development.

According to a preferred system configuration, the subprograms called by IDDI-Main (and named in a corresponding configuration file) are IDDI-Reader 42, IDDI-Prolog 44, IDDI-VirTex 46, IDDI-DviALW 48, and IDDI-Printer 50. The operation of each of these subprograms 42-50 will be discussed in detail below.

In the IDDI system, all subprograms communicate information to each other via standard files that are created by one subprogram and read by the next subprogram. For example, IDDI-Reader reads or downloads information from a glucose meter, such as the Glucometer M+model glucose meter marketed by rights to the present invention, and creates a - data file (<patient-name>.meter). This data which creates a Tex file (<patient-name>.tex). The Tex file is, in turn, read by the subprogram IDDI-VirTex which creates a small Dvi file (<patient-name.dvi>). The Dvi file is then read by the subprogram IDDI-DviALW which creates a Postscript file (<patient-name>.dvi-alw).

The Postscript file is, in turn, read by the subprogram IDDI-Printer which spools the file to a Laser Writer (no output file) for being printed out. Details about these standard files created by the system subprograms will be described below.

In essence, the Main program launches the next program in the above-described program chain, in a manner akin to the one in which a batch file evokes a sequence of programs. IDDI-Main is informed when a subprogram completes its operation and if an error occurs during program execution. If an error has occurred, IDDI-Main stops further processing. If no errors occur, IDDI-Main launches the next subprogram.

The Status file 40 is used to perform communications between IDDI-Main and its associated subprograms. The Main program creates the Status file with global read/write permissions and all subprograms write into the status file only when they complete execution. Thus, the Main program is notified of the termination of a subtask when the Status file is not empty. Main reads the contents of the Status file, zeros out the Status file, and if no error has occurred, launches the next program. Subsequently, Main continues to read the Status file until it once again is not empty.

Each of the subprograms may place any information into the Status file although Main only examines the first byte. If that byte includes a letter (such as E) used to designate the presence of an error, Main assumes the occurrence of an error; otherwise, it is assumed that no error has occurred. It should be noted that because each program maintains its own log files, Main does not record any information about errors and the program terminates with an error dialog any time an error is detected. Under these conditions, no attempt is made to correct the error. Preferably, all log files from all subprograms are saved so that the source of errors generated may be analyzed.

Further, as each subprogram is launched by Main, a status dialog box created by the program is updated. This dialog box informs the user of the status of the IDDI system and is particularly helpful when a long data file is being processed.

Figure 14:
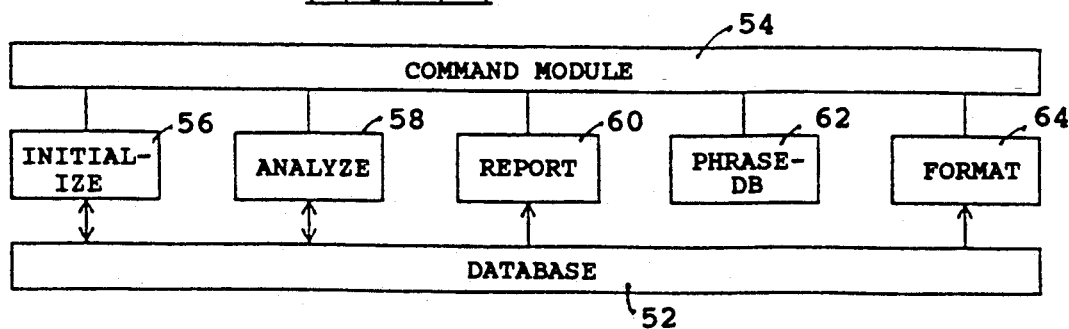
FIG. 14 is a block diagrammatic representation of the architecture for the major analysis module of the IDDI system.

Referring now to FIG. 14, there is shown a diagrammatic representation of the major module, i.e., IDDI-Prolog, of the IDDI program architecture, in accordance with the present invention. As shown therein, patient data which is loaded into a database 52 is analyzed and interpreted under control of a command module 54 using a plurality of modules performing predefined functions. More specifically, an Initialize module 56 is used for clearing the global data structure and creating the patient database 52 in a suitable form. Preferably, the form is such that each item has a unique identifying key and the keys for similar items are grouped such that they can all be retrieved via a single resolution. Techniques for accomplishing this type of database/file definition are well known in the art and, accordingly, are not described in detail herein. According to a preferred method of representation, the original data is in a file with an extension '.meter' which corresponds to data downloaded from a glucose meter, while the keyed and indexed data is in a file with an extension '.db'. The net result of the initialization procedure is to release data from previous runs, set global constants and load a .db database file.

An Analyze module 58 is used to examine the database and perform various data analyses, the results of which are also stored in the database. A Report module 60 uses the facts stored by the Analyze module 58 to generate a string of tokens which are fed through a Phrase-db module 62 into a Format module 64 which writes the report in an appropriate text form into a file which is ready to be processed for printing.

With particular reference to the Initialize module 56, it functions to erase data from previous runs and define and assert various constants as global variables. If no .db file corresponding to the given patient name is found to exist, it is an indication that the patient data is still in its original form and, accordingly, the corresponding downloaded .meter file is preprocessed and keyed. Each data record in the file is provided with a unique key and the key of the interval in which it resides. All days and all intervals within all days also get unique keys.

For example, in the case of a blood glucose record in the .meter file as listed below:

89 02 02 11 30 165 AA

The '.db' file would derive the following records:

bgc(bgc11,lunch4,dt(2/2/89,11:30),165)
kind(lunch4,lunch)
group(day4,[breakfast4, lunch4,
dinner3,bedtime4[])
day(day4,2/2/89)

It should be noted that the above patient record specified the measurement of a blood glucose level of 165 measured at 11:30 a.m. on Feb. 2, 1989. The digits at positions AA represent markers set up by the patient during monitoring and identify predefined information such as a designated pre- or post-mealtime reading, test reading, etc.

The new records set forth above are asserted to the global database along with additional information as to which groups of keys are related. For example, a record listing all breakfast blood glucose keys would be asserted as below:

group(breakfast, bgc, [bgc0, bgc4, bgc8, bgc12, bgc16]).

The Analyze module 58 is charged with the basic analysis of data stored within the database 52. The Analyze module 58 initially generates information corresponding to the overall blood glucose summary corresponding to the Glucose Measurement Summary illustrated at FIG. 4. This is accomplished by collecting information about blood glucose readings for each day and calculating the mean for the day, the highest and lowest values, whether or not the day contained an extremely high reading (defined according to a preferred embodiment to be over 375 mg/dl) or extremely low reading (defined according to a preferred embodiment to be under 40 mg/dl), and the number of readings taken and the mealtimes at which they occurred.

The Analyze module 58 subsequently summarizes the insulin dosage information in order to generate the Insulin Dose Summary illustrated at FIG. 3. The object of the summarization process is to realize an insulin table having a predefined depth, preferably a 2-6 line table, with each line describing a different insulin regimen. The insulin dose information is summarized because it is important to see whether or not the different insulin regimens had any positive effect on the patient's blood glucose values. The length of the insulin table is restricted to the 2-6 line depth because it becomes difficult for a physician to compare too many items and draw any useful conclusions from an overly long table. In addition, if too many regimens exist, the time they span becomes shorter and thus the number of data points (i.e., blood glucose readings) in each regimen also becomes smaller so that the outcomes of any statistical tests become less reliable.

Following the above-described summary, a more critical summary of blood glucose values is next performed by the Analyze module 58. More specifically, for each mealtime, the mean glucose level is found and compared with the target range for that mealtime. If the mean is too high, it is likely that the physician will look toward lowering it. If there are any hypoglycemic values for that mealtime, lowering the average blood glucose value will probably result in more hypoglycemic values; accordingly, it is important that this fact be highlighted, and the module does so. Even if no hypoglycemic readings are found, it is possible where the spread of readings is very wide that there may be readings sufficiently low so as to become hypoglycemic with an overall lowering of blood glucose levels for that mealtime; again, it is important that these "potentially hypoglycemic" readings be noted, and the module does so.

In addition, for each mealtime, the Analyze module 58 characterizes the blood glucose distribution as being consistent or inconsistent depending primarily upon the spread of the distribution. If the distribution for a mealtime is classified as inconsistent, further analysis is performed and the blood glucose readings are divided into groups such that all readings within a group fall in the same insulin period as determined by the insulin dosage summary. These groups of readings are then subjected to the statistical analysis of variance (ANOVA) tests which yield positive answers if the groups of blood glucose readings have different probability distributions. If any ANOVA test is positive, subsequent tests for clinical significance are applied. Further, in order to assist in explaining the change in blood glucose, each group of readings is characterized, the difference between the two relevant insulin regimens is noted, and the corresponding most relevant insulin change is determined.

In addition, for each such group of readings, the mean glucose level is found as well as the number of blood glucose readings above, below, and within the target range, the number of hypoglycemic readings, and the total number of readings in that group.

The Analyze module 58 further attempts to characterize any extremely high or extremely low readings and, for each reading, an attempt is made to identify an unusual insulin dose which may explain this extreme value. At this point, if an explanation has not been found for all high or low values, an attempt is made to characterize the group of high or low readings by insulin regimen, mealtime, and weekday vs. weekend classification. Preferably, in order to describe a group of extreme values according to one of these factors, say, insulin regimen, at least 0.6667 of the readings must belong to the same regimen. Where there is no grouping that applies to this threshold number for the group, an indication is provided that no explanation is available.

The Report module 60 generates a string of concept and control tokens which are used to generate the paper report. The concept tokens are IDDI-Prolog terms which are translated by the Phrase-db module while control tokens are used directly by the Format module 64 to generate graphs or tables. The operation of the Report module 60 consists primarily in the collection of the complex terms generated by the Analyze module 58.

The Phrase-db module 62 functions to process all relevant tokens with a threshold volume which is associated with each token and determines whether or not the token will be used to generate some output. Tokens not corresponding to this threshold volume are discarded. Further, in this module, concept tokens are translated into strings while control tokens are passed through unchanged with both kinds of tokens being stripped of their type (control or concept) before being passed to the Format module 64.

The Format module 64 receives a list of strings and IDDI-Prolog terms. The strings are directly written to an output file while the terms are processed individually to produce the output necessary to generate a requisite graph or table.

4. Logical Sequence of Operations

The following section provides a description of the logical flow sequences associated with the operation of the IDDI system of this invention.

Figure 15:
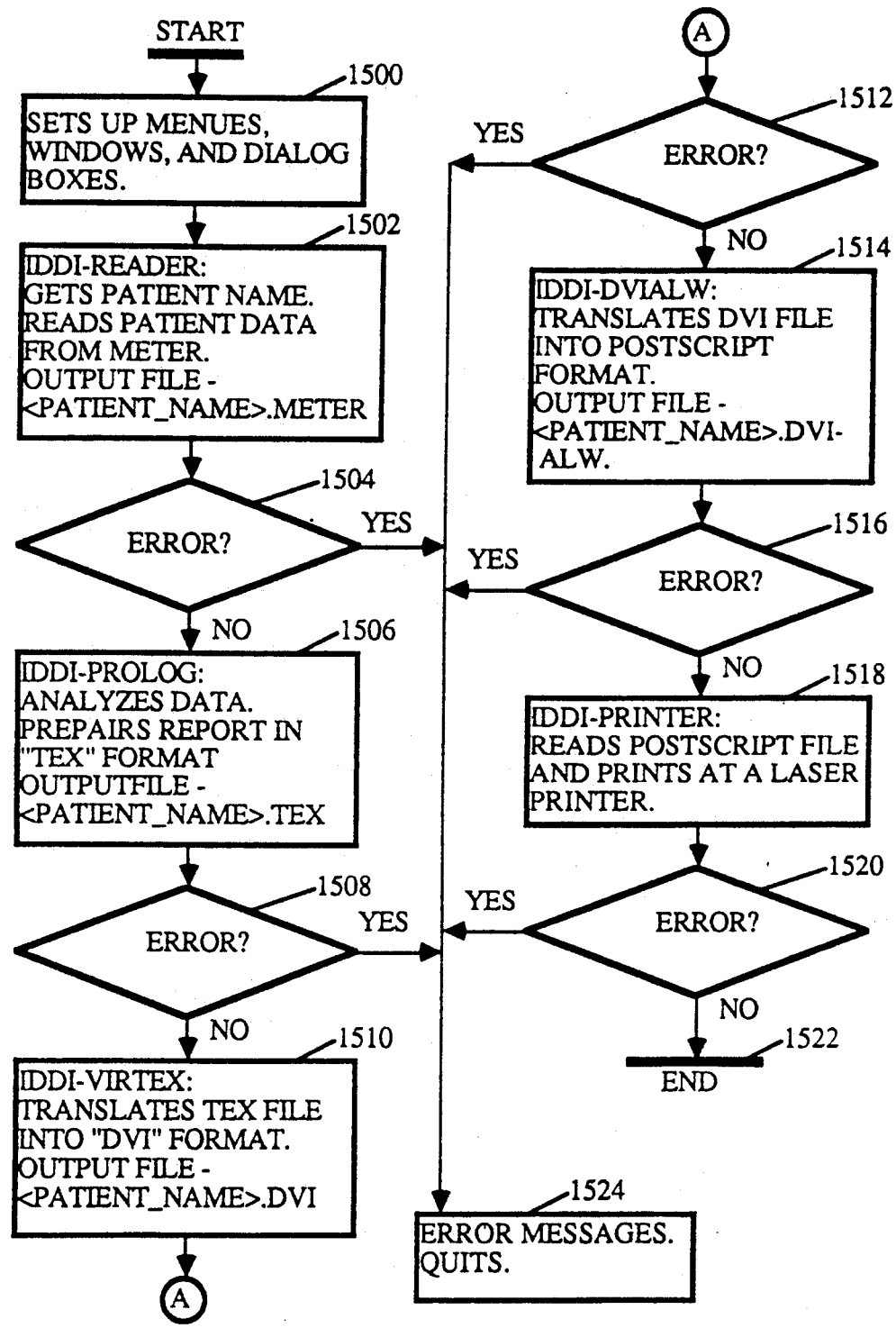

Referring now to FIG. 15, there is shown a flowchart providing an overview of the operational sequence for the IDDI system. Following start of the program, at step 1500, appropriate menus, windows and dialog boxes are set up for displaying the messages necessary for user interaction through the standard display and keyboard associated with the computer system on which the IDDI system is running.

The Main program calls the IDDI-Reader subprogram at step 1502. Reader essentially reads a glucose meter and creates a raw data file in a standard dump format. The subprogram obtains a patient name from the user, and the user is prompted to link the glucose meter into an input port (the RS-232 port) on the computer through an appropriate cable connection. Subsequently, data stored in the glucose meter is downloaded and dumped into a data subfolder that is named in the configuration file for the system. The patient name is also written into a mode file which is also named in the configuration file. All files, such as data file and log files, that are created by IDDI-Reader as well as by other subprograms use the patient's name that is obtained from the dialog box as the base file name. Thus, the output file created by IDDI-Reader from the meter has a format of the type <patient-name>.meter.

At step 1504, the program monitors the existence of an error which, at this junction, generally results during downloading of data from the glucose meter, possibly because of a loose connection in the interface cable or the like.

If no error is detected at step 1504, step 1506 is accessed where the Main program calls upon the subprogram IDDI-Prolog which constitutes the major data analysis section of the IDDI system. IDDI-Prolog essentially analyzes and interprets data existing in the patient output file in accordance with the fundamental architecture discussed in connection with FIG. 14. The action of the IDDI-Prolog subprogram generates both screen and file output, the primary value of the screen output being to track progress of the program. The output file is an ASCII file referenced by the patient name and generated in a language which is particularly adapted for optimum printing of text and graphs together. Preferably, the report generated by IDDI-Prolog is written in the TEX typesetting program which is in the public domain, as noted below.

Subsequently, at step 1508, an error check is made and if no error is found to exist, step 1510 is accessed where the Main program calls the IDDI-VirTex subprogram. IDDI-VirTex essentially functions to translate the TEX file created at step 1506 into a device-independent (Dvi) format in order that the graphics format contained within the file be portable across different device configurations.

The IDDI-VirTex program is a modified version of the public domain document formatting program known as TEX and developed by Donald Knuth of Stanford University. The TEX source code for UNIX systems, written in the WEB language is in the public domain and is available for a nominal media distribution charge from the University of Washington in Seattle. A public domain program known as WEB2C and written by Tim Morgan of University of California, Irvine, is available for converting WEB code into machine-generated "C" code. It will be understood by those skilled in the art having the benefit of this disclosure that a working version of TEX can be created from the WEB2C output, and IDDI-VirTex is merely an adaptation of the WEB2C output as a port for the Apple-Macintosh ® family of computers. Accordingly, program details regarding this and other standard adaptions of public domain programs are not disclosed herein.

Next, at step 1512, a check is made to see if any error resulted from the IDDI-VirTex translation sequence. If no error is found, step 1514 is accessed where the Main program calls the subprogram IDDI-DviALW for translating the Dvi file created by VirTex into a format, such as the well-known POSTSCRIPT format, which is capable of being understood by a laser printer. It should be noted that the DviALW is a public domain Dvi-to-POSTSCRIPT translator written by Nelson Beebe at the University of Utah, and comprises one of a large number of Dvi translators. This public domain program is modified, according to well-known porting techniques, for being adapted for use with the Macintosh ® line of computers.

At step 1516, an error check is made with respect to the translation performed at step 1514 and, if no error is found to exist, the Main program calls the IDDI-Printer subprogram which essentially functions to read the POSTSCRIPT file and spool it for printing at a laser printer associated with the system computer. While other implementations will be obvious to those skilled in the art, according to a preferred implementation, IDDI-Printer is particularly adapted for spooling to an Apple LaserWriter ® and is based on public domain code derived from a published article by Sak Wathanasin in the September, 1986 and January, 1988 issues of MacTutor magazine.

Subsequently, at step 1520, a check is made to identify any errors resulting in the spooling and printing process at step 1518 and, if no errors are found to exist, the program comes to an end at step 1522. If the error check at any of the previous check points is found to be positive, step 1524 is accessed and appropriate error messages are displayed to the user and the program quits.

Figure 16:
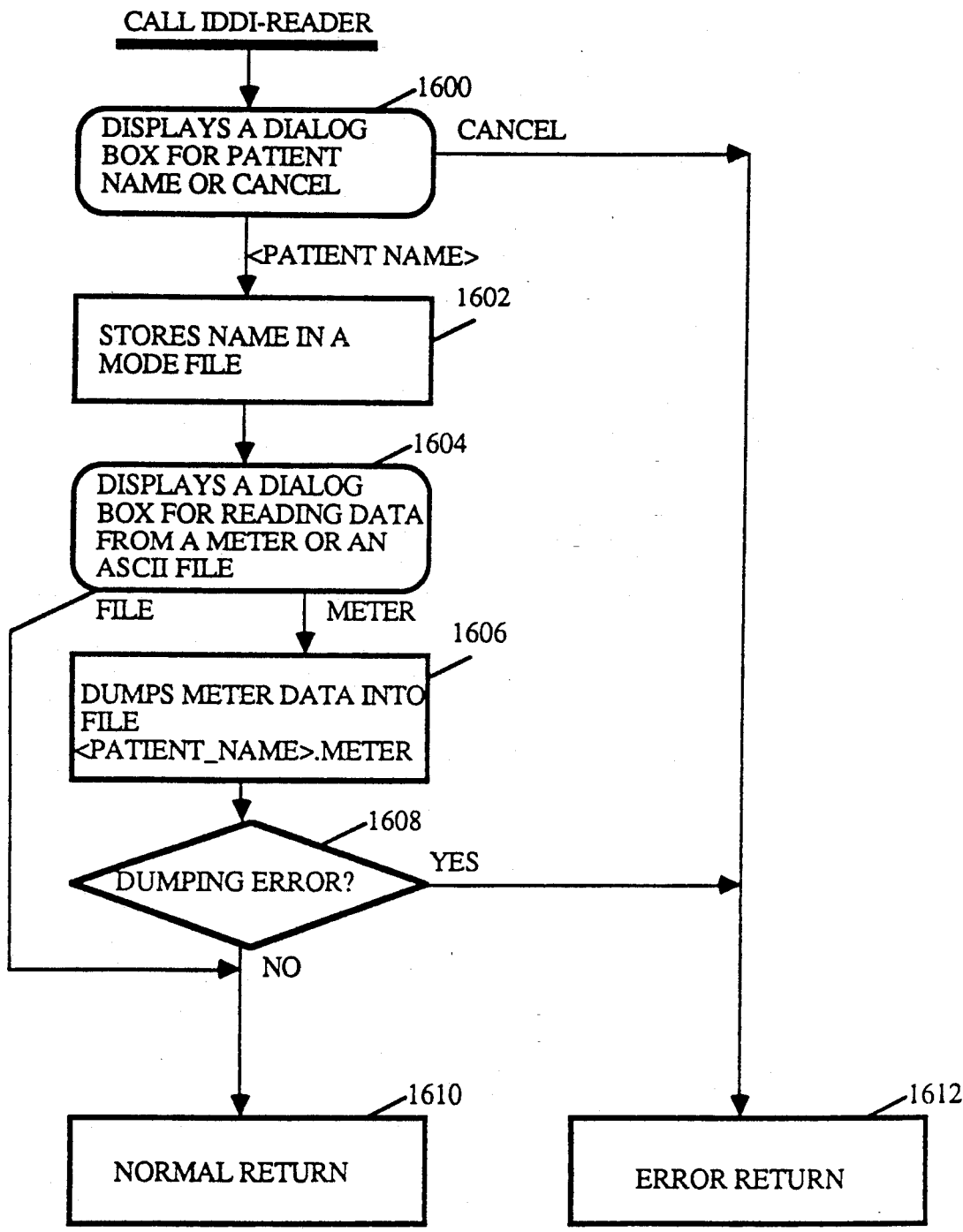

FIG. 16 is a flowchart illustrating the sequence of operations undergone by the IDDI-Reader subprogram. At step 1600, IDDI-Reader displays a dialog box for entry of a patient name by the user. Alternatively, the user is presented with the option of cancelling out of the subprogram. If the user opts to cancel, step 1612 is accessed where the program returns in an error mode. On the other hand, if the user provides a patient name for proceeding with the data analysis procedure, step 1602 is accessed where the patient name is stored in a mode file.

Subsequently, at step 1604, a dialog box is displayed for initiating the reading of data from a glucose meter or from an ASCII file already existing in the system database. If data is to be read from a glucose meter, step 1606 is accessed where a standard subroutine adapted to transfer data is called for dumping meter data into a file referenced by the input patient's name. Subsequently, a check is made at step 1608 for any dumping errors occurring in the downloading process at step 1606. If such an error is found, step 1612 is accessed and the program returns in error mode. Otherwise, step 1610 is accessed and the program returns in normal mode.

Figure 17:
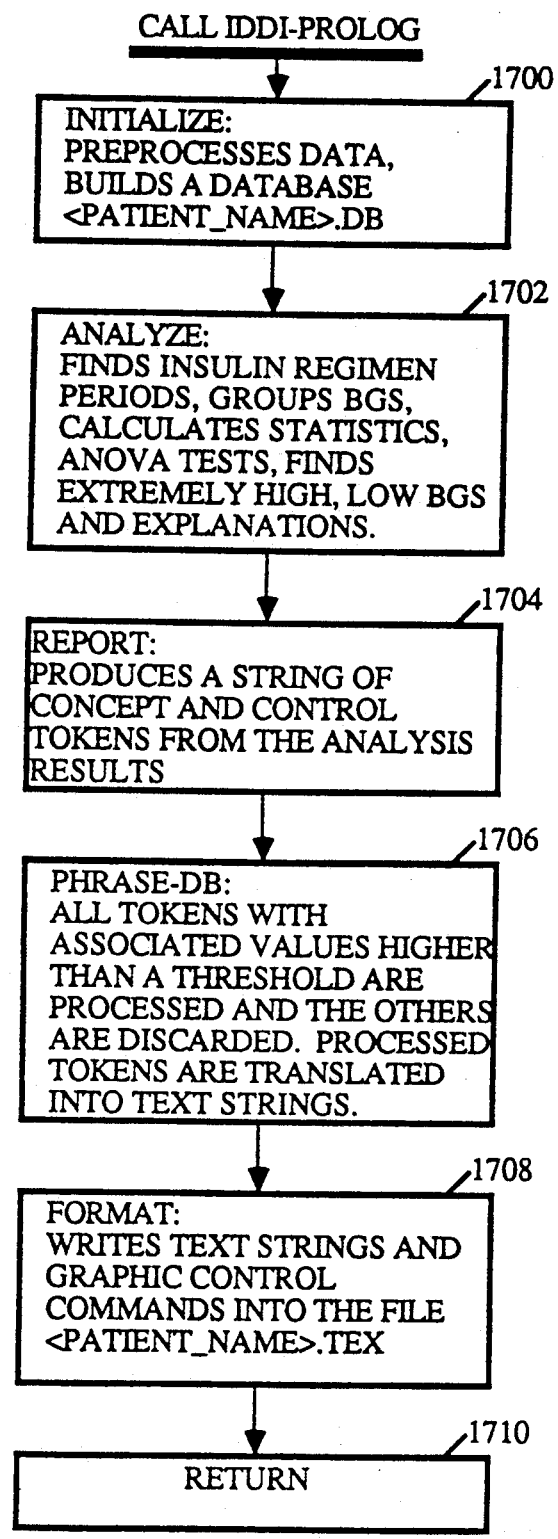

FIG. 17 is a flowchart illustrating the flow sequence associated with the IDDI-Prolog program. The IDDI-Prolog program first initializes and preprocesses data contained in the input file with which it is provided, and builds a database using this information. This is accomplished at step 1700 in accordance with the functional aspects described above in connection with the Initialize module in FIG. 14.

IDDI-Prolog is adapted to function with input files corresponding to a '.meter' extension and comprising files created by downloading a glucose meter.

Subsequently, at step 1702, the file created at step 1700 is analyzed in accordance with the procedure described above in connection with the Analyze module in FIG. 14. More specifically, the patient data is analyzed to determine insulin regimen periods, group blood glucose readings (BGs), perform requisite statistical calculations and the ANOVA tests, determine clinically significant changes in blood glucose and associated most relevant insulin changes, and find extremely high/low BGs and explanations associated therewith.

Subsequently, at step 1704, the functions described above in connection with the Report module in FIG. 14 are executed in order to produce a string of concept and control tokens from the results of the analysis at step 1702.

Next, at step 1706, the functions of the Phrase-db module in FIG. 14 are executed. More specifically, all tokens having associated values higher than a preset threshold are processed while the remaining tokens are discarded. In addition, the processed tokens are translated into text strings.

Subsequently, at step 1708, the functions of the Format module in FIG. 14 are executed whereby the text strings generated at step 1706 and related graphic control commands are written into an output file in the TEX format. Finally, at step 1710, the subprogram IDDI-Prolog returns to the Main program.

Figure 18:
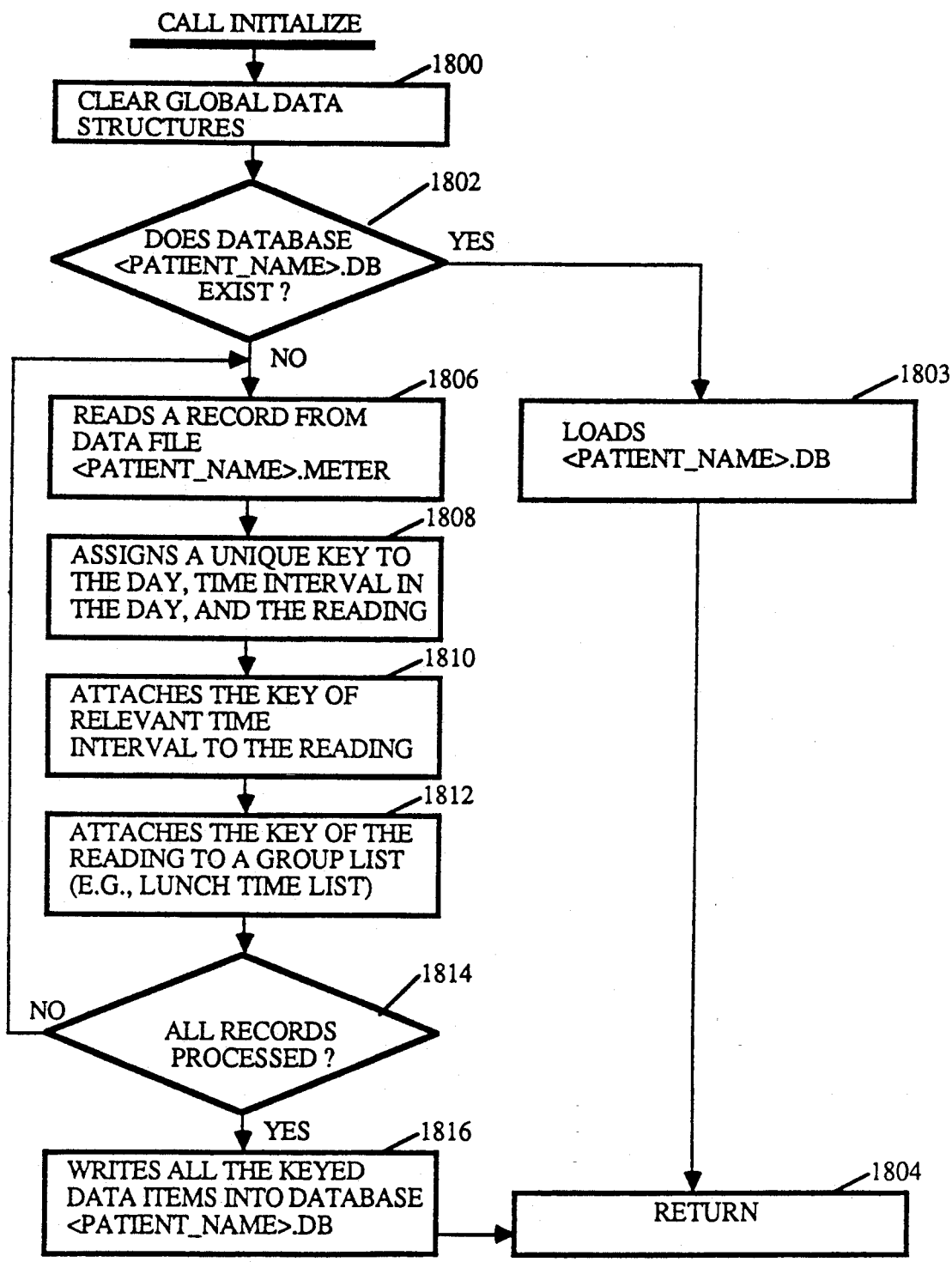

Referring now to FIG. 18, there is shown a flowchart highlighting the flow sequence involved in executing the functions of the Initialize module at step 1700 in FIG. 17. The Initialize module begins executing at step 1800 by clearing all global data structures. At step 1802, a determination is made as to whether or not a database file corresponding to the input patient name exists. If the answer is found to be positive, step 1803 is accessed where the corresponding .db file is loaded into main memory.

Next, step 1804 is accessed and control is returned to the IDDI-Prolog program. If the answer at step 1802 is negative, step 1806 is reached where the first record from the patient data file is read. At step 1808, a unique key is assigned to the day, the time interval in the day, and the reading corresponding to the record. At step 1810, the key of the time interval in which the reading exists is attached to the reading. Subsequently, at step 1812, the key of the reading is attached to a corresponding group list, such as a lunchtime list or a breakfasttime list.

Next, at step 1814, a check is made to see if all records in the patient data file have been processed. If the answer is found to be negative, i.e., additional records exist in the data file, the program reiterates steps 1806-1812 until the answer at step 1814 is found to be positive. This is an indication that all records in the patient data file have in fact been processed and, at that point, step 1816 is accessed where all the keyed data items are written into the database file corresponding to the patient name, and control is returned to the IDDI-Prolog program at step 1804.

Figure 19:
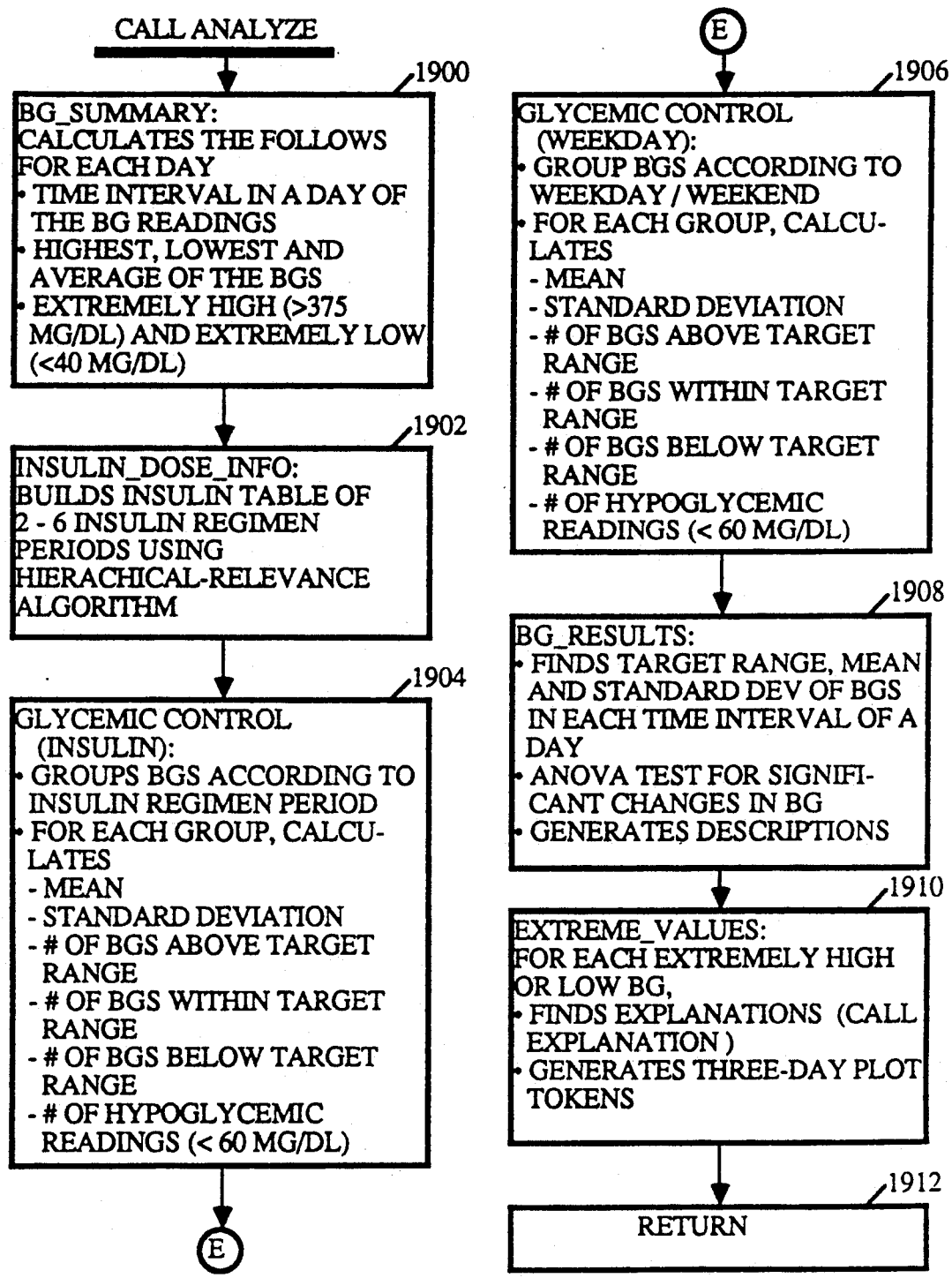

FIG. 19 is a detailed flowchart of the operation sequence involved in executing the functions of the Analyze module in the flowchart of FIG. 17. The module begins execution at step 1900 by performing the calculations necessary for generating the blood glucose (BG) Summary. More specifically, the following factors are calculated for each day:

1) the time interval in the day to which the BG readings correspond;
2) the highest, lowest and average values of the BGs; and
3) the extremely high (according to a preferred embodiment, greater than about 375 mg/dl) and extremely low (preferably, less than about 40 mg/dl) readings. It should be noted that other threshold values may be selected and either defined within the downloaded data from a glucose meter with sophisticated memory functions or supplied by the IDDI system user.

Subsequently, at step 1902, the processing necessary for generating insulin dosage information is accomplished in order to build an insulin table based on a plurality of 2-6 insulin regimens, preferably using the hierarchical relevance algorithm described above.

Next, at step 1904, the processing necessary for generating the necessary glucose control information is performed. More specifically, all BGs are grouped according to the identified insulin regimens and according to mealtimes within each regimen. Next, for each such group, the following are calculated: mean; deviation; number of BGs above target range; number of BGs within target range; number of BGs below target range; and number of hypoglycemic readings as defined, according to a preferred embodiment, by a BG reading less than 60 mg/dl.

Subsequently, at step 1906, calculations similar to those at step 1904 are performed for providing comparative glucose control information with respect to weekdays and weekend days. In accomplishing this, all BGs are grouped on a weekday/weekend day basis. Subsequently, for each such group, calculations identical to those performed at step 1904 are performed.

At step 1908, the processing necessary for generating BG results is performed. In particular, the target range, the mean and the standard deviation of BGs is found in each time interval of a day.

Initially, a tabular analysis of BGs is performed on an overall basis as well as for each mealtime showing whether the average BG was within the target range, and if not, how far above or below target it was, and how "spread out" or "variable" the readings were. Additional details pertaining to the manner in which BG results are generated will be discussed in detail below. In addition, the analysis of variance (ANOVA) tests are performed for identifying significant changes in BG levels. Corresponding descriptions are also generated at this point.

Subsequently, at step 1910, the processing necessary for identification and explanation of extreme BG values is performed. In particular, the BGs are tested to identify each extremely high or extremely low BG value and corresponding explanations are found using a procedure which will be described in detail below. In addition, at this point, three-day plot tokens are generated corresponding to each identified extreme value. These tokens are later used for generating corresponding sections of the output report. Subsequently, at step 1912, control is returned to the IDDI-Prolog program.

Referring now to FIG. 20A, there is shown a flowchart illustrating the processing details involved in a routine called "Insulin Dose Info" for executing the functions described at step 1902 in the Analyze flowchart of FIG. 19. The routine begins at step 2000 where the program starts with the assumption that only a single run comprising all days in the monitoring period exists, i.e., the daily readings in the patient data file correspond to a single insulin regimen.

Subsequently, at step 2002, readings are scanned from the first day to the last day of this initial run. The run is split at days when a sustained change from single to multiple shots of insulin (or vice versa) per day is detected. In this regard, a sustained change is defined to be a difference that occurs for more than a predefined threshold number of consecutive days. According to a preferred embodiment, this threshold number of days is defined to be three (3).

Subsequently, at step 2004, a check is made to see if the number of runs identified at step 2002 is greater than one. If the answer is positive, step 2006 is accessed where the program is set up to perform a series of operations for each one of the identified runs (Ri) in which a single insulin shot was taken. At step 2008, readings are scanned from the first day to the last day of the run and splits are made at days when a sustained change in amount of long-acting insulin is detected.

At step 2010, a check is made to see if the number of runs identified is greater than one. If the answer is found to be positive, the program accesses step 2012. If the answer at step 2010 is found to be negative, the possibly split run is recombined at step 2014.

Subsequently, at step 2015, readings within the run are scanned from the first day to the last day and the run is split at days when a sustained change in amount of intermediate-acting insulin is detected. At step 2016, it is determined whether or not the number of such runs of three or more days in duration is greater than one. If the answer is yes, step 2012 is accessed again.

If the answer at step 2016 is found to be negative, the possibly split run is recombined at step 2017. Subsequently, at step 2018, readings within the run are scanned and the run is split at days when a sustained change in amount of short-acting insulin is detected. Next, at step 2019, a check is made to see if any runs of three or more days duration have resulted. If the answer is positive, the program accesses step 2012. If the answer at step 2019 is found to be negative, the program recombines the possibly split run at step 2020 and step 2012 is accessed.

If, however, it is found at 2004 that the number of runs exceeding three days in duration is merely one, step 2022 is accessed where the program begins the run splitting routine again by restarting under the assumption that only a single run comprising all days in the monitoring period exists. Subsequent processing is accomplished in accordance with the flow sequence shown at FIG. 20B.

At step 2024 in the flowchart of FIG. 20B, readings are scanned and the run is split at days when a sustained change in a number of insulin shots is detected. Next, at step 2026, a check is made as to whether any runs of three or more days duration have resulted. If the answer is found to be positive, step 2028 is accessed where the programs returns to the Analyze subprogram. If the answer at step 2026 is found to be negative, the program begins the run splitting process again with a single run comprising all days in the monitoring period; this is done at step 2030.

Subsequently, at step 2031, readings within the run are scanned and the run is split at days when a sustained change in amount of long-acting insulin is detected. Next, at step 2032, a check is made to see if any runs of three or more days duration have resulted. If the answer is positive, the program returns at step 2028. If the answer at step 2032 is found to be negative, the program begins the run splitting process again at step 2033 using a single run of all days.

Subsequently, at step 2034, all readings in the run are scanned and the run is split at days when a sustained change in amount of intermediate-acting insulin is detected. Next, at step 2035, a check is made for the presence of runs with three or more days duration. If the answer is found to be positive, the program returns at step 2028. If, however, the answer is found to be negative at step 2035, the run splitting process is begun again at step 2036 using a single run of all days.

Subsequently, at step 2038, all readings in the run are scanned and the run is split at days when a sustained change in amount of short-acting insulin is detected. Next, at step 2040, a check is made for the presence of runs with three or more days duration. If the answer is found to be positive, the program returns at step 2028. If, however, the answer is found to be negative at step 2040, the possibly split run is recombined at step 2042, and the program returns to the Analyze subprogram at step 2028.

It should be noted that the flowchart of FIG. 20A shows the routine returning to the calling subprogram at step 2012 after performing steps 2008-2020 for each of the runs identified at step 2004, in accordance with the conditions set up at step 2006.

Figure 21:
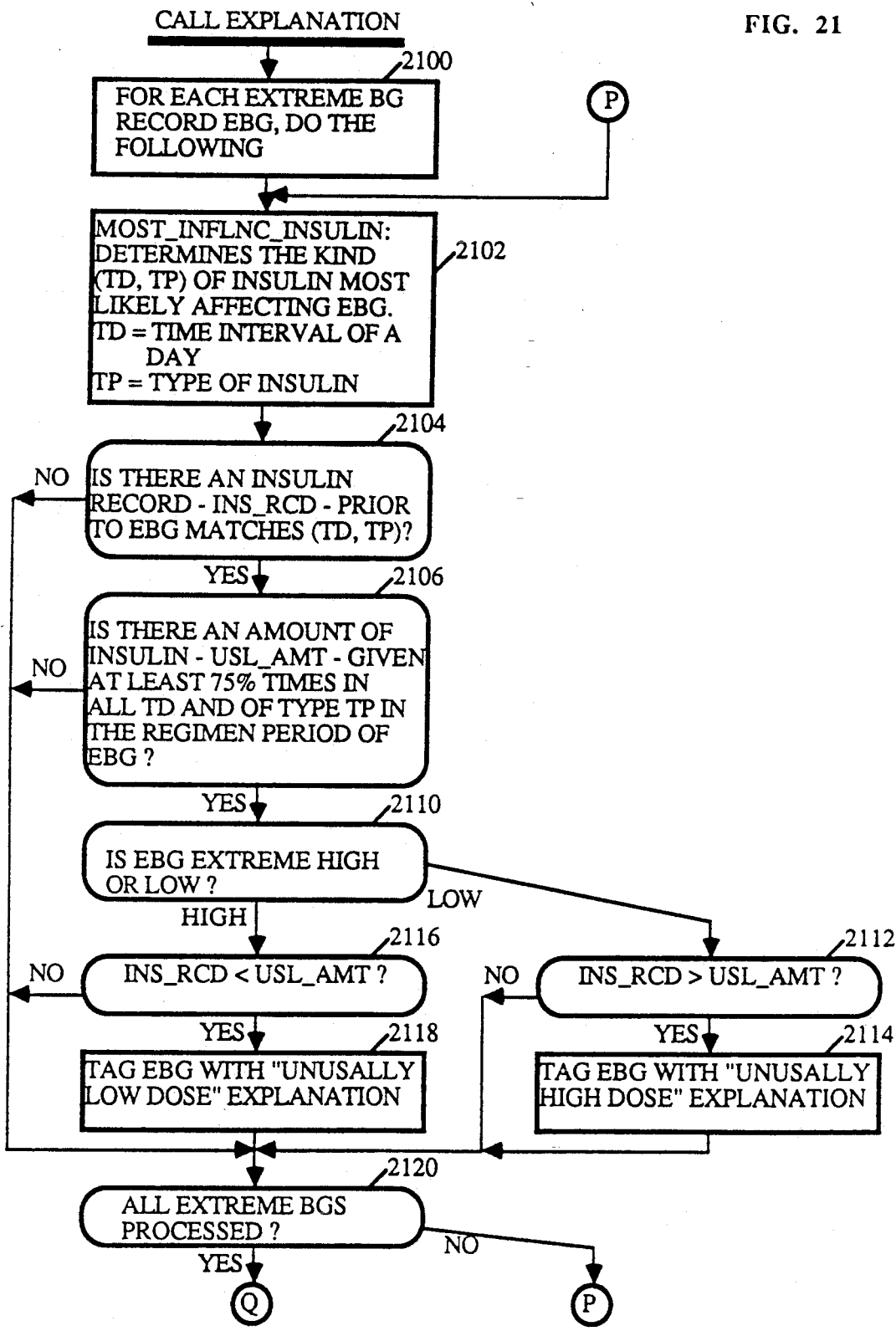
Figure 21A:
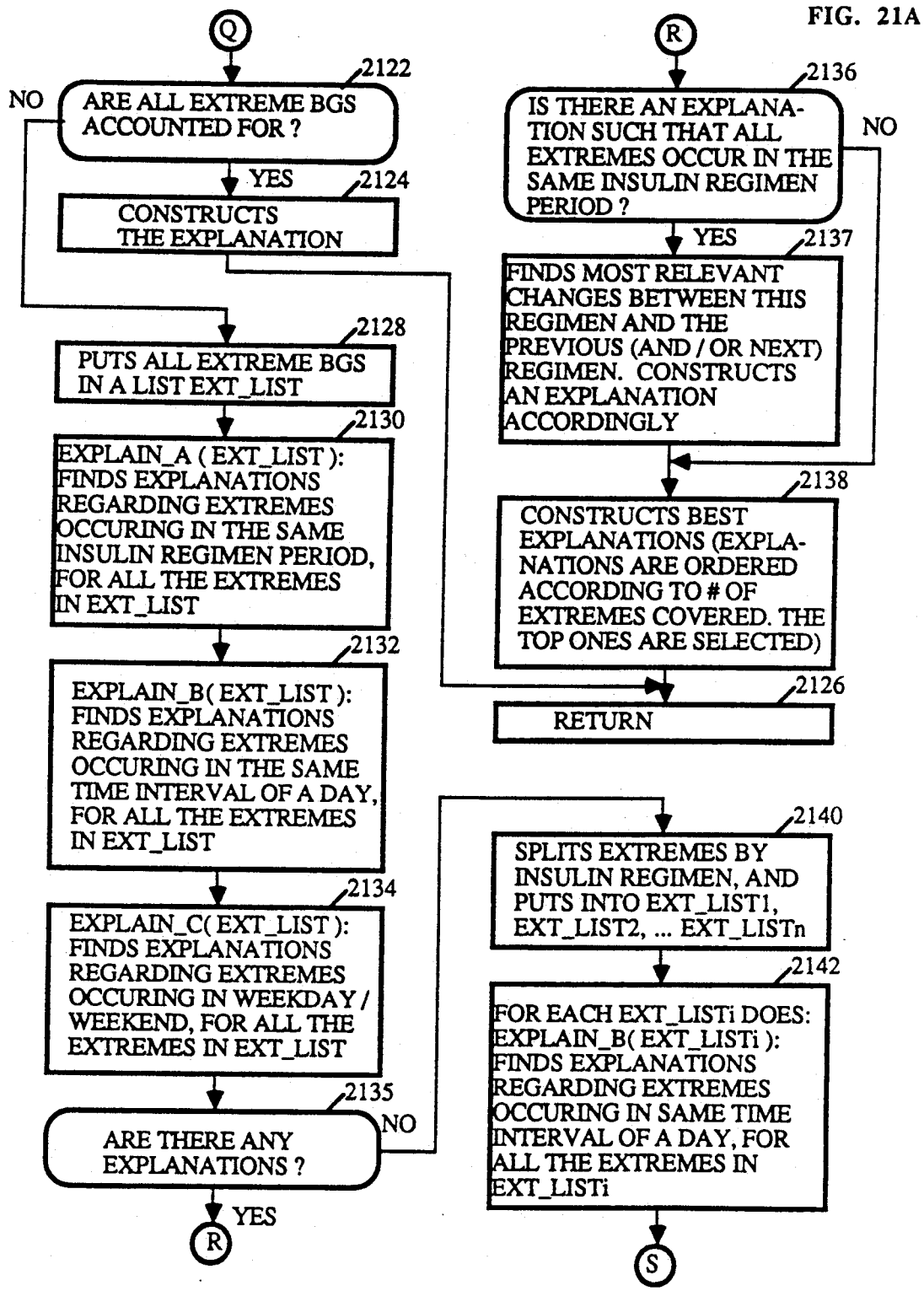
Figure 21B:
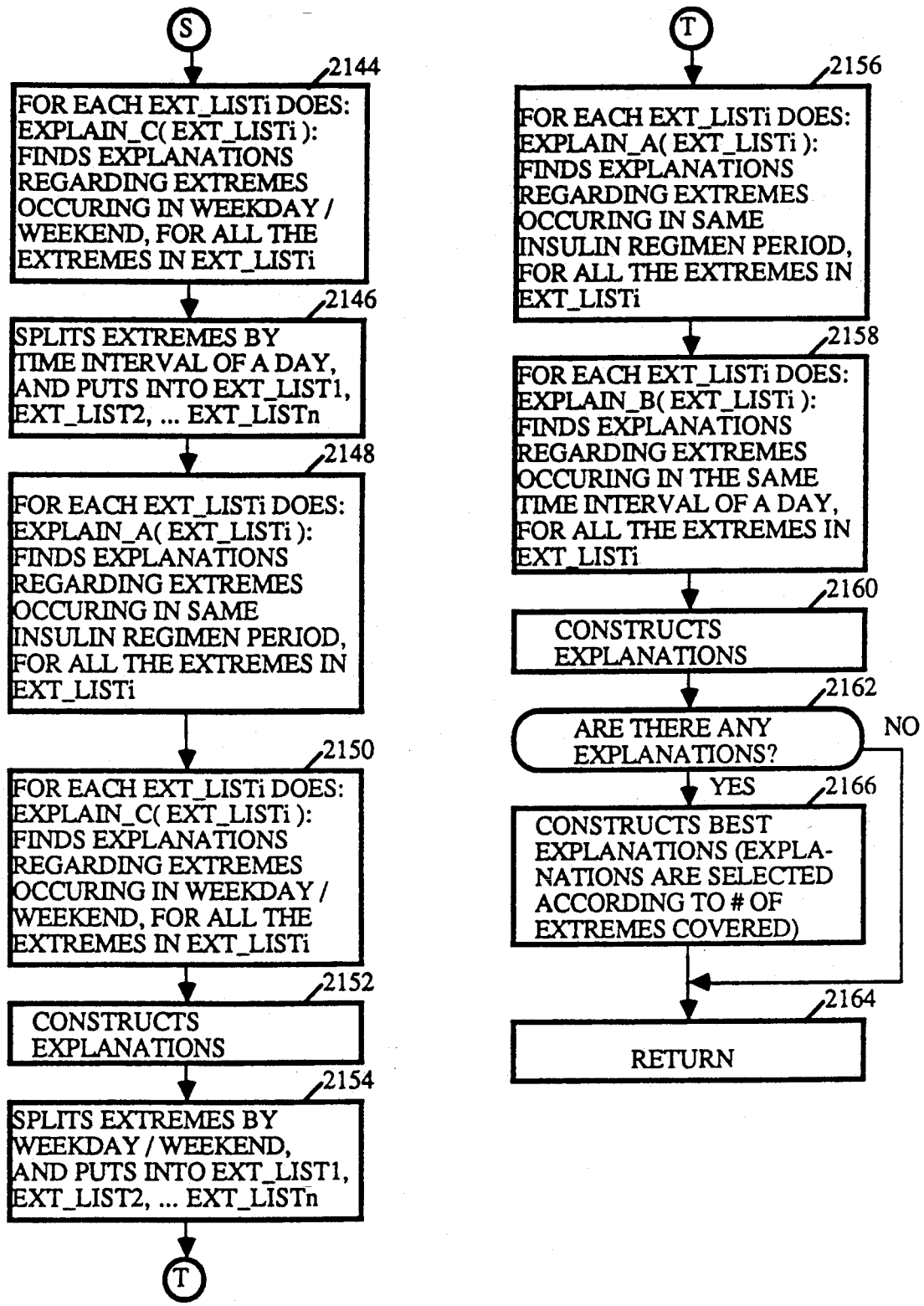

Referring now to FIGS. 21, 21A and 21B, there are shown flowcharts detailing the operational sequence involved in generating explanations for the presence of extreme BG values. The program begins at step 2100 where appropriate parameters are set for performing a series of processing operations for each identified extreme BG value (EBG). Next, at step 2102, the program determines the kind of insulin (TD, TP) which most likely affected the EBG; in this regard, TD represents the time interval of day, and TP represents the type of insulin.

Next, at step 2104, a check is made to see if an insulin record (INS-RCD) exists prior to the EBG which matches the identified insulin type (TD, TP). If the answer is positive, step 2106 is accessed where a check is made to see if a particular amount of insulin (the "usual amount", USL-AMT) was taken at least a threshold percentage (preferably, about 75%) of the time in the time intervals corresponding to TD and corresponding to the insulin type TP within the regimen corresponding to the EBG. For instance, if TD corresponds to lunchtime, the threshold check is made in all lunchtime intervals within the applicable insulin regimen. If the answer at 2106 is found to be positive, a check is made at step 2110 to see if the identified EBG is extremely high or extremely low.

If the answer at step 2110 indicates that the EBG was low, step 2112 is accessed where a check is made to see if the value of INS-RCD is greater than the value corresponding to USL-AMT. Following a positive answer at step 2112, step 2114 is accessed where the identified EBG is tagged with an explanation identifying it as an "unusually high dose."

If it is found at step 2110 that the identified EBG was high, a check is made at step 2116 to see if the value for INS-RCD is less than the value for USL-AMT. Following a positive answer at step 2116, step 2118 is accessed where the EBG at issue is tagged with an explanation identifying it as an "unusually low dose."

At the end of steps 2114 and 2118, as well as following a negative answer at steps 2104, 2106, 2112, and 2116, step 2120 is accessed where a check is made to see if all identified EBGs have been processed. If the answer is found to be negative, the program returns to step 2102 for reiterating the rest of the program until the answer at step 2120 is found to be positive. If the answer at step 2120 is positive, program execution is continued according to the flowchart of FIG. 21A.

At step 2122, a check is made to see if all EBGs have been accounted for. If the answer is yes, a corresponding explanation is constructed at step 2124 and the program returns to the calling subprogram at step 2126. If the answer at step 2122 is found to be negative, all EBGs are compiled into a list (identified as EXT-LST) at step 2128. Next, at step 2130, the program determines whether all or most EBGs contained in that list occur in the same insulin period, and, if so, a corresponding explanation is generated. This is accomplished in accordance with a subroutine called Explain-A which will be described below.

Next, at step 2132, the program determines whether all or most EBGs in the list occur in the same time interval of a day, and, if so, a corresponding explanation is generated. This is accomplished in accordance with a subroutine called Explain-B to be described below. Next, at step 2134, the program determines if all or most EBGs in the list occur in weekdays or on weekends and, if so, a corresponding explanation is generated.

Subsequently, at step 2135, a check is made to see if any explanations have been found. If the answer is found to be positive, step 2136 is accessed where it is determined whether an explanation exists identifying the occurrence of all EBGs in the same insulin regimen period. If the answer at step 2136 is positive, step 2137 is accessed where the most relevant change between the identified insulin regimen period and an adjacent regimen period is identified, and a corresponding explanation generated.

Following step 2137 and if the answer at step 2136 is negative, step 2138 is accessed where the best possible explanations at that point are constructed. More specifically, explanations are ordered according to the number of EBGs covered thereby and the top explanations under such a ranking are selected. Subsequently, the program returns control to the Analyze subprogram at step 2126.

If the answer at step 2136 is found to be negative, i.e., no explanations are found to exist, the extreme values or EBGs are split according to insulin regimens and put into corresponding lists EXT-LST1, EXT-LST2, ... EXT-LSTn. This is performed at step 2140.

Next, at step 2142, the operations performed in accordance with the routine Explain-B (see step 2132) are sequentially performed for all EBGs in each of these lists.

The following sequence of operations is described in connection with the flowchart of FIG. 21B where, at step 2144, similar operations are performed in accordance with the routine Explain-C to be described below. Next, at step 2146, the EBGs are split according to time intervals of a day and put into corresponding lists.

Next, at step 2148, the operations corresponding to the routine Explain-A are performed for each such list. At step 2150, the operations corresponding to the routine Explain-C are performed for each such list. At step 2152, corresponding explanations are constructed, and at step 2154, the EBGs are split by weekday/weekend days and put into corresponding lists.

At step 2156, the operations corresponding to routine Explain-A are performed for each such list. Next, at step 2158, operations corresponding to the routine Explain-B are performed for each such list and, at step 2160, corresponding explanations are constructed.

At step 2162, a check is made to see if any explanations are, in fact, present. If the answer is found to be negative, the program returns control to the Analyze subprogram at step 2164. If, however, some explanations are found to exist at step 2162, step 2166 is accessed where the "best" explanations are constructed on the basis of the highest number of EBGs covered thereby.

Figure 22:
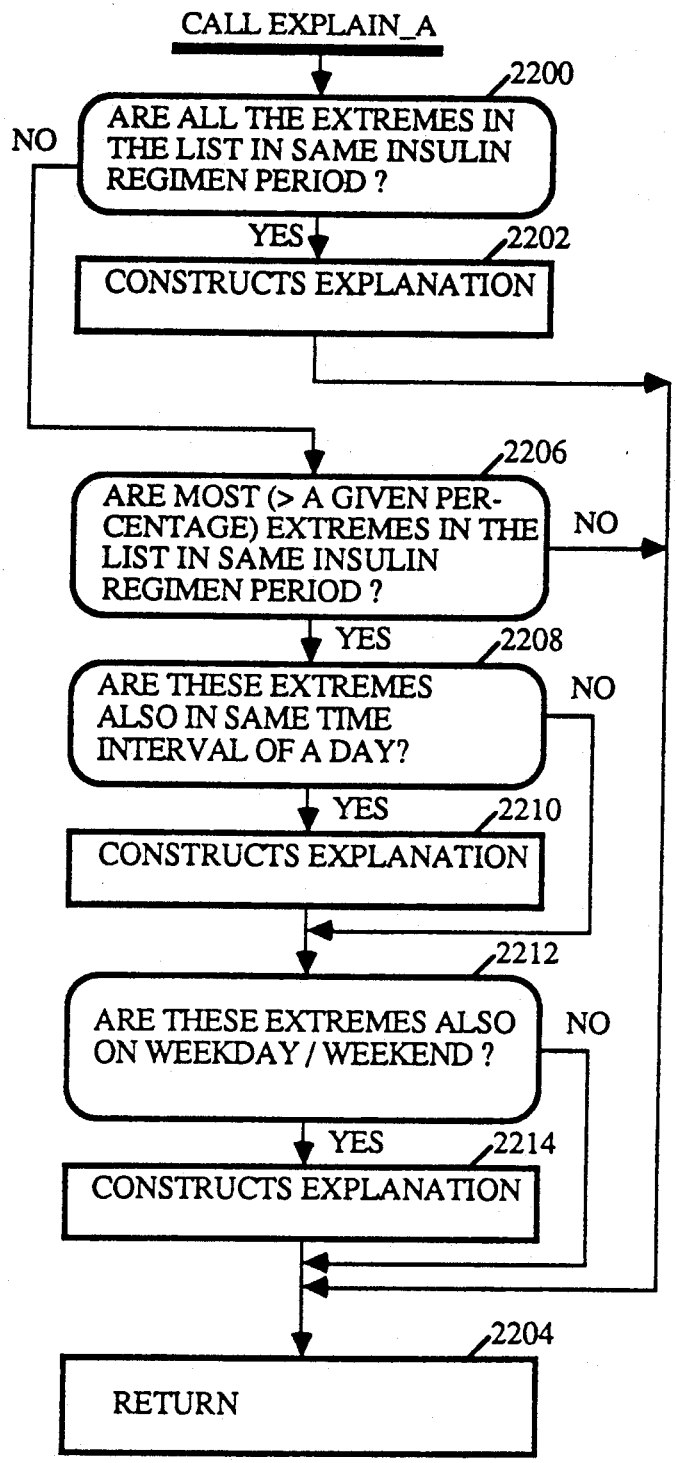

Referring now to FIG. 22, there is shown a flowchart illustrating the sequence of operations corresponding to the routine Explain-A referred to in the flowcharts of FIGS. 21A-B. At step 2200, a check is made to see if all the EBGs in the list being considered fall within the same insulin regimen. If the answer is found to be positive, the corresponding explanation is constructed at 2202 and the program returns to the Analyze subprogram at step 2204.

If the answer at step 2200 is found to be negative, a check is made at step 2206 to see if more than a given threshold percentage (preferably, about 66.6%) of the EBGs in the list fall within the same insulin regimen. If the answer is positive, a check is made at step 2208 to see if the EBGs are also within the same time interval of day. If the answer is found to be positive, the corresponding explanation is constructed at step 2210 and step 2212 is accessed where a check is made to see if these EBGs all fall either within weekdays or on weekends.

If the answer at step 2212 is found to be positive, a corresponding explanation is generated at 2214. At the end of step 2214, as well as at the generation of negative answers at steps 2206 and 2212, the program returns at step 2204. Further, if the answer at step 2208 is found to be negative, the program reiterates from step 2212.

Figure 23:
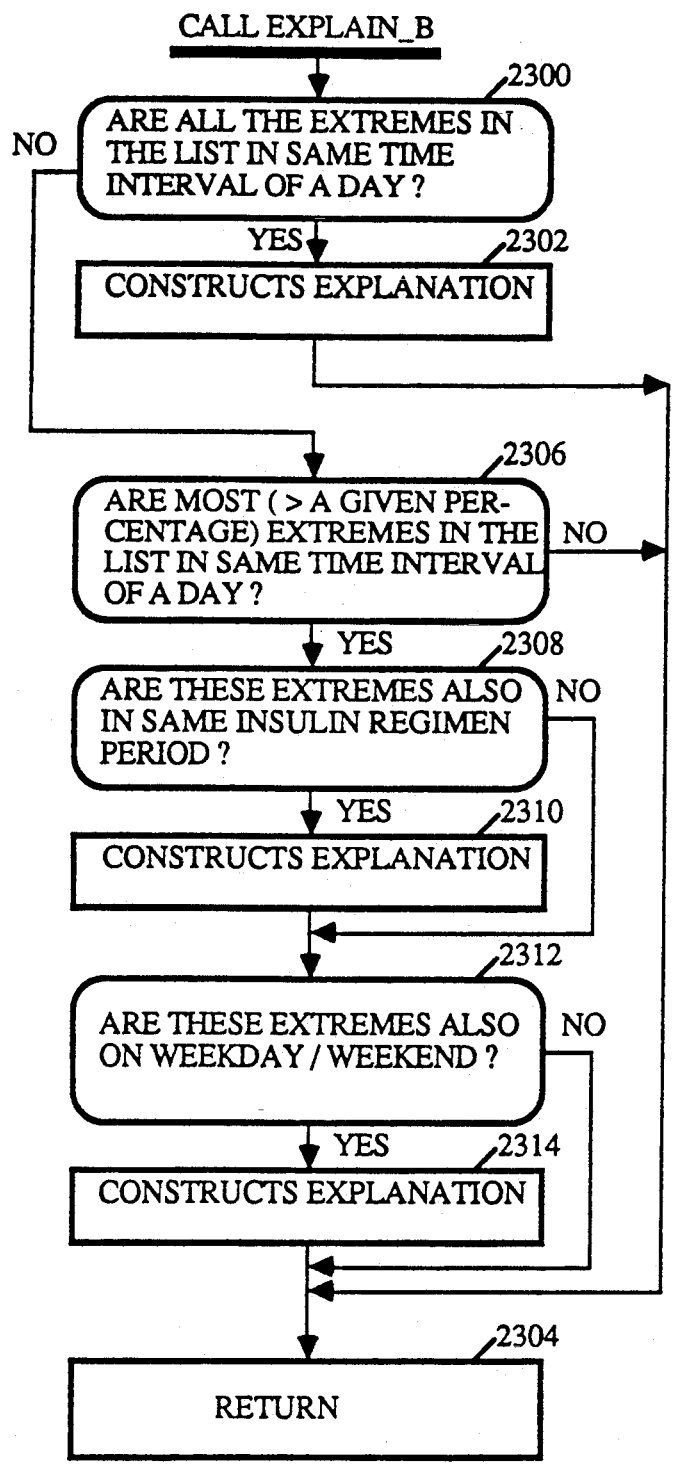

Referring now to FIG. 23, there is shown a flowchart of operations corresponding to the routine Explain-B. At step 2300, a check is made to see if all the EBGs in the list correspond to the same time interval of day. If the answer is positive, the corresponding explanation is constructed at step 2302 and the program returns to the subprogram at step 2304.

Following a negative answer at step 2300, step 2306 is accessed where a check is made to see if more than a given threshold percentage (preferably, about 66.6%) of the EBGs in the list fall within the same time interval of a day. If the answer is positive, a check is made at step 2308 to see if these EBGs also fall within the same insulin regimen. If the answer is again positive, the corresponding explanation is constructed at 2310 and step 2312 is accessed where a check is made to see if the EBGs fall within weekdays or within weekends. Next, corresponding explanations are constructed at step 2314 following which the program returns to the subprogram at step 2304.

The program also returns at step 2304 following negative answers at steps 2306 and 2312. In addition, if the answer at step 2308 is found to be negative, step 2312 and the following steps are accessed.

Figure 24:
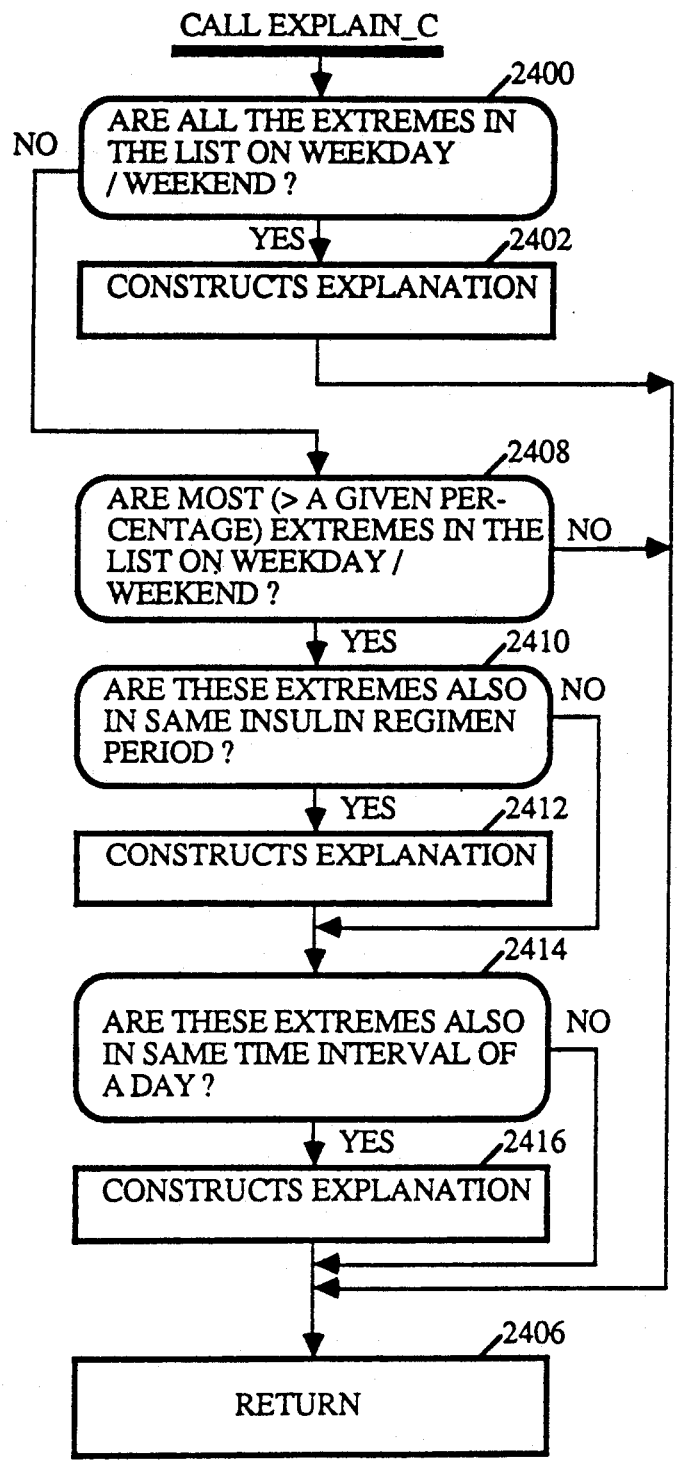

Referring now to FIG. 24, there is shown a flowchart corresponding to the operational sequence for the routine Explain-C. At step 2400, a check is made to see if all the EBGs in the list fall on weekdays or on weekends. If the answer is positive, the corresponding explanation is constructed at step 2402, and the program returns at step 2406.

Following a negative answer at step 2400, step 2408 is accessed where a check is made to see if more than a given threshold percentage (preferably about 66.6%) of the EBGs in the list fall either on a weekday or on the weekend. If the answer is positive, a check is made at step 2410 to see if the EBGs also fall within the same insulin regimen. If the answer is again found to be positive, a corresponding explanation is constructed at step 2412. Subsequently, step 2414 is accessed where a check is made to see if the EBGs also fall within the same time interval of day and, if so, the corresponding explanation is constructed at step 2416 before the program returns to the subprogram at step 2406.

Step 2406 is also accessed if the answers at steps 2408 and 2414 are found to be negative. Further, if the answer at step 2410 is found to be negative, i.e., the EBGs do not fall within the same insulin regimen period, steps 2414 and the following steps are accessed.

Figure 25:
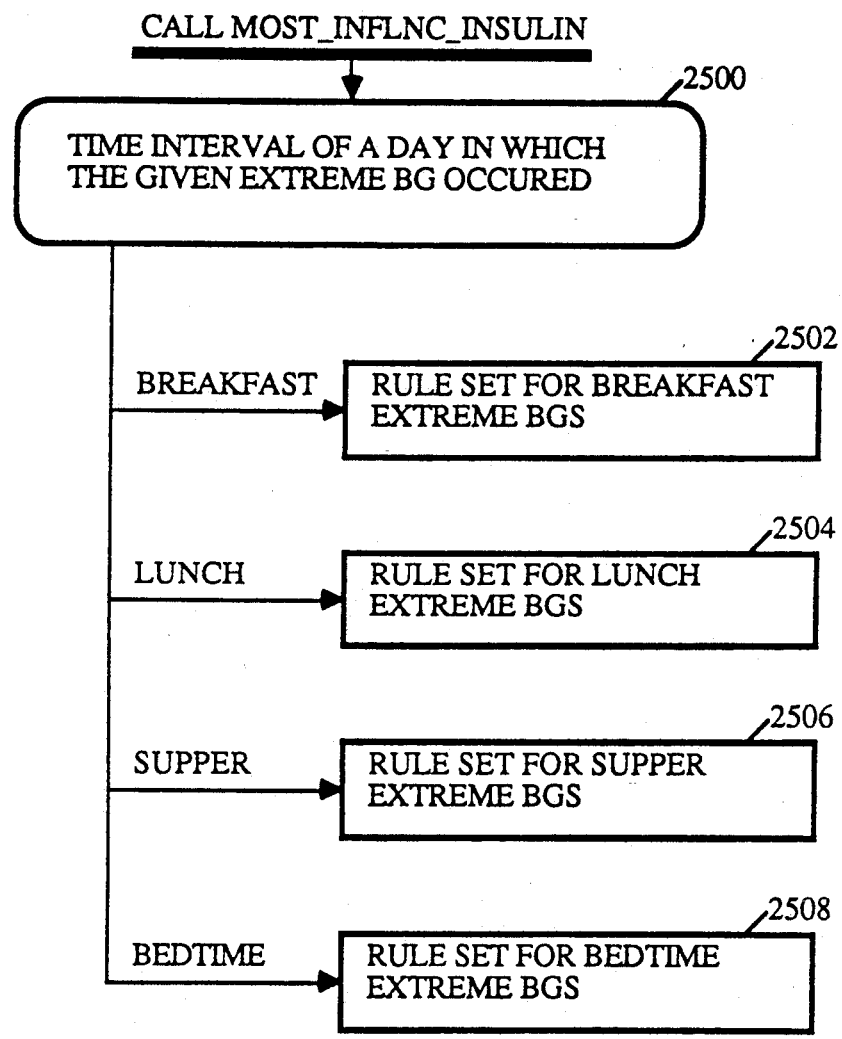

FIG. 25 is a flowchart illustrating the manner in which the insulin type most likely to have effected an extreme blood glucose value is determined. At step 2500, the time interval of a day in which the given EBG occurred is noted. If the time interval is found to correspond to breakfasttime, a corresponding rule set for breakfast EBGs is accessed at step 2502.

If the time interval is found to correspond to lunchtime, a corresponding rule set for lunch EBGs is accessed at step 2504. If the time interval is found to correspond to suppertime, a corresponding rule set for supper EBGs is accessed at step 2506 and if the time interval is found to correspond to bedtime, a corresponding rule set for bedtime EBGs is accessed at step 2508.

Figure 26:
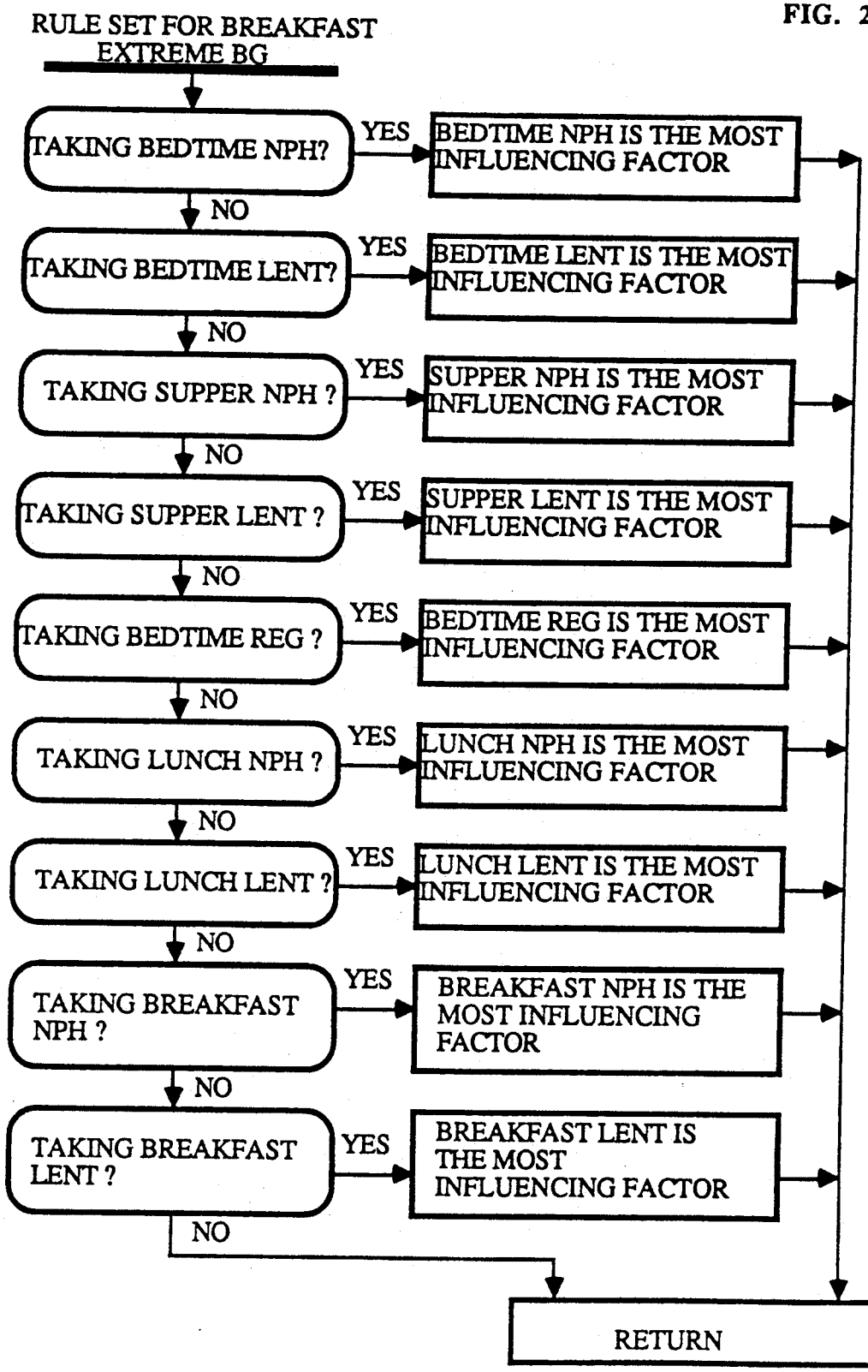

Referring now to FIG. 26, there is an illustration of the rule set for breakfast EBGs. The rule set is self-explanatory and provides an indication of the hierarchy according to which the influencing factors are identified. For instance, if it is determined that bedtime NPH insulin was being taken within the relevant time frame for the EBG, that type of insulin is identified as the most influencing factor. If bedtime NPH insulin was not being taken, the program hierarchically tests to see if bedtime LENTE insulin, supper NPH insulin, supper LENTE insulin, bedtime regular insulin, lunch NPH insulin, lunch LENTE insulin, breakfast NPH insulin, or breakfast LENTE insulin was being taken. Following the presence of any such factors, the corresponding type of insulin is identified as being the most influencing factor.

Figure 27:
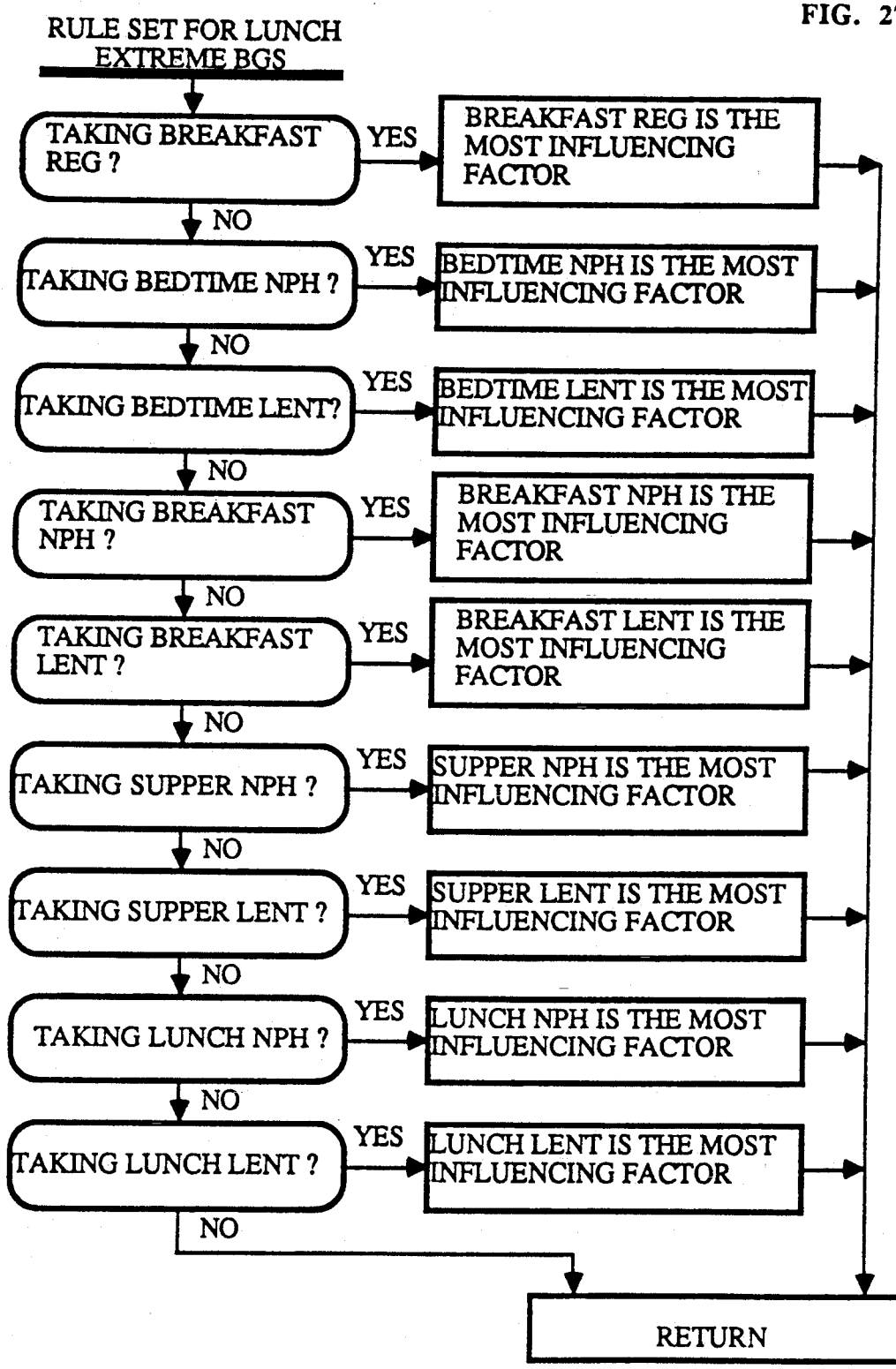

FIG. 27 shows a similar rule set applicable to lunch EBGs. In this case, the influencing factor hierarchy begins with breakfast regular insulin and continues down through bedtime NPH, bedtime LENTE, breakfast NPH, breakfast LENTE, supper NPH, supper LENTE, lunch NPH, and lunch LENTE types of insulin.

Figure 28:
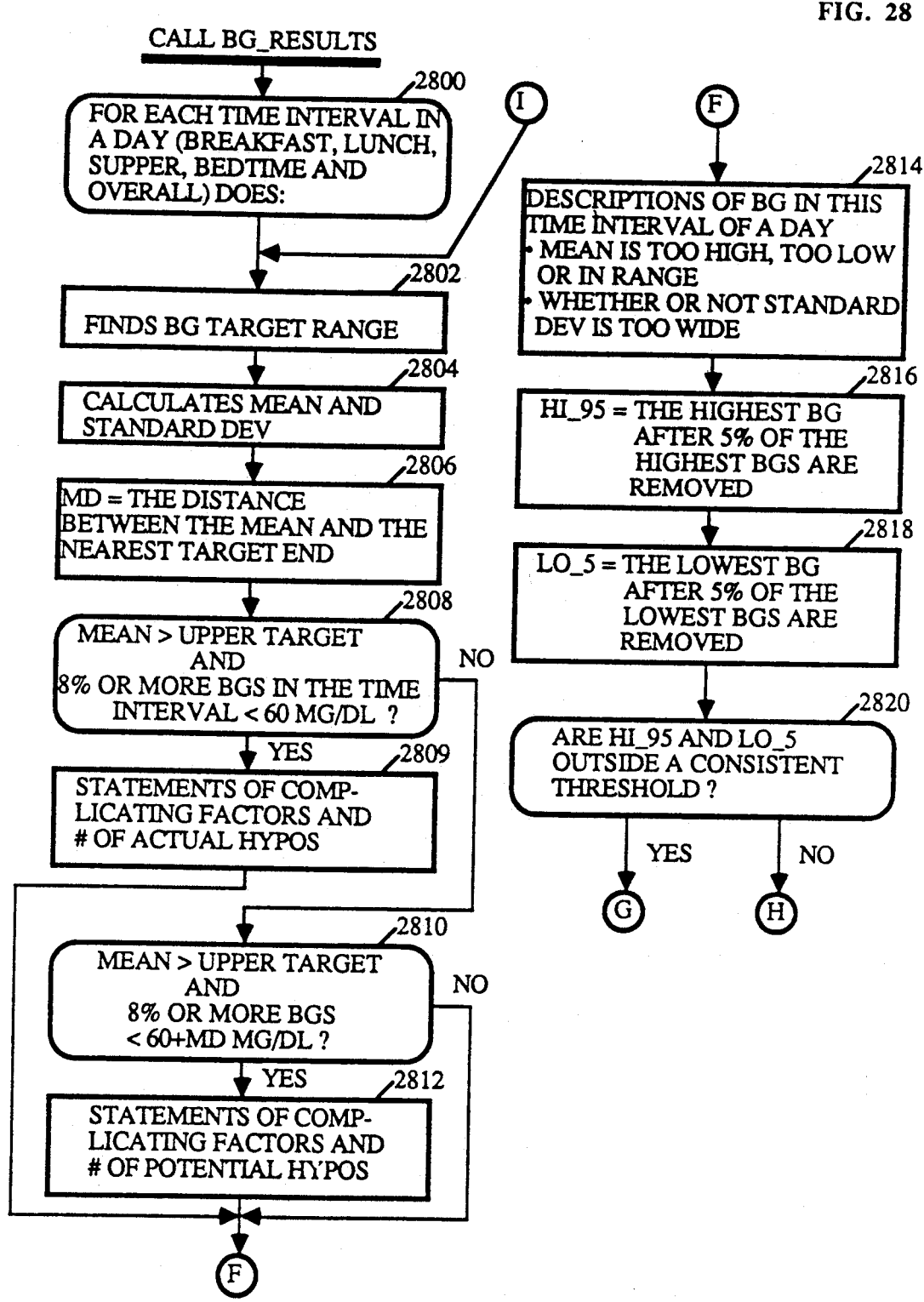
Figure 28A:
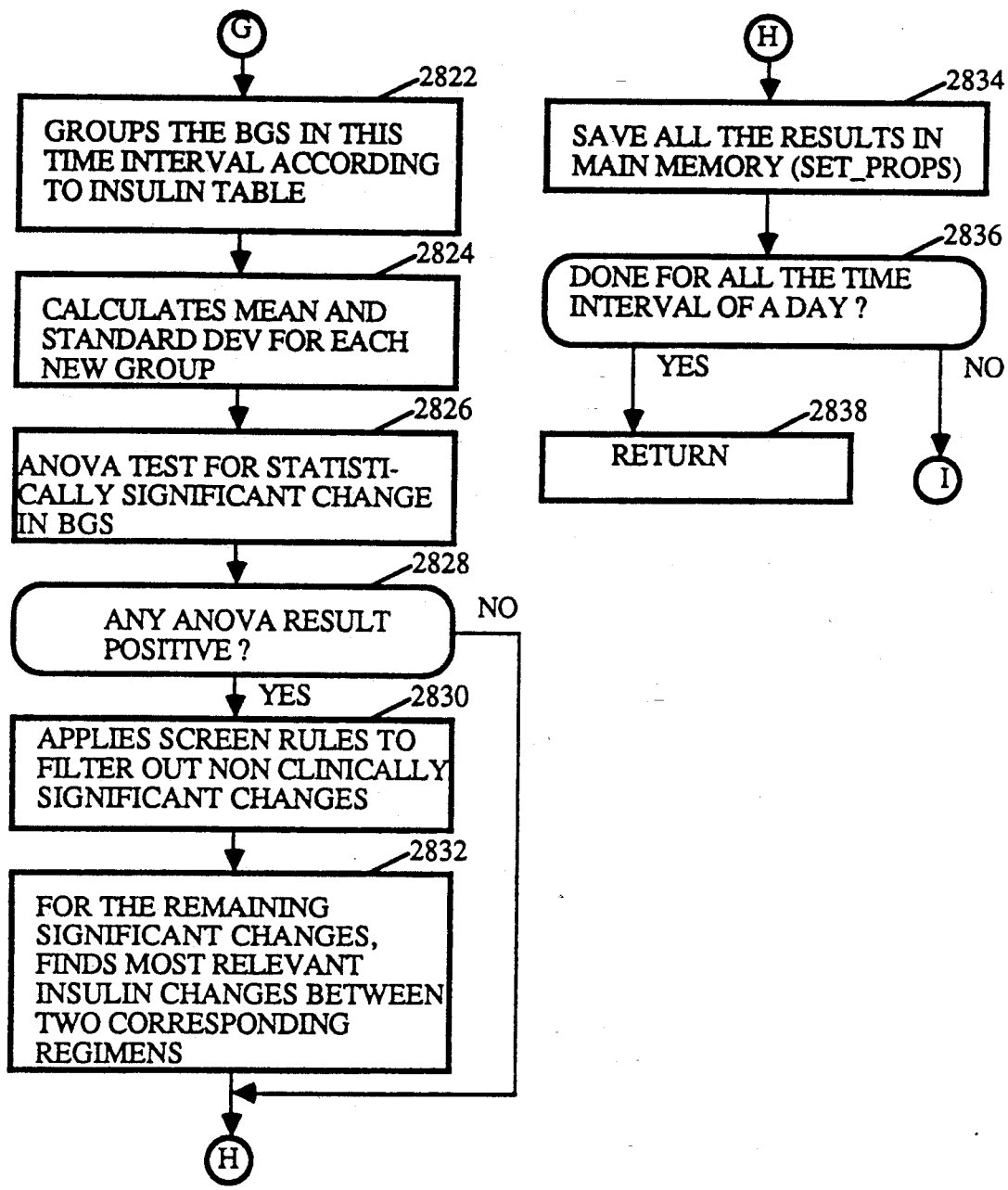

Referring now to FIGS. 28–28A, there are shown flowcharts identifying the manner in which blood glucose results are determined and tabulated in accordance with step 1908 of the Analyze routine of FIG. 19. At step 2800, the program takes steps for performing a series of processing operations for each time interval within each day at issue. At step 2802, the BG target range is found. At step 2804, the corresponding mean and standard deviation is calculated. At step 2806, the distance "MD" between the mean and the nearest end of the target range is calculated.

At step 2808, a determination is made as to whether or not (i) the calculated mean exceeds the upper end of the target range and (ii) a specified threshold percentage (preferably 8%) or more of the BGs in the time interval are hypoglycemic, i.e., at a level less than 60 mg/dl. If the answer is found to be negative, step 2810 is accessed where a determination is made as to whether or not (i) the calculated mean exceeds the upper end of the target range and (ii) a threshold percentage (preferably 8%) or more of the BGs have a value less than the sum of 60 plus the value MD mg/dl. If the answer at step 2810 is found to be positive, statements of complicating factors and number of potential hypos are constructed at step 2812.

If the answer at step 2808 is found to be positive, corresponding statements of complicating factors and number of actual hypos are constructed at step 2809. At the end of steps 2809 and at the generation of a negative answer at step 2810, step 2814 is accessed where corresponding descriptions of BGs in the time interval at issue are generated. In particular, the mean is identified as being too high, too low or within range and the standard deviation is identified as being too wide, if that is found to be the case.

Subsequently, at step 2816, a BG value identified as HI-95 is determined by first discarding the top 5% of the BGs associated with the time interval after they have been ranked in terms of highest to lowest values, and then picking the highest BG value to be HI-95. Similarly, at step 2818, a BG value identified as LO-5 is extracted by first discarding the bottom 5% of the BGs after they have been similarly ranked and then picking the lowest BG value to be LO-5. Next, at step 2820, a determination is made as to whether or not the HI-95 and LO-5 BGs are outside a consistent threshold. If the answer is found to be positive, step 2822 is accessed (see FIG. 28A) where the BGs in the time interval are grouped according to insulin regimens and time intervals within each regimen, and at step 2824, the mean and standard deviation are calculated for each new group.

Subsequently, step 2826 is accessed where the analysis of variance (ANOVA) test is performed to identify a statistically significant change in BGs. At step 2828, a check is made to see if any ANOVA test result was positive. If the answer is found to be positive, step 2830 is applied where predefined screen rules are applied to filter out non-clinically significant changes. Details about these screen rules are described below with reference to FIG. 30. Next, at step 2832, the remaining significant changes are analyzed to find the most relevant insulin changes between two corresponding insulin regimens. This function is preferably performed according to the flow sequence described above in connection with sub-routine of FIG. 25.

Following step 2832, as well as if all the ANOVA tests at step 2828 are found to be negative, step 2834 is accessed where the results generated to that point are saved in the Main system memory. Next, at step 2836, a check is made to see if all time intervals have been analyzed. If the answer is negative, the program returns to step 2802 and executes all following steps sequentially. If the answer is found to be positive, the program returns at step 2838.

Figure 29:
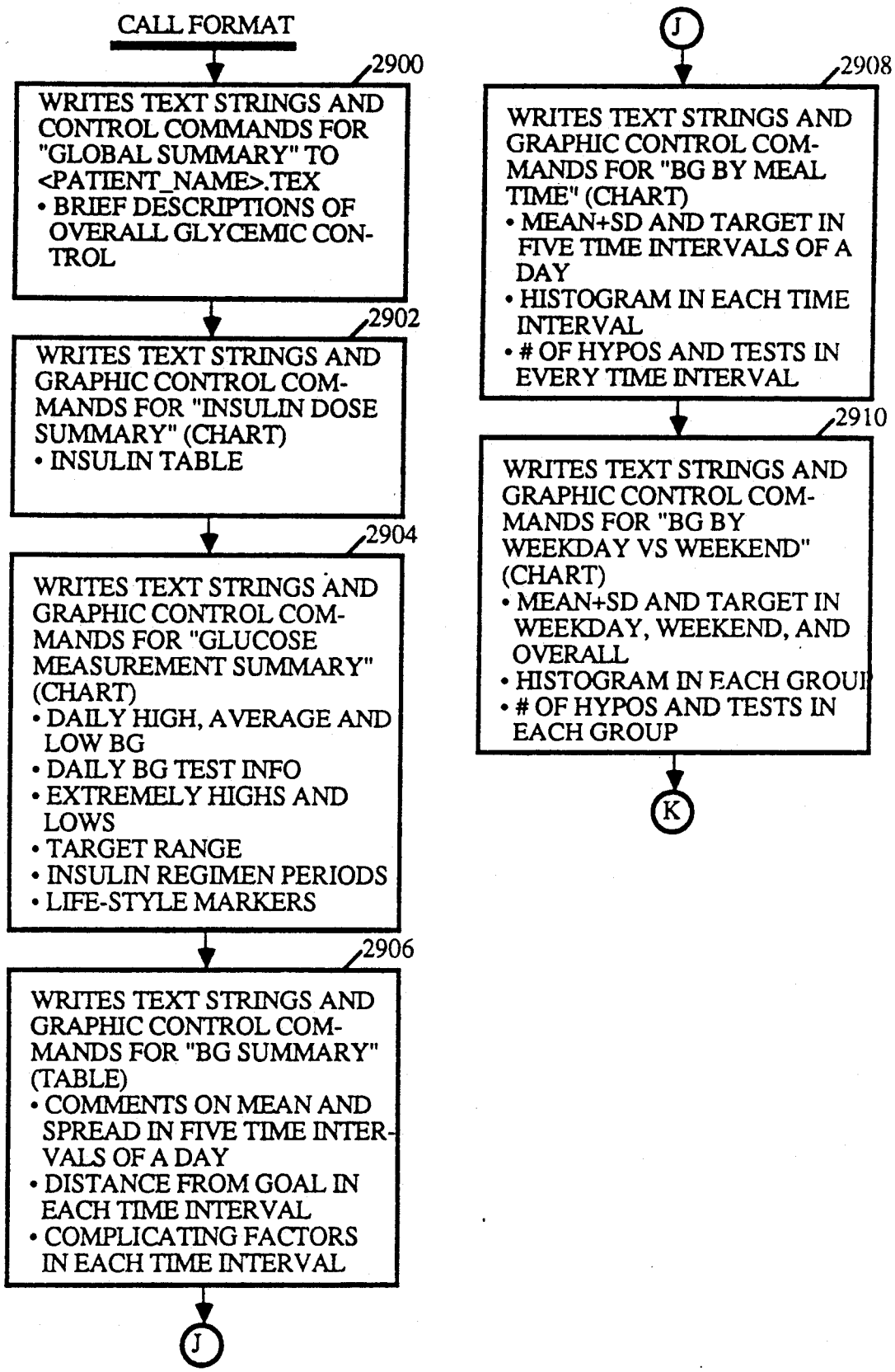
Figure 29A:
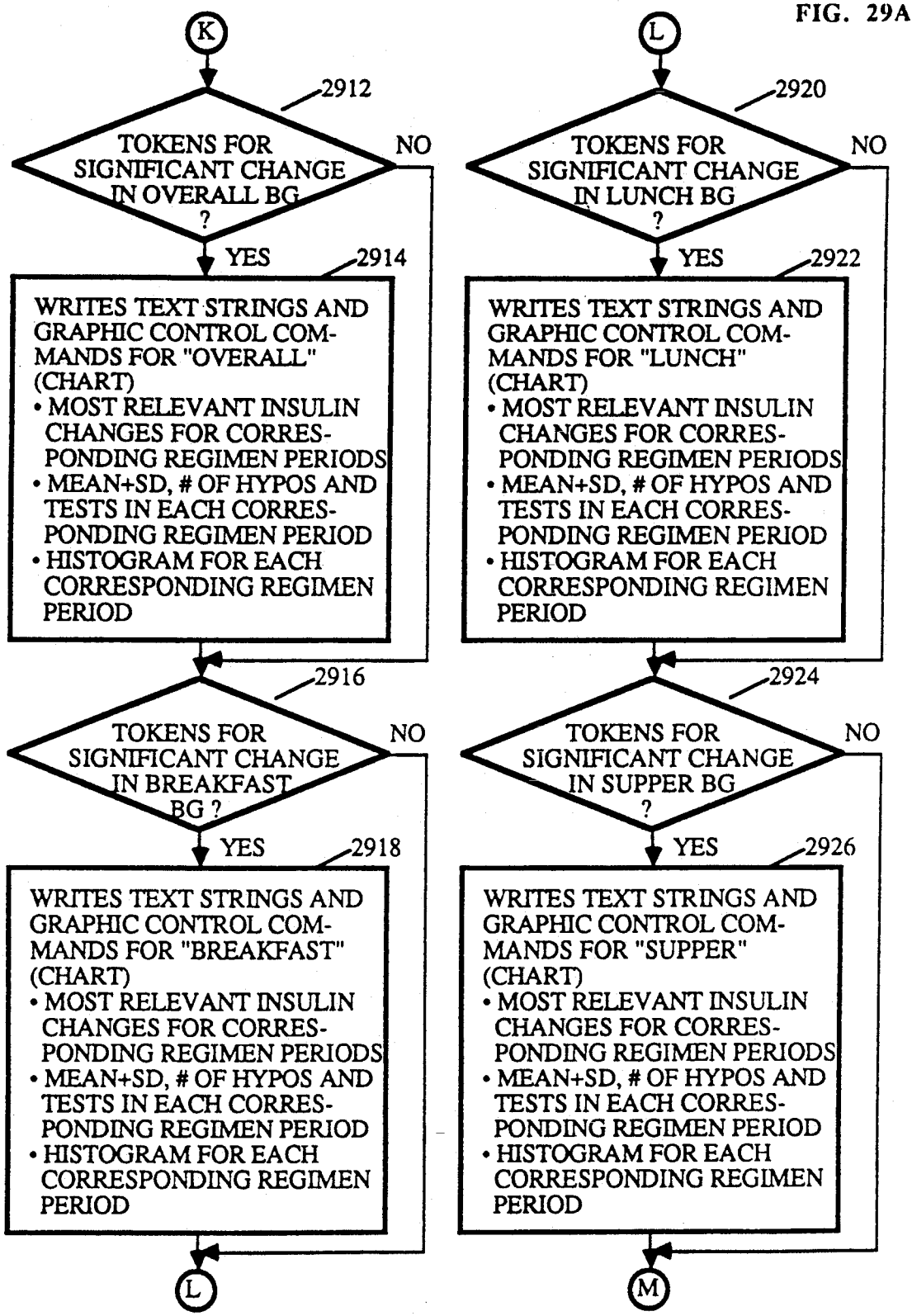
Figure 29B:
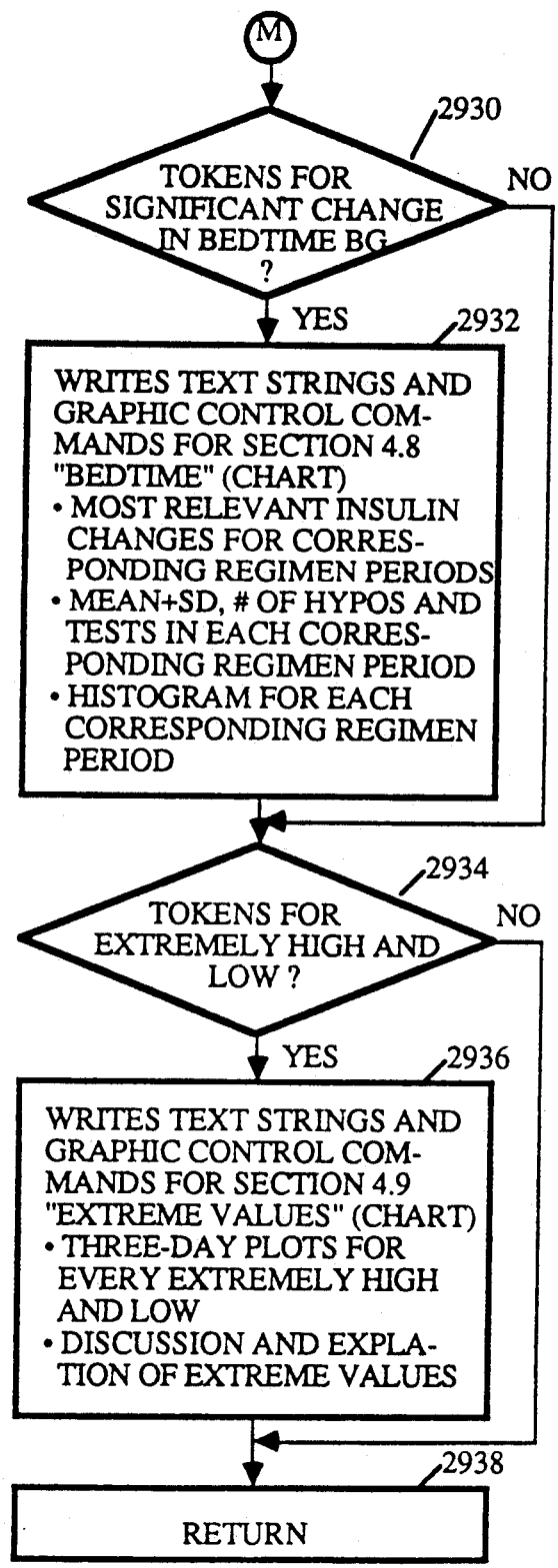

Referring now to FIGS. 29–29B, the step 2838. operational sequence involved in executing the Format module is described in detail and generating the IDDI data interpretation report described above in connection with FIGS. 2–12. At step 2900, text strings and control commands are written for generating the "Global Summary" section of the data interpretation report along with brief descriptions of the overall glycemic control. Next, at step 2902, text strings and graphic control commands are written for generating the "Insulin Dose Summary" section of the data interpretation report along with the associated insulin table.

Next, at step 2904, text strings and graphic control commands are written for the "Glucose Measurement Summary" section of the data interpretation report including daily high, average and low BGs, daily BG test information, extremely high and low readings, target range, insulin regimen periods, and life-style markers, if any.

Subsequently, at step 2906, text strings and graphic control commands are written for generating the "BG Summary" section of the data interpretation report along with comments on the mean and spread in the time intervals of a day, distance from goal in each time interval, and complicating factors in each time interval.

Next, at step 2908, text strings and graphic control commands are written for generating the "BG By Meal Time" section of the data interpretation report along with the associated mean, standard deviation and target according to the five time intervals, histograms in each time interval, and the number of hypos and tests in each time interval.

Next, at step 2910, text strings and graphic control commands are written for generating the "BG By Weekday Versus Weekend" section of the data interpretation report along with the associated information.

Next, at step 2912, a check is made to see if there are any tokens identifying significant changes in overall BG levels. If the answer is positive, text strings and graphic control commands are written for generating the "Overall BG Summary" section of the data interpretation chart along with the most relevant insulin changes for corresponding regimen periods, associated mean, standard deviation, number of hypos and tests in each corresponding regimen, and the histogram for each corresponding regimen.

At the end of step 2914 and following a negative answer at step 2912, step 2916 is accessed where a check is made for the presence of tokens corresponding to a significant change in breakfast BG levels. If the answer is found to be positive, text strings and graphic control commands are written at step 2918 for generating the "Breakfast" section of the data interpretation chart along with the associated information.

At the end of step 2918 and following a negative answer at step 2916, step 2920 is accessed where a check is made for the presence of tokens corresponding to a significant change in lunch BG levels. If the answer is found to be positive, step 2922 is accessed where text strings and graphic control commands are written for generating the "Lunch" section of the data interpretation report along with the associated information.

At the end of step 2922 and following a negative answer at step 2920, a check is made at step 2924 for the presence of tokens corresponding to a significant change in supper BG levels. If the answer is found to be positive, text strings and graphic control commands are written for generating the "Supper" section of the data interpretation report along with the associated information.

At the end of step 2926 and following a negative answer at step 2924, a check is made at step 2930 (see FIG. 29B) for the presence of tokens identifying a significant change in bedtime BG levels. If the answer is found to be positive, text strings and graphic control commands are written for generating the "Bedtime" section of the data interpretation report along with the associated information. This is accomplished at step 2932. At the end of this step, as well as following a negative answer at step 2930, step 2934 is accessed where a check is made for the presence of tokens corresponding to the presence of extremely high or low BGs.

If the answer at step 2934 is found to be positive, text strings and graphic control commands are written for generating the "Extreme Values" section of the data interpretation report along with the associated data shown. This is accomplished at step 2936 at the end of which, as well as following a negative answer at step 2934, the program returns in normal mode at step 2938.

Figure 30:
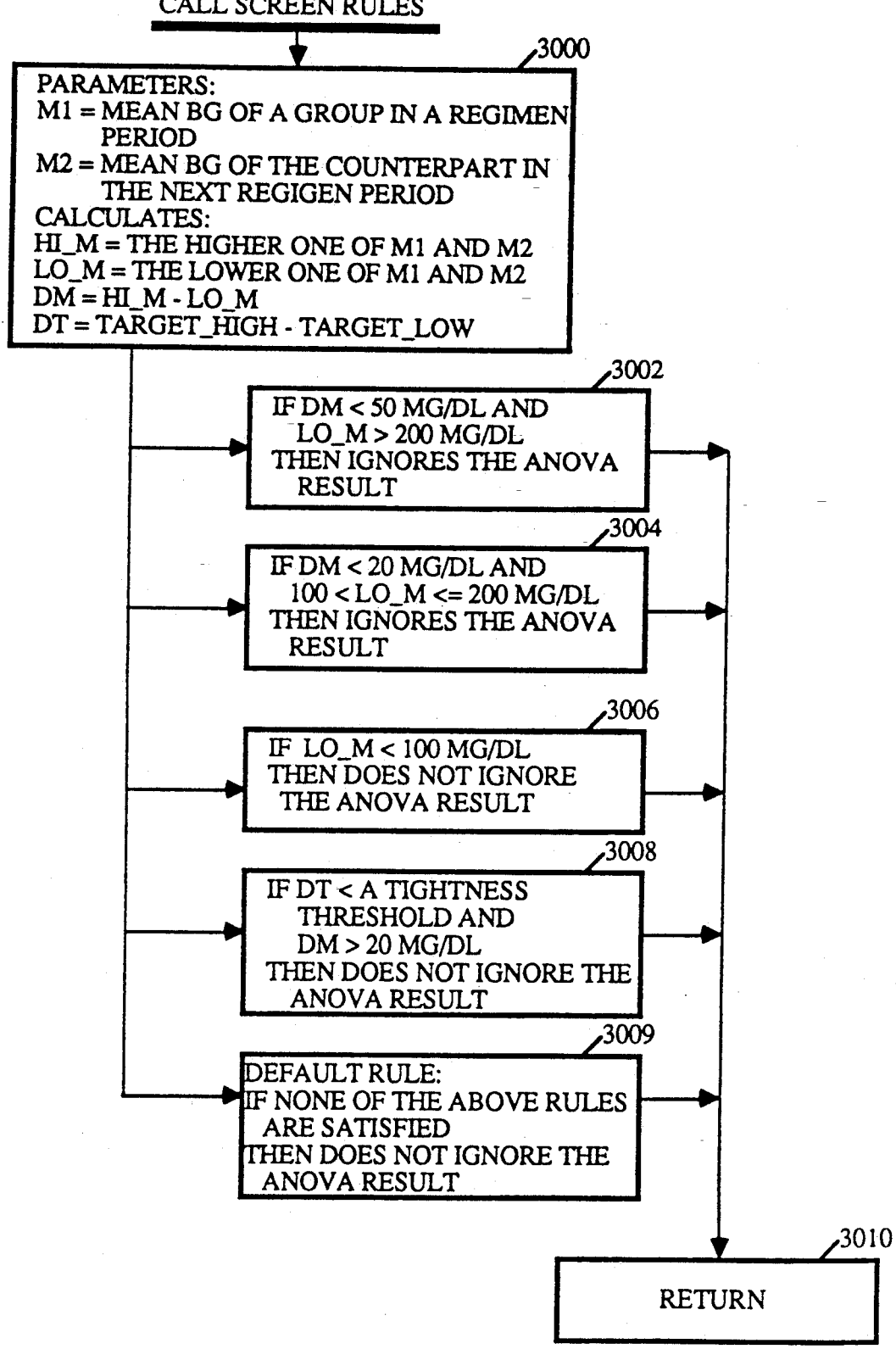

Referring now to FIG. 30, there is shown a flowchart illustrating the manner in which screen rules based on clinical knowledge are used for filtering the statistically significant blood glucose values identified following the performance of the series of ANOVA tests in order to focus only upon the clinically significant blood glucose results. It should be noted that the objective behind the filtering operation is to suppress the presentation of positive ANOVA results in the data interpretation report where the identified changes are statistically significant but clinically irrelevant, so that the reviewing physician is not presented with data which is likely to be of little assistance in therapeutic decision making. Such clinically irrelevant results are not included in the graphical section of the data interpretation report although the associated statistical results may still be useful in pursuing additional data analyses.

In essence, the screen rules are based on advice from clinical experts as to how different do blood glucose values need to be in order to be clinically interesting. It was found that the size of a clinically significant difference depends on the location of the mean blood glucose values and the patient's target range. For instance, mean blood glucose readings in the upper ranges (preferably, greater than 250 mg/dl) may differ by a larger amount than mean blood glucose readings at lower ranges before becoming clinically relevant. In patients attempting to achieve "tight control" (corresponding to blood glucose readings, for instance, between 80 and 120 mg/dl), smaller differences in mean blood glucose readings are more relevant than in patients attempting to achieve mere "fair control" (for instance, blood glucose readings between 100 and 160 mg/dl).

As described above, the ANOVA tests identify statistical differences in two or more sets of blood glucose values, each set having an associated mean and standard deviation in these values. According to a feature of this invention, the clinical relevance of a positive ANOVA result is examined by studying the absolute differences between the highest and lowest mean blood glucose values for corresponding groups of readings in adjacent insulin regimens. As shown in FIG. 30, following the occurrence of a positive ANOVA test result, a set of parameters, including the absolute differences between the higher and lower compared mean blood glucose values, are identified at step 3000. More specifically, a difference mean value DM is calculated as being equal to $HI\_M - LO\_M$, where $HI\_M$ and $LO\_M$ correspond respectively to the higher and lower ones of a mean value M1 corresponding to the mean BG for a group in an insulin regimen and a mean value M2 corresponding to the mean BG for a corresponding group in the adjacent insulin regimen. At this stage, a difference target value DT is identified as the difference between high and low target values corresponding to the patient's BG control goal.

Subsequently, at step 3002, the first screen rule is applied, whereby the positive ANOVA result is ignored if the difference between the higher and lower mean BG, i.e., DM, is found to be less than 50 mg/dl and the lower means value BG $LO\_M$ is found to be greater than 200 mg/dl. Thus, if the rule condition at step 3002 is satisfied, step 3010 is accessed, where the positive ANOVA result is ignored and the program returns to continue with the rest of the data interpretation analyses.

The second screen rule is applied at step 3004, whereby the associated ANOVA result is ignored if the difference mean value DM is found to be less than 20 mg/dl and the lowest mean BG $LO\_M$ is found to be between 100 mg/dl and 200 mg/dl. Again, if the rule condition is satisfied, step 3010 is accessed.

The third screen rule is applied at step 3004, whereby the associated ANOVA result is not ignored if the lowest mean BG $LO\_M$ is found to be less than 100 mg/dl. If this rule condition is satisfied, the change associated with the ANOVA result is identified as being clinically relevant and the program returns at step 3010, and the associated graphical section of the data interpretation report is generated subsequently.

The fourth screen rule is applied at step 3008, whereby, in the case where "tight control" is being attempted, as indicated by the difference target value DT being less than a predefined threshold value (for instance, about 40 mg/dl), a difference mean value DM greater than 20 mg/dl is reported irrespective of the size of the actual mean BG values. Thus, if the rule at step 3008 is satisfied, the associated ANOVA result is not ignored and the program returns at step 3010, and the associated graphical section of the data interpretation report is generated subsequently.

Following the application of the fourth screen rule, a default rule is applied at step 3009 to determine if all four previous rules have not been satisfied and, if so, the associated ANOVA result is not ignored and is identified as being clinically significant. The program returns at step 3010 and the associated graphical section of the report is subsequently generated.

It should be noted that the threshold blood glucose values identified in the screen rules shown at steps 3002-3008 are provided for illustrative purposes only, and may be varied in accordance with application-specific and patient-specific factors.

What is claimed is:

1. A method of operating a digital computer for automated diabetes data interpretation by processing recorded diabetes data, including data corresponding to blood glucose levels and insulin therapy for a diabetic patient taken over a period of time, said method comprising the steps of:
   i) loading said diabetes data into said digital computer;
   ii) processing said diabetes data with said digital computer to
      a) identify insulin intake regimens corresponding to predefined significant changes in insulin therapy which are sustained for at least a predefined segment of said period of time,
      b) identify resulting statistically significant changes in said blood glucose levels across adjacent ones of said identified insulin intake regimens, and
      c) identify clinically significant changes in said blood glucose levels from said identified statistically significant changes; and
   iii) generating an output from said digital computer highlighting the results of said processing of said diabetes data, including details pertaining to said identified insulin intake regimens and said clinically significant changes in said blood glucose levels.

2. The method as claimed in claim 1, wherein said processing of said diabetes data further includes identifying a most significant insulin change associated with each identified clinically significant change in said blood glucose levels.

3. The method as claimed in claim 1, wherein said processing of said diabetes data further includes grouping said diabetes data according to time of day intervals when said diabetes data were taken including respective groups of breakfast, lunch, dinner, and bedtime data.

4. The method of operating a digital computer for automated diabetes data interpretation by processing recorded diabetes data, including data corresponding to blood glucose levels and insulin therapy for a diabetic patient taken over a period of time, said method comprising the steps of:
   i) loading said diabetes data into said digital computer;
   ii) processing said diabetes data with said digital computer to
      a) identify insulin intake regimens corresponding to predefined significant changes in insulin therapy which are sustained for at least a predefined segment of said period of time,
      b) identify resulting statistically significant changes in said blood glucose levels within said identified insulin intake regimens, and
      c) identify clinically significant changes in said blood glucose levels from said identified statistically significant changes; and
   iii) generating an output from said digital computer highlighting the results of said processing of said diabetes data, including details pertaining to said identified insulin intake regimens and said clinically significant changes in said blood glucose levels,
   wherein said predefined significant changes in insulin therapy include (i) a change in number of shots per day, (ii) a change in amount of long-acting insulin, (iii) a change in amount of intermediate-acting insulin, and (iv) a change in amount of short-acting insulin.

5. The method as claimed in claim 4, wherein said predefined significant changes (i), (ii), (iii), and (iv) are ranked in a hierarchy of significance such that change (i) is most significant, change (ii) is less significant than change (i), change (iii), is less significant than change (ii), and change (iv) is less significant than change (iii), and wherein a series of said insulin intake regimens is identified and categorized according to a most significant one of said predefined significant changes (i), (ii), (iii), and (iv) which persists for at least said predefined segment of said period of time.

6. The method as claimed in claim 1, wherein said predetermined segment of said period of time is three days.

7. A method of operating a digital computer for automated diabetes data interpretation by processing recorded diabetes data, including data corresponding to blood glucose levels and insulin therapy for a diabetic patient taken over a period of time, said method comprising the steps of:
   i) loading said diabetes data into said digital computer;
   ii) processing said diabetes data with said digital computer to
      a) identify insulin intake regimens corresponding to predefined significant changes in insulin therapy which are sustained for at least a predefined segment of said period of time,
      b) identify resulting statistically significant changes in said blood glucose levels within said identified insulin intake regimens, and
      c) identify clinically significant changes in said blood glucose levels from said identified statistically significant changes; and
   iii) generating an output from said digital computer highlighting the results of said processing of said diabetes data, including details pertaining to said identified insulin intake regimens and said clinically significant changes in said blood glucose levels, wherein said statistically significant changes in said blood glucose levels are identified by analysis of variance tests on said blood glucose levels and by mealtimes during which said data corresponding to said blood glucose levels were taken.

8. A method of operating a digital computer for automated diabetes data interpretation by processing recorded diabetes data, including data corresponding to blood glucose levels and insulin therapy for a diabetic patient taken over a period of time, said method comprising the steps of:
   i) loading said diabetes data into said digital computer;
   ii) processing said diabetes data with said digital computer to a) identify insulin intake regimens corresponding to predefined significant changes in insulin therapy which are sustained for at least a predefined segment of said period of time,
b) identify resulting statistically significant changes in said blood glucose levels within said identified insulin intake regimens, and
c) identify clinically significant changes in said blood glucose levels from said identified statistically significant changes; and
iii) generating an output from said digital computer highlighting the results of said processing of said diabetes data, including details pertaining to said identified insulin intake regimens and said clinically significant changes in said blood glucose levels,
wherein said clinically significant changes in said blood glucose levels are identified from said identified statistically significant changes by filtering said identified statistically significant changes in accordance with a set of screen rules based on clinical knowledge.

9. The method as claimed in claim 8, wherein said set of screen rules includes a rule dependent on means blood glucose values and a target range for said diabetic patient.

10. The method as claimed in claim 8, wherein said set of screen rules includes a rule dependent on absolute differences between highest and lowest mean blood glucose values for corresponding groups of readings in adjacent insulin intake regimens.

11. A method of operating a digital computer for automated diabetes data interpretation by processing recorded diabetes data, including data corresponding to blood glucose levels and insulin therapy for a diabetic patient taken over a period of time, said method comprising the steps of:
i) loading said diabetes data into said digital computer;
ii) processing said diabetes data with said digital computer to
a) identify insulin intake regimens corresponding to predefined significant changes in insulin therapy which are sustained for at least a predefined segment of said period of time,
b) identify resulting statistically significant changes in said blood glucose levels within said identified insulin intake regimens, and
c) identify clinically significant changes in said blood glucose levels from said identified statistically significant changes; and
iii) generating an output from said digital computer highlighting the results of said processing of said diabetes data, including details pertaining to said identified insulin intake regimens and said clinically significant changes in said blood glucose levels,
wherein said processing of said diabetes data further includes identifying extreme blood glucose readings based on predefined thresholds and generating explanations and characterizations for said extreme blood glucose readings including details on insulin intake most likely to have affected said extreme blood glucose readings.

12. The method as claimed in claim 11, wherein said step of generating said output includes outputting from said digital computer three-day plots including information for a day on which one of said extreme blood glucose reading occurred, as well as an immediately preceding day and an immediately following day.

13. The method as claimed in claim 11, wherein groups of said extreme blood glucose readings are characterized by corresponding ones of said insulin intake regimens, mealtime, and weekday vs. weekend classification.

14. The method as claimed in claim 11, wherein said insulin therapy includes administering different kinds of insulin to said patient, and said explanations include an identification of one of said kinds of insulin which most likely affected said extreme blood glucose readings.

15. The method as claimed in claim 11, wherein said explanations include a mealtime which most likely affected said extreme blood glucose readings.

16. The method as claimed in claim 11, wherein said explanations are generated by checking whether a usual amount of insulin was taken at least a threshold percentage of time in time intervals corresponding to a particular mealtime and a particular insulin type within one of said insulin intake regimens corresponding to each of said extreme blood glucose readings.

17. The method as claimed in claim 11, wherein said explanations identify an unusually high dose of insulin.

18. The method as claimed in claim 11, wherein said explanations identify an unusually low dose of insulin.

19. The method as claimed in claim 11, wherein said explanations are generated by checking whether most of said extreme blood glucose readings not otherwise explained occur within only one of said insulin intake regimens.

20. The method as claimed in claim 11, wherein said explanations are generated by checking whether most extreme blood glucose readings not otherwise explained occur within only one of a plurality of daily time intervals.

21. The method as claimed in claim 11, wherein said explanations are generated by checking whether most extreme blood glucose readings not otherwise explained occur on weekends.

22. The method as claimed in claim 11, wherein some of said explanations covering a greater number of said extreme blood glucose readings are selected and others of said explanations covering a lesser number of said extreme blood glucose readings are rejected.

23. The method as claimed in claim 1, further comprising the step of analyzing glycemic control and hypoglycemic conditions of said patient.

24. A method of operating a digital computer for automated diabetes data interpretation by processing recorded diabetes data, including data corresponding to blood glucose levels and insulin therapy for a diabetic patient taken over a period of time, said method comprising the steps of:
i) loading said diabetes data into said digital computer;
ii) processing said diabetes data with said digital computer to
a) identify insulin intake regimens corresponding to predefined significant changes in insulin therapy which are sustained for at least a predefined segment of said period of time,
b) identify resulting statistically significant changes in said blood glucose levels within said identified insulin intake regimens, and
c) identify clinically significant changes in said blood glucose levels from said identified statistically significant changes; and
iii) generating an output from said digital computer highlighting the results of said processing of said diabetes data, including details pertaining to said identified insulin intake regimens and said clinically significant changes in said blood glucose levels, further comprising the step of analyzing glycemic control and hypoglycemic conditions of said patient, wherein said step of analyzing glycemic control and hypoglycemic conditions of said patient includes computing statistics for blood glucose readings.

25. The method as claimed in claim 24, wherein a separate group of statistics are computed for each insulin intake regimen.

26. The method as claimed in claim 23, wherein said step of analyzing glycemic control and hypoglycemic conditions for said patient include identifying possible hypoglycemic conditions likely to result when the patient's average blood glucose is lowered to reach a therapeutic goal.

27. A method of operating a digital computer for automated diabetes data interpretation by processing recorded diabetes data including data corresponding to blood glucose levels and insulin therapy for a diabetic patient taken over a period of time, said method comprising the steps of:
   i) loading said diabetes data into said digital computer;
   ii) processing said diabetes data with said digital computer to
      a) identify insulin intake regimens corresponding to predefined significant changes in insulin therapy which are sustained for at least a predefined segment of said period of time,
      b) identify resulting statistically significant changes in said blood glucose levels within said identified insulin intake regimens, and
      c) identify clinically significant changes in said blood glucose levels from said identified statistically significant changes; and
   iii) generating an output from said digital computer highlighting the results of said processing of said diabetes data, including details pertaining to said identified insulin intake regimens and said clinically significant changes in said blood glucose levels,
   where said steps of generating an output from said digital computer includes generating a global summary including identification of said insulin intake regimens having statistically different effects on blood glucose levels, a comparison of said patient's average blood glucose level to a prescribed target range for said patient, and a report of occurrence of extreme ones of said blood glucose levels of said patient.

28. A method of operating a digital computer for automated diabetes data interpretation by processing recorded diabetes data, including data corresponding to blood glucose levels and insulin therapy for a diabetic patient taken over a period of time, said method comprising the steps of:
   i) loading said diabetes data into said digital computer;
   ii) processing said diabetes data with said digital computer to
      a) identify insulin intake regimens corresponding to predefined significant changes in insulin therapy which are sustained for at least a predefined segment of said period of time,
      b) identify resulting statistically significant changes in said blood glucose levels within said identified insulin intake regimens, and
      c) identify clinically significant changes in said blood glucose levels from said identified statistically significant changes; and
   iii) generating an output from said digital computer highlighting the results of said processing of said diabetes data, including details pertaining to said identified insulin intake regimens and said clinically significant changes in said blood glucose levels,
   wherein said step of generating an output from said digital computer includes generating an insulin dose summary including data specifying a display of said insulin intake regimens as a bar graph on a time line illustrating a relative duration of each of said insulin intake regimens.

29. The method as claimed in claim 28, wherein said insulin dose summary includes data specifying a display of a histogram of insulin dosages for each of said insulin intake regimens.

30. The method as claimed in claim 28, wherein said insulin dose summary includes data specifying a separate histogram for breakfast, lunch and supper mealtimes for each of said insulin intake regimens.

31. The method as claimed in claim 30, wherein said insulin dose summary includes data specifying separate histograms for different kinds of insulin.

32. A method of operating a digital computer for automated diabetes data interpretation by processing recorded diabetes data, including data corresponding to blood glucose levels and insulin therapy for a diabetic patient taken over a period of time, said method comprising the steps of:
   i) loading said diabetes data into said digital computer;
   ii) processing said diabetes data with said digital computer to
      a) identify insulin intake regimens corresponding to predefined significant changes in insulin therapy which are sustained for at least a predefined segment of said period of time,
      b) identify resulting statistically significant changes in said blood glucose levels within said identified insulin intake regimens, and
      c) identify clinically significant changes in said blood glucose levels from said identified statistically significant changes; and
   iii) generating an output from said digital computer highlighting the results of said processing of said diabetes data, including details pertaining to said identified insulin intake regimens and said clinically significant changes in said blood glucose levels,
   wherein said step of generating an output from said digital computer includes generating data specifying a bar graph indicating insulin dose recording frequency with regions on said bar graph marked to indicate either a presence or absence of recorded data for respective time periods on said bar graph corresponding to said regions.

33. A method of operating a digital computer for automated diabetes data interpretation by processing recorded diabetes data, including data corresponding to blood glucose levels and insulin therapy for a diabetic patient taken over a period of time, said method comprising the steps of:
   i) loading said diabetes data into said digital computer;

ii) processing said diabetes data with said digital computer to
  a) identify insulin intake regimens corresponding to predefined significant changes in insulin therapy which are sustained for at least a predefined segment of said period of time,
  b) identify resulting statistically significant changes in said blood glucose levels within said identified insulin intake regimens, and
  c) identify clinically significant changes in said blood glucose levels from said identified statistically significant changes; and
iii) generating an output from said digital computer highlighting the results of said processing of said diabetes data, including details pertaining to said identified insulin intake regimens and said clinically significant changes in said blood glucose levels,
wherein said step of generating an output from said digital computer includes generating data specifying a bar graph indicating blood glucose measurement frequency with regions on said bar graph marked to indicate either a presence or absence of recorded data for respective time periods on said bar graph.

34. A method of operating a digital computer for automated diabetes data interpretation by processing recorded diabetes data, including data corresponding to blood glucose levels and insulin therapy for a diabetic patient taken over a period of time, said method comprising the steps of:
i) loading said diabetes data into said digital computer;
ii) processing said diabetes data with said digital computer to
  a) identify insulin intake regimens corresponding to predefined significant changes in insulin therapy which are sustained for at least a predefined segment of said period of time,
  b) identify resulting statistically significant changes in said blood glucose levels within said identified insulin intake regimens, and
  c) identify clinically significant changes in said blood glucose levels from said identified statistically significant changes; and
iii) generating an output from said digital computer highlighting the results of said processing of said diabetes data, including details pertaining to said identified insulin intake regimens and said clinically significant changes in said blood glucose levels,
wherein said step of generating an output from said digital computer includes generating data specifying separate histograms of glucose measurements taken during respective ones of said insulin intake regimens.

35. The method as claimed in claim 34, wherein a separate set of said histograms for said insulin intake regimens is generated for each of a plurality of different daily mealtimes.

36. A method of operating a digital computer for automated diabetes data interpretation by processing recorded diabetes data, including data corresponding to blood glucose levels and insulin therapy for a diabetic patient taken over a period of time, said method comprising the steps of:
i) loading said diabetes data into said digital computer;
ii) processing said diabetes data with said digital computer to
  a) identify insulin intake regimens corresponding to predefined significant changes in insulin therapy which are sustained for at least a predefined segment of said period of time,
  b) identify resulting statistically significant changes in said blood glucose levels within said identified insulin intake regimens, and
  c) identify clinically significant changes in said blood glucose levels from said identified statistically significant changes; and
iii) generating an output from said digital computer highlighting the results of said processing of said diabetes data, including details pertaining to said identified insulin intake regimens and said clinically significant changes in said blood glucose levels,
wherein said step of generating an output from said digital computer includes generating language-independent tokens representing text, and replacing the language-independent tokens with corresponding phrases in a selected natural language.

37. A method of operating a digital computer for automated diabetes data interpretation by processing recorded diabetes data, including data corresponding to insulin therapy for a diabetic patient taken over a period of time, said method comprising the steps of:
i) loading said diabetes data into said digital computer;
ii) processing said diabetes data with said digital computer to identify a series of insulin intake regimens corresponding to predefined significant changes in insulin therapy which are sustained for at least a predefined segment of said period of time; and
iii) generating an output from said digital computer identifying said series of intake regimens in said period of time;
wherein said predefined significant changes include a hierarchy of clinically significant changes, and wherein said series of insulin intake regimens is identified as having a most significant one of said changes in said hierarchy which is sustained for at least said predefined segment of said period of time.

38. The method as claimed in claim 37, wherein said hierarchy of clinically significant changes includes, in order of most significant to least significant: (i) a change in number of shots per day; (ii) a change in amount of long-acting insulin; (iii) a change in amount of intermediate acting insulin; and (iv) a change in amount of short-acting insulin.

39. The method as claimed in claim 37, wherein said step of processing includes sequentially scanning said diabetes data for a most significant one of said changes in said hierarchy to identify a series of two runs separated by said most significant one of said changes within said period of time, and checking whether said two runs each have a duration of at least said predetermined segment of said period of time in order to accept said series of said two runs as said series of insulin intake regimens when said two runs each have a duration of at least said predetermined segment of said period of time, and otherwise sequentially scanning said diabetes data for a next-most significant ones of said changes in said hierarchy.

40. A method of operating a digital computer for analysis and display of diabetes data, including data corresponding to blood glucose levels and insulin therapy for a diabetic patient taken over a period of time, said method comprising the steps of:

i) loading said diabetes data into said digital computer;
ii) processing said diabetes data with said digital computer to generate graphical data specifying a visual image; and
iii) outputting said graphical data from said digital computer to an output device generating said visual image;

wherein said graphical data specifies a first bar graph displaying insulin dose recording frequency on a first time line, said first bar graph having regions selectively marked to indicate either a presence or absence of recorded insulin dose data at respective times on said first time line, and wherein said graphical data specifies a second bar graph displaying blood glucose recording frequency on a second time line, said second bar graph having areas marked to indicate either a presence or absence of recorded blood glucose data at respective times on said second time line.

41. The method as claimed in claim 40, wherein said output device is a video display displaying said visual image.

42. The method as claimed in claim 40, wherein said output device is a printer generating said visual image as a graph printed on paper.

43. The method as claimed in claim 40, wherein said regions in said first bar graph are marked with a gray scale having an intensity indicating said insulin dose recording frequency.

44. The method as claimed in claim 40, wherein said areas in said second bar graph are rectangular for each day in said period of time and are subdivided along a direction perpendicular to said second time line into respective sub-areas that are selectively marked to indicate said presence or absence of said recorded blood glucose data at daily time intervals including mealtimes.

45. The method as claimed in claim 44, wherein said sub-areas are rectangles which collectively form a checkerboard pattern.

46. The method as claimed in claim 40, wherein said graphical data specifies graphical symbols that are displayed above said second bar graph and indicate lifestyle activities of said patient for respective times along said second time line.

47. A method of operating a digital computer for analysis and display of diabetes data, including data corresponding to blood glucose levels and insulin therapy for a diabetic patient taken over a period of time, said method comprising the steps of:
i) loading said diabetes data into said digital computer;
ii) processing said diabetes data with said digital computer to generate graphical data specifying components of a visual image; and
iii) outputting said graphical data from said digital computer to an output device generating said visual image;

wherein said components of said visual image include:
a) a global summary including identification of insulin treatment regimens having statistically different effects on said blood glucose levels, a comparison of said patient's average blood glucose level to a prescribed target range for said patient, and a report of occurrences of extreme ones of said blood glucose levels of said patient;
b) an insulin dose summary including a display of said insulin intake regimens on a first time line illustrating a relative duration of each of said insulin intake regimens;
c) a glucose measurement summary including a display of blood glucose measurements arranged on a second time line;
d) an analysis of said blood glucose measurements including statistics and complicating factors for predefined daily time intervals; and
e) an analysis of said extreme ones of said blood glucose levels and explanations and characterizations for said extreme ones of said blood glucose levels.

48. The method as claimed in claim 47, wherein said insulin dose summary includes a display of separate histograms of insulin doses for breakfast, lunch, and supper mealtimes for each of said insulin intake regimens.

49. The method as claimed in claim 48, wherein said insulin dose summary includes separate histograms for different kinds of insulin.

50. The method as claimed in claim 47, wherein said insulin does summary displays insulin dose recording frequency as gray-scale values on said first time line.

51. The method as claimed in claim 47, wherein said glucose measurement summary includes a bar graph having regions selectively marked to indicate either a presence or absence of recorded blood glucose data at respective mealtimes.

52. The method as claimed in claim 47, wherein said glucose measurement summary includes graphical symbols that are displayed on said second time line and indicate life-type activities of said patient for respective times along said second time line.

53. The method as claimed in claim 47, wherein said complicating factors include possible hypoglycemic conditions likely to result when the patient's average blood glucose is lowered to reach a therapeutic goal.

54. The method as claimed in claim 47, wherein said analysis of blood glucose measurements includes a series of histograms for said insulin intake regimens.

55. The method as claimed in claim 54, wherein said histograms in said series are linked by annotations identifying significant changes in insulin therapy between said insulin intake regimens.

56. The method as claimed in claim 47, wherein said analysis of said blood glucose measurements includes a matrix of summary statistics including overall statistics and statistics for daily mealtimes.

57. The method as claimed in claim 47, wherein said analysis of said extreme ones of said blood glucose levels includes three-day plots including days before, during and after each of said extreme ones of said blood-glucose levels.

58. The method as claimed in claim 57, wherein each of said three-day plots including days before, during and after each of said extreme ones of said blood-glucose levels includes a numeric symbol quantifying said each of said extreme ones of said blood glucose levels, and a graph of other blood glucose values for daily mealtimes.

* * * * *